United States Patent
Kheradvar et al.

(10) Patent No.: US 10,792,396 B2
(45) Date of Patent: *Oct. 6, 2020

(54) METHODS FOR DEVELOPMENT OF HYBRID TISSUE ENGINEERED VALVE WITH POLYURETHANE CORE

(71) Applicant: The Regents of the University of California, Oakland, CA (US)

(72) Inventors: Arash Kheradvar, Irvine, CA (US); Ramin Zareian, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/198,116

(22) Filed: Nov. 21, 2018

(65) Prior Publication Data

US 2019/0151509 A1    May 23, 2019

Related U.S. Application Data

(60) Provisional application No. 62/589,433, filed on Nov. 21, 2017, provisional application No. 62/630,183, filed on Feb. 13, 2018.

(51) Int. Cl.

| A61L 27/38 | (2006.01) |
| A61F 2/24 | (2006.01) |
| A61L 27/36 | (2006.01) |
| A61L 27/50 | (2006.01) |
| A61L 27/34 | (2006.01) |
| A61L 27/06 | (2006.01) |
| A61L 27/18 | (2006.01) |

(52) U.S. Cl.
CPC ........ *A61L 27/3808* (2013.01); *A61F 2/2415* (2013.01); *A61L 27/06* (2013.01); *A61L 27/18* (2013.01); *A61L 27/34* (2013.01); *A61L 27/3604* (2013.01); *A61L 27/3826* (2013.01); *A61L 27/507* (2013.01); *A61L 2430/20* (2013.01)

(58) Field of Classification Search
CPC .................................................. A61L 27/3808
See application file for complete search history.

(56) References Cited

PUBLICATIONS

Stachelek et al. Gene Therapy, 2004, 11:15-24.*
Stachelek et al. Ann Thorac Surg., 2006, 81:47-56.*
Wisman et al. Trans Am Soc Artif Intern Organs. 1982, 28:164-168.*
Mol et al., Circulation, 2006, 114:I-152-I-158.*
Bloomfield ,Heart, 2002, 87:583-589.*

* cited by examiner

*Primary Examiner* — Bin Shen

(74) *Attorney, Agent, or Firm* — Knobbe, Martens, Olson & Bear, LLP

(57) ABSTRACT

A hybrid tissue engineered heart valve leaflet including a polyurethane core, such as a polycarbonate-based thermoplastic polyurethane like carbothane. The polyurethane core is enclosed within one or more layer of a patient's cells and collagen. Also disclosed are hybrid tissue engineered heart valves, including a frame; and at least two leaflets attached thereto in a configuration of a heart valve, wherein the leaflets are hybrid tissue engineered heart valve leaflets, and methods of making a hybrid tissue engineered heart valve for deployment in a patient.

19 Claims, 31 Drawing Sheets

METHODS FOR DEVELOPMENT OF HYBRID TISSUE ENGINEERED VALVE WITH POLYURETHANE CORE

STATEMENT REGARDING FEDERALLY SPONSORED R&D

This invention was made with government support under Grant Number HL119893, awarded by The National Institutes of Health. The Government has certain rights in the invention.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

A method for development of a novel hybrid tissue engineered heart valve with a polyurethane core is described.

BACKGROUND

Currently there are two basic types of heart valves (mechanical and bioprosthetic valves). A mechanical heart valve is made from materials that do not include any form of biological tissue. However, patients using mechanical valves need anticoagulation therapy. The current tissue bioprosthetic heart valves have lower durability, functionality and more calcification in short time for patients. Thus, each type of valve has its own disadvantages. It is vital to design and build a novel tissue valve to overcome the above issues.

Valvular heart disease is the third-most common cause of heart problems in the United States. Replacement of dysfunctional valves markedly reduces valve disease-related morbidity and mortality. Valvular heart disease (VHD) prevalence is currently projected at 2.5% in the U.S. population and sharply increases after the age of 65 (Lung, B. and A. Vahanian, *Epidemiology of valvular heart disease in the adult*. Nat Rev Cardiol, 2011. 8(3): p. 162-172), with more than 110,000 heart valve replacement procedures performed in the United States; among those, more than 80% are bioprosthetic heart valves (BHVs), including both surgical and transcatheter (Lung, B. and A. Vahanian, *Epidemiology of valvular heart disease in the adult*. Nat Rev Cardiol, 2011. 8(3): p. 162-172).

Currently, only two main types of artificial heart valves (i.e., mechanical and bioprosthetic) are available to replace a diseased natural valve. Mechanical heart valves (MHVs), tend to last longer than BHVs, but they carry a greater long-term risk for thromboembolism that may lead to stroke and arterial thrombosis. In contrast, BHVs (including transcatheter valves), possess a biocompatible surface and improved blood flow dynamics but have a shorter lifespan due to degeneration and calcification. MHVs are the only recommended option for younger patients, mainly because of their durability (Goldstone, A. B., et al., *Mechanical or Biologic Prostheses for Aortic-Valve and Mitral-Valve Replacement*. New England Journal of Medicine, 2017. 377(19): p. 1847-1857). However, the lifelong need for anticoagulant medication is a major drawback to these valves. In contrast, BHVs—made of either porcine or bovine tissue—may not require anticoagulant medications because of their biocompatible surface and improved blood flow dynamics. Although more recent studies suggest anticoagulant medications even for patients with BHVs (Jose, J., et al., *Clinical Bioprosthetic Heart Valve Thrombosis After Transcatheter Aortic Valve Replacement: Incidence, Characteristics, and Treatment Outcomes*. JACC: Cardiovascular Interventions, 2017. 10(7): p. 686-697). Compared to MHVs, BHVs' lower risks of thrombogenicity and superior hemodynamics have given these valves remarkable advantages. However, BHVs have a higher tendency for calcification with limited durability due to progressive degeneration whose rate is inversely related to the patient's age at the time of implantation (Stephens, E. H., et al., *Age-Related Changes in Material Behavior of Porcine Mitral and Aortic Valves and Correlation to Matrix Composition*. Tissue Engineering Part A. 16(3): p. 867-878; Ong, S. H., R. Mueller, and S. Iversen, *Early calcific degeneration of a CoreValve transcatheter aortic bioprosthesis*. Eur Heart J, 2012. 33(5): p. 586; and Harbaoui, B., et al., *Early Edwards SAPIEN Valve Degeneration After Transcatheter Aortic Valve Replacement*. JACC Cardiovasc Interv, 2016. 9(2): p. 198-9). Transcatheter valve-in-valve implantation is currently a solution for degenerating BHVs only in older patients (Azadani, A. N. and E. E. Tseng, *Transcatheter heart valves for failing bioprostheses: state-of-the-art review of valve-in-valve implantation*. Circ Cardiovasc Interv, 2011. 4(6): p. 621-8; and Dvir, D. and J. G. Webb, *Transcatheter aortic valve-in-valve implantation for patients with degenerative surgical bioprosthetic valves*. Circ J, 2015. 79(4): p. 695-703). Nevertheless, the number of valve-in-valve procedures a person can take in the lifetime is limited, as the valve orifice area will be smaller with each successive procedure. Therefore, younger patients in need of heart valve replacement currently face the dilemma of choosing between two equally unappealing therapeutic choices: MHVs with the need for anticoagulant medications for life, or BHVs with limited durability and need for replacement. The current guidelines recommend BHVs only for patients older than 65, due to a higher tendency for degeneration and calcification in younger patients (Hoffmann, G., G. Lutter, and J. Cremer, *Durability of bioprosthetic cardiac valves*. Dtsch Arztebl Int, 2008. 105(8): p. 143-8).

Recently, Tissue Engineered Heart Valves (TEHV's) have been emerged as a new solution to replace the diseased heart valves for young or old patients (Hoerstrup, S. P., et al., *Functional living trileaflet heart valves grown in vitro*. Circulation, 2000. 102(19 Suppl 3): p. III44-9; Sutherland, F. W., et al., *From stem cells to viable autologous semilunar heart valve*. Circulation, 2005. 111(21): p. 2783-91; Gottlieb, D., et al., *In vivo monitoring of function of autologous engineered pulmonary valve*. J Thorac Cardiovasc Surg, 2010. 139(3): p. 723-31; and Flanagan, T. C., et al., *In vivo remodeling and structural characterization of fibrin-based tissue-engineered heart valves in the adult sheep model*. Tissue Eng Part A, 2009. 15(10): p. 2965-76). Yet, the current TEHVs are not able to adjust their composition inside heart for a long time and withstand against the dynamic loads generated from blood flow (Stock, U. A., et al., *Tissue-engineered valved conduits in the pulmonary circulation*. J Thorac Cardiovasc Surg, 2000. 119(4 Pt 1): p. 732-40; and Sodian, R., et al., *Early in vivo experience with tissue-engineered trileaflet heart valves*. Circulation, 2000. 102(19 Suppl 3): p. III22-9). One major TEHVs' issue is the shrinkage of the tissue constructs due to migration and contraction of the host's smooth muscles cells (SMCs) over the valve leaflets (Gottlieb, D., et al., *In vivo monitoring of* function of autologous engineered pulmonary valve. J Thorac Cardiovasc Surg, 2010. 139(3): p. 723-31; Flanagan, T. C., et al., *In vivo remodeling and structural characterization of fibrin-based tissue-engineered heart valves in the adult sheep model.* Tissue Eng Part A, 2009. 15(10): p. 2965-76; and Driessen-Mol, A., et al., *Transcatheter implantation of homologous "off-the-shelf" tissue-engineered heart valves with self-repair capacity: long-term functionality and rapid in vivo remodeling in sheep.* J Am Coll Cardiol, 2014. 63(13): p. 1320-1329). Degradable scaffolds (e.g., synthetic polymers) (Hoerstrup, S. P., et al., *Functional living trileaflet heart valves grown in vitro.* Circulation, 2000. 102(19 Suppl 3): p. 11144-9; Sutherland, F. W., et al., *From stem cells to viable autologous semilunar heart valve.* Circulation, 2005. 111(21): p. 2783-91; and Sodian, R., et al., *Early in vivo experience with tissue-engineered trileaflet heart valves.* Circulation, 2000. 102(19 Suppl 3): p. 11122-9) and purely biological material (Flanagan, T. C., et al., *In vivo remodeling and structural characterization of fibrin-based tissue-engineered heart valves in the adult sheep model.* Tissue Eng Part A, 2009. 15(10): p. 2965-76; and Jockenhoevel, S., et al., *Tissue engineering: complete autologous valve conduit—a new moulding technique.* Thorac Cardiovasc Surg, 2001. 49(5): p. 287-90) used in the current TEHVs lead to poor leaflet coaptation, followed by progressive regurgitation and valvular insufficiency.

Tissue engineering promises to overcome the limitations of conventional heart valves by offering a living tissue option. However, despite meaningful and encouraging early results for TEHVs, either decellularized xenogeneic or purely biologic, these valves have been found to be incapable of adjusting their composition to withstand the hemodynamic loads to which they are exposed, mainly in the left heart. Tissue-engineered leaflets are found to shrink due to host myofibroblasts' infiltration within their degradable scaffolds, resulting in poor leaflet coaptation, followed by progressive regurgitation that ultimately leads to valvular insufficiency.

Targeted Patient Population and Clinical Unmet Need:

Based on the most recent guidelines (Baumgartner H, Falk V, Bax J J, De Bonis M, Hamm C, Holm P J, lung B, Lancellotti P, Lansac E, Rodriguez Muñoz D, Rosenhek R, Sjögren J, Tornos Mas P, Vahanian A, Walther T, Wendler O, Windecker S, Zamorano J L, Group ESCSD. 2017 esc/eacts guidelines for the management of valvular heart disease. *European Heart Journal.* 2017; 38:2739-2791; and Nishimura R A, Otto C M, Bonow R O, Carabello B A, Erwin J Pr, Fleisher L A, Jneid H, Mack M J, McLeod C J, O'Gara P T, Rigolin V H, Sundt T Mr, A. T. 2017 aha/acc focused update of the 2014 aha/acc guideline for the management of patients with valvular heart disease: A report of the american college of cardiology/american heart association task force on clinical practice guidelines. *Circulation.* 2017; 135:e1159-e1195), BHVs are only recommended for patients older than 65, due to a higher tendency for calcification in younger patients. The targeted patient population for the hybrid TEHV (H-TEHV) would be patients younger than 65 whose only recommended option is MHVs. Further, although native mitral valve is bileaflet with a dynamic annulus, currently all clinically-approved bioprostheses have been developed as trileaflet valves. Thus, there is an unmet clinical need for very durable mitral valves that mimic the native valve function and will not degenerate over time.

SUMMARY

Disclosed are hybrid tissue engineered heart valves and methods for their development. In one embodiment, the hybrid tissue engineered heart valve comprises leaflets comprising a polyurethane core, made of a polycarbonate-based thermoplastic polyurethane enclosed within layers of a patient's own cells and collagen. Such patient-specific heart valve leaflets provide self-regeneration and lifelong durability.

In a further embodiment, the hybrid tissue valve comprises of titanium (main frame) and polycarbonate-based thermoplastic polyurethanes (TPUs) leaflets.

Methods for making hybrid tissue valves are also disclosed. In one embodiment, the TPU leaflets are sewn to the titanium frame. The cells are extracted from patient's vein and mixed with collagen type I. Then, the valve leaflets are coated with the mixed cell and collagen solution. One significant advantage of the new hybrid valves is self-regeneration and durability for patients.

Some embodiments relate to a hybrid tissue engineered heart valve leaflet including a polyurethane core.

In some embodiments, the polyurethane core is a polycarbonate-based thermoplastic polyurethane.

In some embodiments, the polycarbonate-based thermoplastic polyurethane is carbothane.

In some embodiments, the polyurethane core is enclosed within one or more layer of a patient's cells and collagen.

In some embodiments, the cells are extracted from the patient's vasculature.

In some embodiments, the cells are extracted from a peripheral vein of the patient.

In some embodiments, the peripheral vein is a saphenous or a jugular vein.

In some embodiments, a first layer of the one or more layer of the patient's cells include smooth muscle cells and fibroblast cells and a second layer of the one or more layer of the patient's cells includes endothelial cells.

In some embodiments, the first layer includes 80-95% fibroblast cells and 5-20% smooth muscle cells.

In some embodiments, the collagen is collagen type I.

Some embodiments relate to a hybrid tissue engineered heart valve, including a frame; and at least two leaflets attached thereto in a configuration of a heart valve, wherein the leaflets are hybrid tissue engineered heart valve leaflets as disclosed herein.

In some embodiments, the leaflets are made of a polycarbonate-based thermoplastic polyurethane.

In some embodiments, the polycarbonate-based thermoplastic polyurethane is carbothane.

In some embodiments, the valve is a tri-leaflet valve.

In some embodiments, the valve is a mitral valve with a dynamic saddle-shaped annulus.

In some embodiments, the frame includes titanium.

Some embodiments relate to a method of making a hybrid tissue engineered heart valve for deployment in a patient, the method including:

cutting a polyurethane mesh into the shape of heart valve leaflets to obtain a polyurethane mesh leaflet, attaching at least two polyurethane mesh leaflets to a heart valve frame, harvesting autologous cells from the patient; and growing the cells on the surface of the polyurethane mesh leaflets under culture conditions sufficient to enclose the polyurethane mesh leaflets.

In some embodiments, the cells are harvested from a peripheral vessel, selected from a saphenous or a jugular vein.

In some embodiments, the cells are smooth muscle cells, fibroblast cells and/or endothelial cells.

In some embodiments, the method includes at least two steps of growing cells, a first step of growing smooth muscle cells and/or fibroblast cells on the leaflets to obtain first cell-enclosed leaflets, and a second step of growing endothelial cells on the surface of the first-cell enclosed leaflets to obtain endothelial cell-enclosed polyurethane mesh leaflets.

To address the significant clinical unmet need with an ultimate goal of eliminating this dilemma for younger patients, we have developed Hybrid Tissue Engineered Heart Valves (H-TEHVs) that, unlike BHVs, are principally composed of live autologous tissue harvested from the same subject. The concept of H-TEHV is based on using a non-degradable mesh as the valve scaffold and then enclosing that with different autologous cell types (e.g., vascular smooth muscle cells [SMCs], vascular fibroblast [FB] cells, and endothelial cells) to fulfill the role of valvular interstitial cells (VICs) and valvular endothelial cells, respectively (Alavi, S. H. and A. Kheradvar, *Metal mesh scaffold for tissue engineering of membranes*. Tissue Engineering Part C: Methods, 2012. 18(4): p. 293-301; and Alavi, S. H. and A. Kheradvar, *A hybrid tissue-engineered heart valve*. The Annals of thoracic surgery, 2015. 99(6): p. 2183-2187). In a previous study, we used extra-thin superelastic Nitinol mesh as the valve scaffold (Alavi, S. H. and A. Kheradvar, *A hybrid tissue-engineered heart valve*. The Annals of thoracic surgery, 2015. 99(6): p. 2183-2187), but due to durability concerns (Alavi, S. H., et al., *A Tri-Leaflet Nitinol Mesh Scaffold for Engineering Heart Valves*. Annals of Biomedical Engineering, 2017. 45(2): p. 413-426), more recently, we have been using biocompatible thermoplastic polyurethane mesh leaflets as the scaffold that we tested their durability for heart valve applications. The valve scaffold made of thermoplastic polyurethane is enclosed by layers of live tissue constructs harvested and grown from sheep's own vascular tissue. FIG. 1 presents the development steps related to the H-TEHV from tissue extraction to the final valve in three steps.

A bileaflet H-TEHV, with a dynamic annulus is optimal for the mitral position by combining an elastomeric core scaffold encased by living autologous tissue, covered with the patient's endothelium. The non-degradable core supports the valve mechanically and resists tissue contraction, and the living tissue maintains extracellular matrix (ECM) homeostasis and a non-thrombogenic surface.

As confirmed by our in vitro and in vivo preliminary results, H-TEHVs function smoothly inside the heart with no leaks and no delamination, and their thin elastomeric mesh scaffold replicates a native valve's strong ECM backbone. This approach differs fundamentally from other heart valve tissue-engineering efforts that use either decellularized xenogeneic or degradable scaffolds.

Development of a Bioinspired, Hybrid, Bileaflet Mitral TEHV and Optimize its Hemodynamics In Vitro.

We have developed bileaflet mitral H-TEHVs in vitro by creating cell layers tightly enclosing the leaflets of a bioinspired valve scaffold made of thermoplastic polyurethane mesh. The scaffold's entire surface is covered with a layer of living fibroblasts and functional endothelium to prevent thromboembolic events. Mitral valves, developed in different sizes, and with different aspect ratios, are implanted in our heart flow simulator to test whether they produce better hemodynamics compared to standard trileaflet valves.

We have developed a reproducible adaptation and conditioning protocol to optimize hybrid TEHVs' cellular performance under physiologic pressure. We mount the bileaflet H-TEHVs in physiologic heart valve bioreactors and subject them to progressive increases in pressures and flow to evaluate cell viability and the valve's ability to maintain ECM homeostasis. Such mechanistic studies on scaffold-cell interactions demonstrate in vitro tissue formation and optimization of valve development with minimal delamination. These conditioning protocols allow development of ready-to-implant valves with optimal composition.

We have analyzed the hybrid bileaflet TEHV's function, hemodynamics, and biocompatibility in vivo by implanting the valves in the mitral position of an ovine model. The optimally-designed and bioreactor-conditioned H-TEHVs are implanted in the mitral position of up to 20 sheep. Each sheep receives a valve made from its own cells. Valve function and hemodynamics are assessed using echocardiography. The plasma levels of cytokines are assayed for 24 weeks prior to euthanizing the animals to evaluate the implants' histopathology. We have analyzed the H-TEHV's microstructure and deposition of ECM components post-implant to optimize tissue formation that mimics native valves.

Clinical Unmet Need

"Younger" patients in need of heart valve replacement currently face the dilemma of choosing between two equally unappealing therapeutic choices: MHVs with the need for anticoagulant medications for life, or BHVs with limited durability and need for replacement. For younger patients, generally those below 65 years old, MHVs pose risks of bleeding and stroke, limiting patients' active personal and professional lives. Alternatively, surgical BHVs have a durability of 10-15 years (Salaun E, Clavel M-A, Rodés-Cabau J, Pibarot P. Bioprosthetic aortic valve durability in the era of transcatheter aortic valve implantation. *Heart*. 2018). Nevertheless, due to the MHVs' risks and limitations, many younger patients accept the potential for complications in multiple reoperations and settle for BHVs.

Hybrid Tissue Engineered Heart Valves (H-TEHVs) eliminate this dilemma for younger patients by delivering what heart surgeons believe to be a transformative innovation: a heart valve that remains functional for life without the need for anticoagulant medication. Unlike all BHVs, a H-TEHV with living tissue would maintain ECM homeostasis and provide a non-thrombogenic surface. In addition, unlike all other TEHVs, a H-TEHV is composed of autologous tissue cultured on a non-degradable scaffold capable of withstanding the hemodynamic environment in the left heart. The H-TEHV may be surgically-implantable or implanted by transcatheter delivery.

The hybrid valve overcomes traditional MHVs' and BHVs' disadvantages by mimicking a native valve's biocompatibility and hemodynamics while maintaining adequate strength and durability. H-TEHV is a desired solution for patients younger than 65 who may not receive BHVs due to the chance of durability concerns, while preferring to avoid the risks of bleeding and stroke due to anticoagulant medications needed for MHVs, which limit their active personal and professional lives. Because heart valve replacement surgery is an elective procedure, most patients can wait for about six weeks to have their autologous H-TEHV created. FIG. 2 outlines the steps to have a H-TEHV developed and implanted in a patient.

Prevalence of Heart Valve Disease:

Valvular heart disease (VHD), has been a major driving force behind the growing attention to cardiovascular science over the past 60 years (Lung B, Vahanian A. Epidemiology of valvular heart disease in the adult. *Nature reviews. Cardiology*. 2011; 8:162-172). VHD prevalence is projected at 2.5% in the U.S. population and sharply increases after age 65 (Lung B, Vahanian A. Epidemiology of valvular heart disease in the adult. *Nature reviews. Cardiology.* 2011; 8:162-172), with more than 110,000 heart valve replacement procedures performed annually in the United States and nearly 300,000 worldwide (Egbe A C, Pislaru S V, Pellikka P A, Poterucha J T, Schaff H V, Maleszewski J J, Connolly H M. Bioprosthetic valve thrombosis versus structural failure. *Journal of the American College of Cardiology.* 2015; 66:2285; and Pibarot P, dumesnil JG. Prosthetic heart valves: Selection of the optimal prosthesis and long-term management. *Circulation.* 2009; 119:1034-1048). Globally, the majority of morbidity and mortality attributable to VHD is due to rheumatic heart disease (RHD), commonly seen in countries with lower incomes (Coffey S, Cairns B J, Jung B. The modern epidemiology of heart valve disease. *Heart.* 2016; 102:75-85). Alternatively, the greatest burden of VHD in developed countries is due to calcific valve disease. Although VHD prevalence compared to coronary heart disease is low, the need for long-term follow-up and treatment costs shows that the impact of VHD on healthcare systems is disproportionately large (Coffey S, Cairns B J, Jung B. The modern epidemiology of heart valve disease. *Heart.* 2016; 102:75-85).

Tissue Engineered Heart Valves

Despite meaningful and encouraging early results of tissue-engineered heart valves (Hoerstrup S P, Sodian R, Daebritz S, Wang J, Bacha E A, Martin D P, Moran A M, Guleserian K J, Sperling J S, Kaushal S. Functional living trileaflet heart valves grown in vitro. *Circulation.* 2000; 102:111-44-111-49; Sutherland F W H, Perry T E, Yu Y, Sherwood M C, Rabkin E, Masuda Y, Garcia G A, McLellan D L, Engelmayr Jr G C, Sacks M S. From stem cells to viable autologous semilunar heart valve. *Circulation.* 2005; 111:2783-2791; Gottlieb D, Kunal T, Emani S, Aikawa E, Brown D W, Powell A J, Nedder A, Engelmayr Jr G C, Melero-Martin J M, Sacks M S. In vivo monitoring of function of autologous engineered pulmonary valve. *The Journal of Thoracic and Cardiovascular Surgery.* 2010; 139:723-731; and Flanagan T C, Sachweh J S, Frese J, Schnoring H, Gronloh N, Koch S, Tolba R H, Schmitz-Rode T, Jockenhoevel S. In vivo remodeling and structural characterization of fibrin-based tissue-engineered heart valves in the adult sheep model. *Tissue Engineering Part A.* 2009; 15:2965-2976), these valves have been found to be mostly unable to adjust their composition to withstand various types of dynamic loads to which they are exposed in the heart, principally in the left ventricle (Hoerstrup S P, Sodian R, Daebritz S, Wang J, Bacha E A, Martin D P, Moran A M, Guleserian K J, Sperling J S, Kaushal S. Functional living trileaflet heart valves grown in vitro. *Circulation.* 2000; 102:III-44-III-49; Sutherland F W H, Perry T E, Yu Y, Sherwood M C, Rabkin E, Masuda Y, Garcia G A, McLellan D L, Engelmayr Jr G C, Sacks M S. From stem cells to viable autologous semilunar heart valve. *Circulation.* 2005; 111:2783-2791; Stock U A, Nagashima M, Khalil P N, Nollert G D, Herdena T, Sperling J S, Moran A, Lien J, Martin D P, Schoen F J. Tissue-engineered valved conduits in the pulmonary circulation. *The Journal of Thoracic and Cardiovascular Surgery.* 2000; 119:732-740; and Sodian R, Hoerstrup S P, Sperling J S, Daebritz S, Martin D P, Moran A M, Kim B S, Schoen F J, Vacanti J P, Mayer Jr J E. Early in vivo experience with tissue-engineered trileaflet heart valves. *Circulation.* 2000; 102:111-22-III-29). The in situ tissue-engineered heart valve, once expected to be a promising alternative to MHVs and BHVs, faces many challenges for translation to the clinic (Stassen O M J A, Muylaert D E P, Bouten C V C, Hjortnaes J. Current challenges in translating tissue-engineered heart valves. *Current Treatment Options in Cardiovascular Medicine.* 2017; 19:71). The valves' fragility when exposed to higher ventricular pressures explains why they have been implanted only at the right heart thus far. Additionally, the tissue-engineered leaflets are found to shrink due to migration and contraction of the host's myofibroblasts over the constructs post-implantation (Gottlieb D, Kunal T, Emani S, Aikawa E, Brown D W, Powell A J, Nedder A, Engelmayr Jr G C, Melero-Martin J M, Sacks M S. In vivo monitoring of function of autologous engineered pulmonary valve. *The Journal of Thoracic and Cardiovascular Surgery.* 2010; 139:723-731; Flanagan T C, Sachweh J S, Frese J, Schnöring H, Gronloh N, Koch S, Tolba R H, Schmitz-Rode T, Jockenhoevel S. In vivo remodeling and structural characterization of fibrin-based tissue-engineered heart valves in the adult sheep model. *Tissue Engineering Part A.* 2009; 15:2965-2976; Syedain Z H, Lahti M T, Johnson S L, Robinson P S, Ruth G R, Bianco R W, Tranquillo R T. Implantation of a tissue-engineered heart valve from human fibroblasts exhibiting short term function in the sheep pulmonary artery. *Cardiovascular Engineering and Technology.* 2011; 2:101-112; and Driessen-Mol A, Emmert M Y, Dijkman P E, Frese L, Sanders B, Weber B, Cesarovic N, Sidler M, Leenders J, Jenni R, Grunenfelder J, Falk V, Baaijens F P T, Hoerstrup S P. Transcatheter implantation of homologous "off-the-shelf" tissue-engineered heart valves with self-repair capacity: Long-term functionality and rapid in vivo remodeling in sheep. *Journal of the American College of Cardiology.* 2014; 63:1320-1329). Shrinkage of the leaflets, developed mainly from degradable scaffolds (e.g., synthetic polymers (Hoerstrup S P, Sodian R, Daebritz S, Wang J, Bacha E A, Martin D P, Moran A M, Guleserian K J, Sperling J S, Kaushal S. Functional living trileaflet heart valves grown in vitro. *Circulation.* 2000; 102:III-44-III-49; Sutherland F W H, Perry T E, Yu Y, Sherwood M C, Rabkin E, Masuda Y, Garcia G A, McLellan D L, Engelmayr Jr G C, Sacks M S. From stem cells to viable autologous semilunar heart valve. *Circulation.* 2005; 111:2783-2791; and Sodian R, Hoerstrup S P, Sperling J S, Daebritz S, Martin D P, Moran A M, Kim B S, Schoen F J, Vacanti J P, Mayer Jr J E. Early in vivo experience with tissue-engineered trileaflet heart valves. *Circulation.* 2000; 102:III-22-III-29) and purely biologic material (Flanagan T C, Sachweh J S, Frese J, Schnoring H, Gronloh N, Koch S, Tolba R H, Schmitz-Rode T, Jockenhoevel S. In vivo remodeling and structural characterization of fibrin-based tissue-engineered heart valves in the adult sheep model. *Tissue Engineering Part A.* 2009; 15:2965-2976; Syedain Z H, Lahti M T, Johnson S L, Robinson P S, Ruth G R, Bianco R W, Tranquillo R T. Implantation of a tissue-engineered heart valve from human fibroblasts exhibiting short term function in the sheep pulmonary artery. *Cardiovascular Engineering and Technology.* 2011; 2:101-112 and Jockenhoevel S, Chalabi K, Sachweh J, Groesdonk H, Demircan L, Grossmann M, Zund G, Messmer B. Tissue engineering: Complete autologous valve conduit—a new moulding technique. *The Thoracic and cardiovascular surgeon.* 2001; 49:287-290), results in poor leaflet coaptation (FIG. 3), followed by progressive regurgitation and valvular insufficiency (Kheradvar A, Groves E M, Dasi L P, Alavi S H, Tranquillo R, Grande-Allen K J, Simmons C A, Griffith B, Falahatpisheh A, Goergen C J. Emerging trends in heart valve engineering: Part i. Solutions for future. *Annals of Biomedical Engineering.* 2015; 43:833-843). A more recent study suggest that the remodeled valves show little development of the native valves' tri-layered microstructure, in which the top, middle and underlying sections of each leaflet have different compositions and mechanical properties (Emmert M Y, Schmitt B A, Loerakker S, Sanders B, Spriestersbach H, Fioretta E S, Bruder L, Brakmann K, Motta S E, Lintas V, Dijkman P E, Frese L, Berger F, Baaijens F P T, Hoerstrup S P. Computational modeling guides tissue-engineered heart valve design for long-term in vivo performance in a translational sheep model. *Science Translational Medicine.* 2018; 10). It is suspected that a reason behind the lack of success of current methods in heart valve tissue engineering is their use of purely biologic scaffolding, via either decellularized xenogeneic or degradable scaffolds. All these approaches aim to replicate valve tissue as it is currently seen in adults. However, they do not consider the fact that a natural heart valve develops in the heart over a long time. This development process begins in the embryonic stages where the heart is only a beating tube with low pressure, and then continues as it gets conditioned and adapts to withstand an extreme pressure load, mainly in the left heart. The current state of science makes it impossible for existing TEHVs to totally replicate all of the heart's embryonic, postnatal, and adult environments to develop a heart valve with strong natural ECM that lasts for life. The H-TEHVs disclosed herein address this shortcoming. Patient-specific valves with lifelong durability, especially in younger patients are an unmet clinical need. Current artificial heart valves are either limited in durability or require lifelong anticoagulation therapy. An ideal valve substitute for the mitral position is a bileaflet, hybrid construct based on a non-degradable core scaffold and autologous cells.

Our transformative mitral H-TEHV technology addresses the unmet clinical needs, particularly for younger patients, by mimicking the native valve's biocompatibility and hemodynamics while maintaining adequate strength and durability.

The concept of "hybrid" tissue-engineered constructs: We are the first group that has introduced the concept of "hybrid" tissue-engineered membranes using a non-degradable mesh scaffold as a core to make a tissue-engineered construct (FIG. 4), as evidenced by our five issued U.S. patents (U.S. Pat. Nos. 10,016,461, 9,968,446, 9,925,296, 8,936,650 and 8,900,862), multiple U.S. and international pending patents, and published articles (Alavi S H, Kheradvar A. Mesh enclosed tissue constructs 2014; Alavi S H, Kheradvar A. Mesh enclosed tissue constructs 2015; Alavi S H, Liu, W. F., Kheradvar, A Inflammatory response assessment of a hybrid tissue-engineered heart valve leaflet. *Ann Biomed Eng.* 2013; 41:316-326; Alavi S H, Kheradvar A. Metal mesh scaffold for tissue engineering of membranes. *Tissue Engineering Part C Methods.* 2012; 18:293-301; Alavi S H, Kheradvar A. Tgf-beta 1 positively modulates cell-metal interaction in cardiovascular applications. *Circulation Research.* 2012; 111 and Alavi S H, Kheradvar A. A hybrid tissue-engineered heart valve. *The Annals of thoracic surgery.* 2015; 99:2183-2187).

Hybrid TEHVs: We have extended the hybrid tissue-engineering concept to heart valves. The H-TEHV is cultured with different autologous live cell layers to fulfill the role of valvular interstitial cells (VICs), covered by valvular endothelial cells, respectively (Alavi S H, Kheradvar A. A hybrid tissue-engineered heart valve. *The Annals of thoracic surgery.* 2015; 99:2183-2187; Alavi S H, Kheradvar A. Metal mesh scaffold for tissue engineering of membranes. *Tissue Engineering Part C: Methods.* 2012; 18:293-301; and Alavi S H, Liu W F, Kheradvar A Inflammatory response assessment of a hybrid tissue-engineered heart valve leaflet. *Ann Biomed Eng.* 2013; 41:316-326). Equivalent cellular phenotypes are present in the ventricularis, fibrosa, and spongiosa layers of natural heart valves (Della Rocca F, Sartore S, Guidolin D, Bertiplaglia B, Gerosa G, Casarotto D, Pauletto P. Cell composition of the human pulmonary valve: A comparative study with the aortic valve—the vesalio* project. *The Annals of thoracic surgery.* 2000; 70:1594-1600).

Enhanced biocompatibility: The H-TEHV's smooth surface, and the autologous cells that constantly adjust the H-TEHV's ECM content, and hide the permanent scaffold, eliminate the need for lifelong anticoagulation medication and concerns related to biocompatibility, as supported by our preliminary results (Alavi S H, Liu W F, Kheradvar A. Inflammatory response assessment of a hybrid tissue-engineered heart valve leaflet. *Ann Biomed Eng.* 2013; 41:316-326). This is particularly beneficial for younger patients who cannot receive BHVs due to premature calcification, and thus typically require several valve replacement procedures over a lifetime.

Improved resilience: An elastomeric mesh scaffold made of FDA-approved biocompatible thermoplastic polyurethane (Carbothane), which serves as the hybrid leaflet's primary load-bearing component, preserves the valve's structural integrity when subjected to high pressure in the heart, and is expected to increase durability. Based on our accelerated wear test experiment, Carbothane scaffolds exceed 50 million cycles.

Bio-inspired mitral valve: This application focuses on developing the first bio-inspired bileaflet mitral H-TEHV with dynamic annulus. This novel bio-inspired mitral valve system will offer the advantages that a native bileaflet mitral valve with dynamic annulus has to offer for left ventricular function. The bio-inspired mitral valve concept is protected by two issued U.S. patents (U.S. Pat. Nos. 8,876,897 and 9,968,445) and multiple pending.

DETAILED DESCRIPTION

Hybrid tissue engineered heart valves are disclosed. The hybrid tissue valves may comprise leaflets including a polyurethane core, made of a polycarbonate-based thermoplastic polyurethane enclosed within layers of a patient's own cells and collagen. The hybrid tissue valve may further comprise a titanium (main frame), wherein the polycarbonate-based thermoplastic polyurethanes (TPUs) leaflets are attached thereto in the configuration of a heart valve.

To build the hybrid tissue valve, in some embodiments, the cells are extracted from a patient's vein. For example, a peripheral vein or a piece of it such as but not limited to saphenous or jugular vein is removed from the patient in a surgery room. The extracted cells from the vein are grown and sorted, e.g., with an antibody that recognizes a cell surface protein, such as CD 31 Antibody-IgG2a (Bio-Rad Company), which recognizes platelet endothelial cell adhesion molecule (PECAM-1) on the surfaces of platelets, monocytes, neutrophils, and some types of T-cells, in a cell culture hood. The sorted cells may be mixed with collagen, e.g., type I and the inner and outer surfaces of valve leaflets may be coated with the cells and collagen.

A hybrid heart valve, as disclosed herein, may be deployed into a patient heart (e.g., Mitral or Aortic positions) in an open-heart surgery. The hybrid heart valve deployment and follow-up may be monitored with current procedural imaging modalities.

EXAMPLE 1

Implantation of a Hybrid Tissue Engineered Heart Valve in Sheep's Mitral Position We have tested the feasibility of implantation and short-term performance of a novel hybrid tissue-engineered heart valve (H-TEHV) in an ovine model. The H-TEHV's leaflets were composed of a non-degradable elastomeric mesh scaffold enclosed between layers of live tissues grown from the subject's own cells (ovine here). A 23 mm valve scaffold was developed according to the size of juvenile ovine's mitral position. The animal's jugular vein was harvested to extract, isolate, and expand smooth muscle cells/fibroblast and endothelial cells. Then, the valve scaffold was sequentially coated by the sorted cells mixed with collagen type I. The developed hybrid valve was implanted in the same sheep's mitral position via an open-heart surgery. Post-procedure echocardiography showed excellent valve performance without regurgitation. The animal was recovered from anesthesia and transferred on his feet to vivarium without any sign of stroke. The animal expired from pulmonary edema eight hours after completion of the surgery. After autopsy, the H-TEHV was found to remain intact without any tissue dehiscence.

Figure 1:
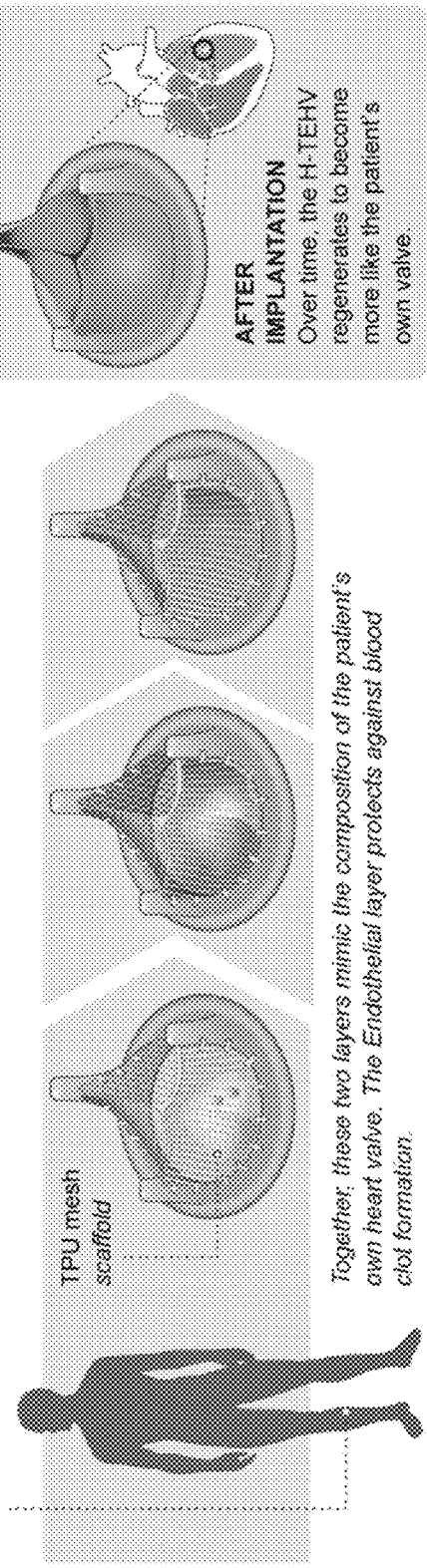
FIG. 1. Steps related to the development of H-TEHV from tissue extraction to final valve in three steps.
Figure 2:
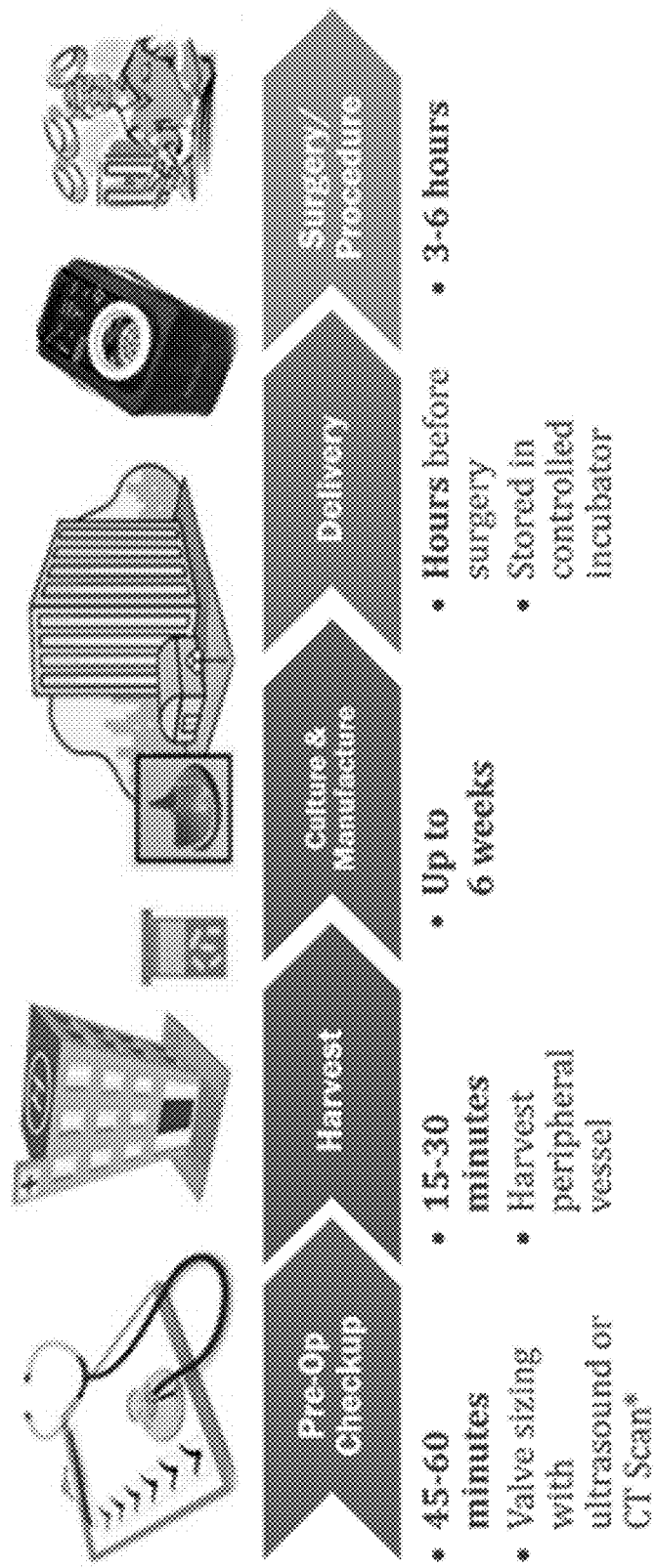
FIG. 2. Summary of the steps to have a H-TEHV made and implanted in a patient. The process starts with valve sizing and cell harvest. Then up to six weeks is required to create the valve (currently we will perform this step in 3 weeks for sheep). Then the valve is shipped via portable bioreactor (e.g., Micro Q Technologies, Scottsdale, Ariz.) to be implanted in the patient.
Figure 3:
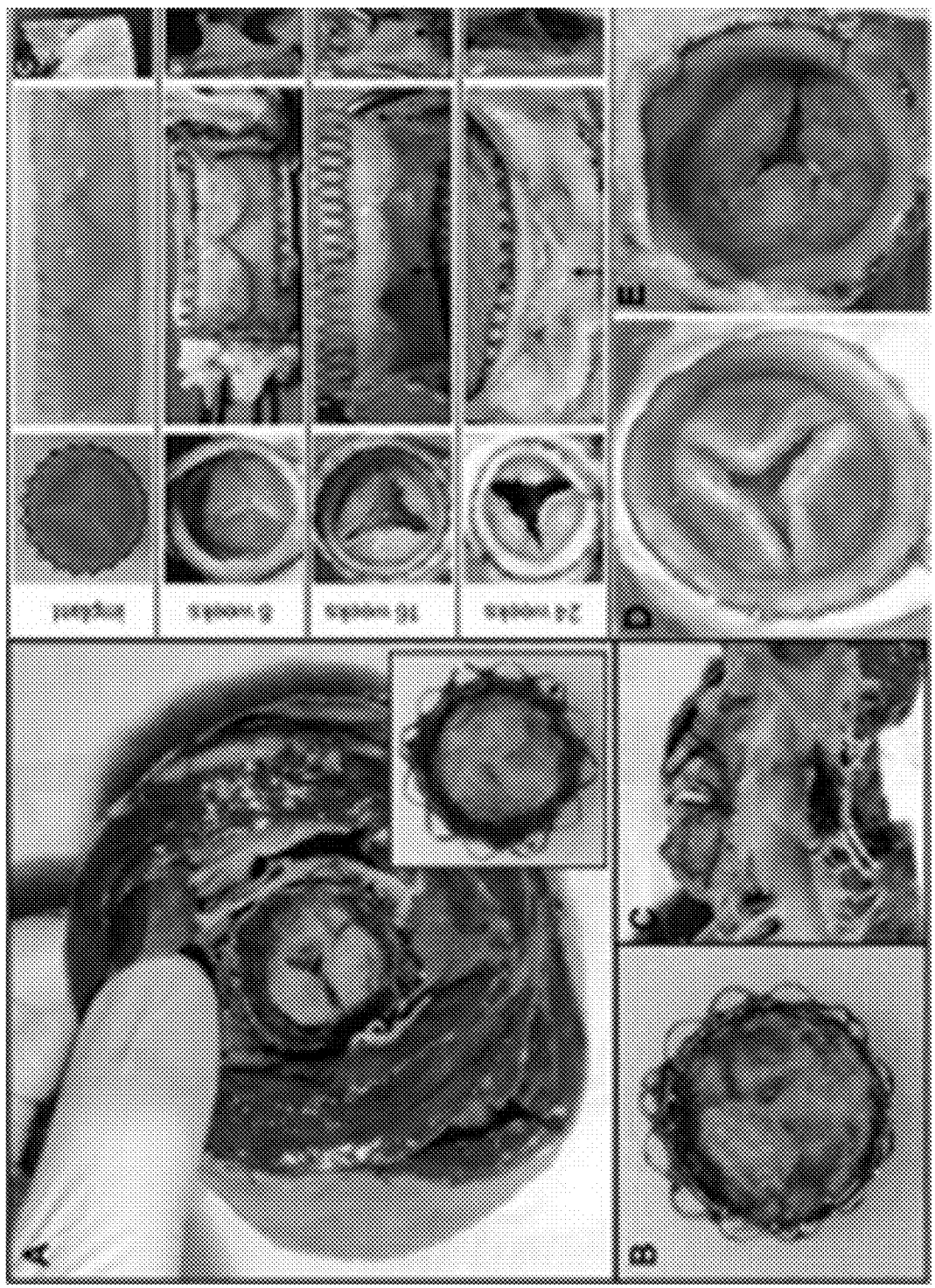
FIGS. 3. (A), (B) and (C) TEHV developed by Emert et al. 2012. Explanted tissue-engineered heart valves (TEHV) at 1 and 2 weeks after implantation. Valvular insufficiency due to leaflet shrinkage can be observed; (D) and (E) Valve leaflets and wall of the explanted TEHV after 4 weeks, by Schmidt et al, 2010. Top right: gradual shrinkage of implanted TEHV in week 8, 16, and 24. The valves are totally shrunken by 24th week (Driessen-Mol A, et al, 2014).
Figure 4:
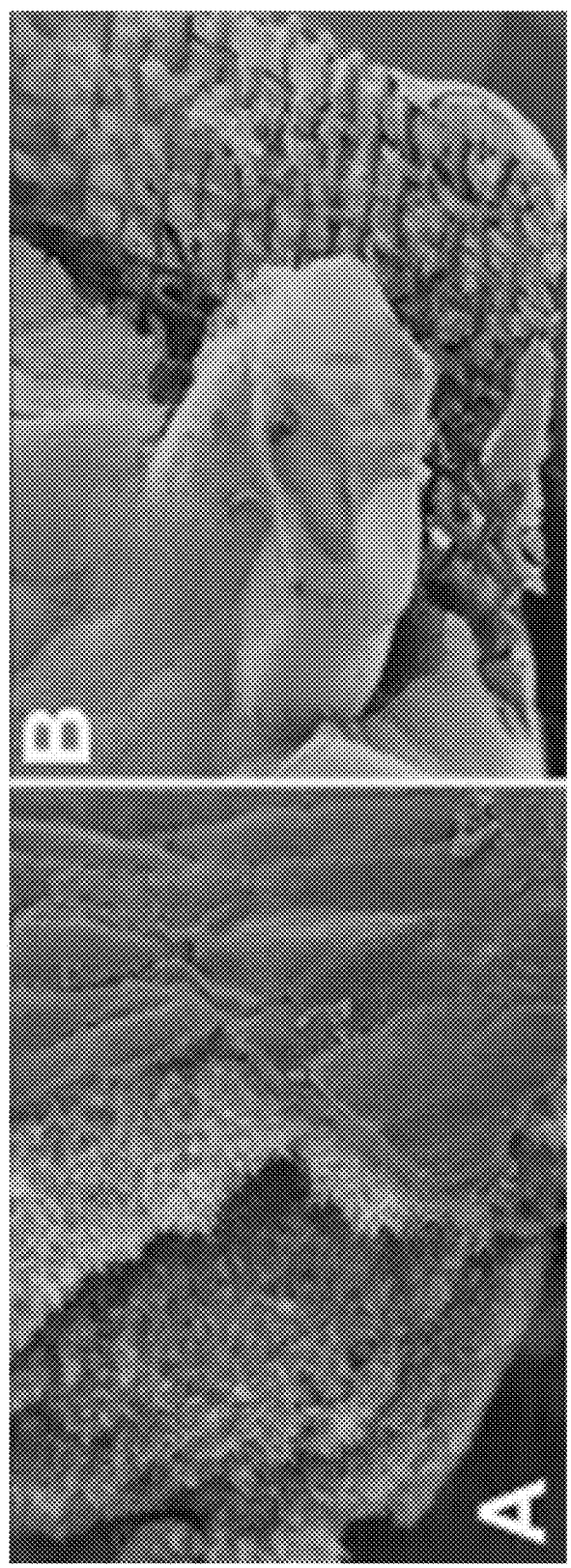
FIG. 4. Concept of hybrid tissue-engineered membrane. Scanning electron microscopy with three layers of cells showing the formed tissue enclosing a mesh scaffold; (A) tissue formed from three different cell layers in sequence: endothelial layer, fibroblast/myofibroblast, and smooth muscle cells; (B) the mesh is integrated within the tissue construct and the cells have penetrated through the mesh's opening holes. Images are from Alavi and Kheradvar, Tissue Eng Part C 2012, 18(4): 293-301. This image was featured on the journal cover.
Figure 5:
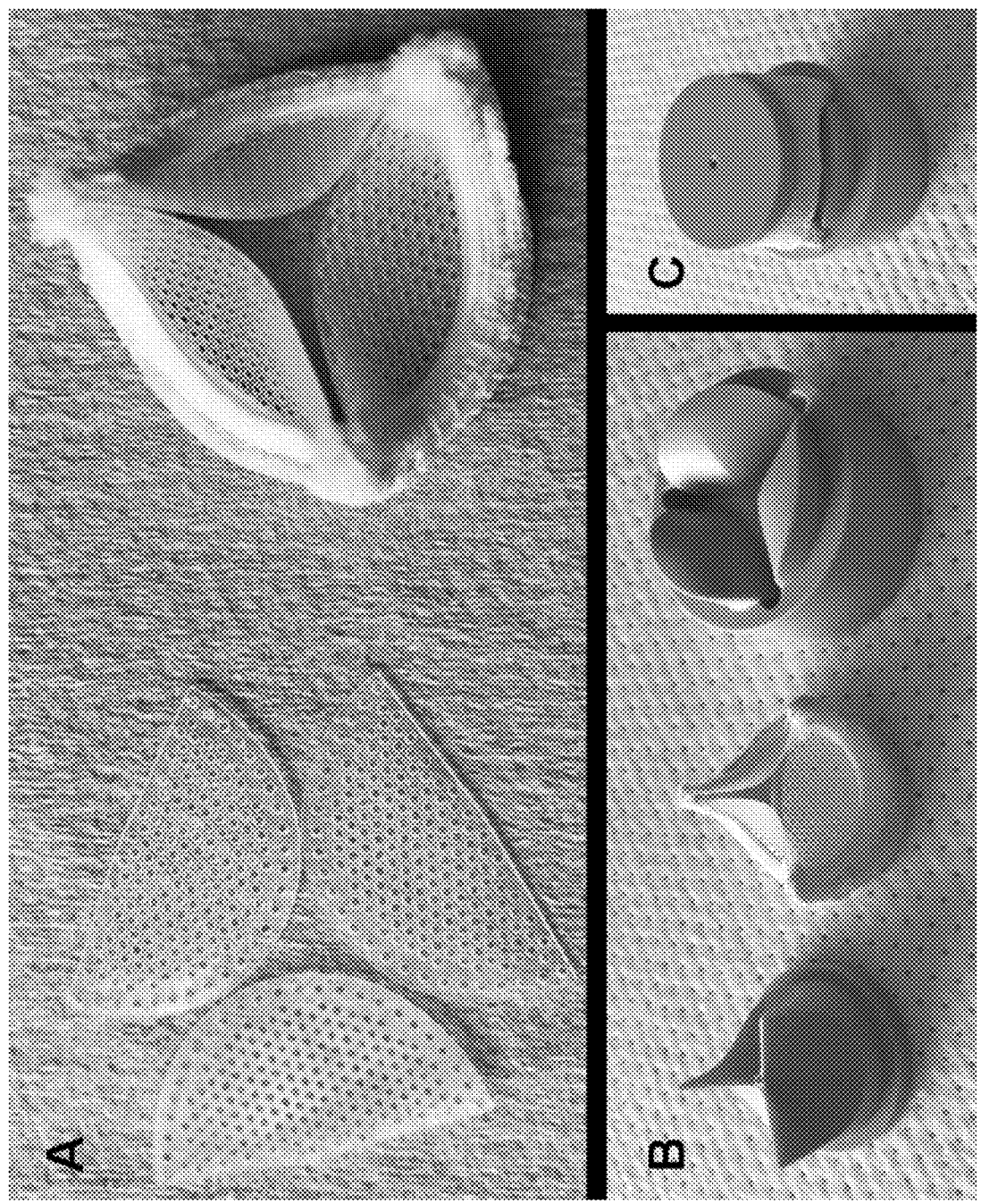
FIG. 5. H-TEHV scaffold (A) Carbothane leaflets. (B) and (C) Leaflets sewn into a 3D titanium frame to form a tri-leaflet valve scaffold.

Development and Testing of H-TEHV Scaffold:

Carbothane AC-4095A is a biocompatible thermoplastic polyurethane (TPU) with mechanical properties that makes it an ideal candidate for heart valve scaffold due to its combination of flexibility and durability. Carbothane has been shown to have a relatively low propensity to calcify, and has been recommended as an appropriate material for cardiovascular implant applications (Yang, M., et al., *Assessing the resistance to calcification of polyurethane membranes used in the manufacture of ventricles for a totally implantable artificial heart*. J Biomed Mater Res, 1999. 48(5): p. 648-59). Carbothane mesh leaflets were designed in Solidworks and were cut by laser into the desire shape. Three leaflets made of Carbothane were sewn to a 3D printed Titanium frame to form the tri-leaflet valve scaffold (FIG. 5, A). Surgical fabric was used to cover the Titanium valve frame and for the purpose of sewing the valve to the mitral annulus.

Figure 6:
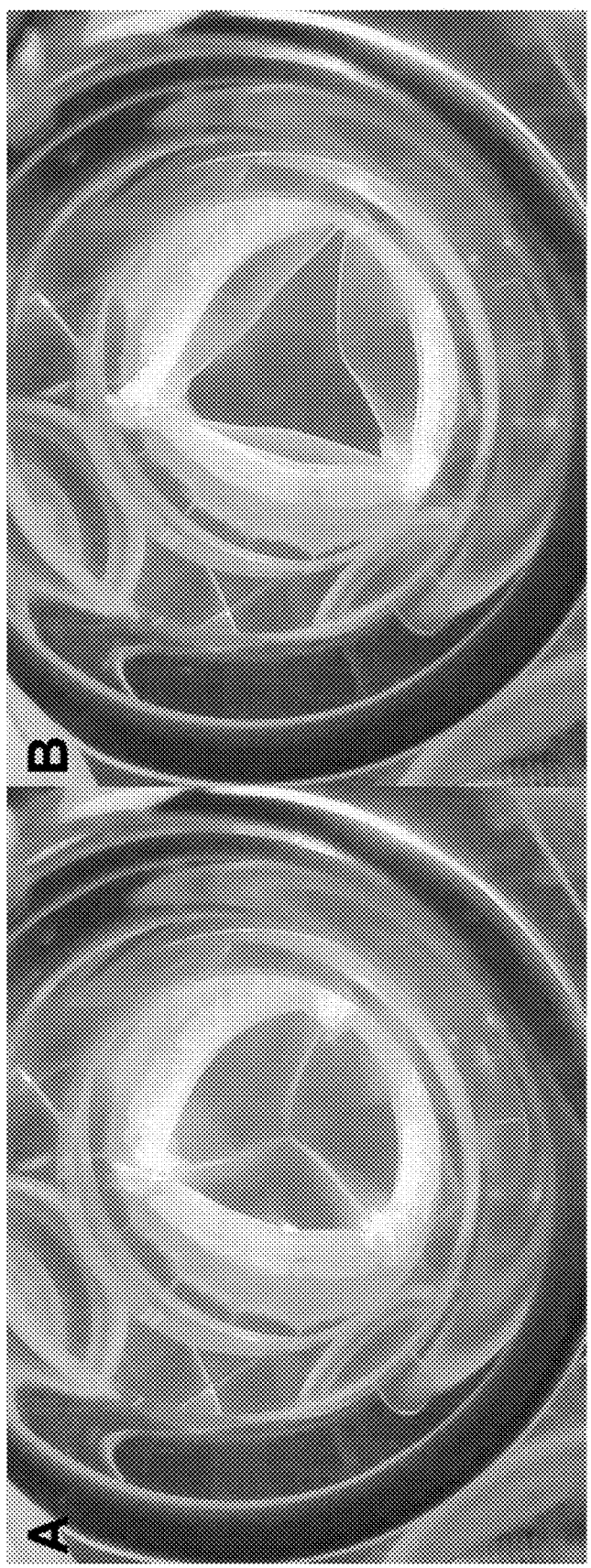
FIG. 6. Valve scaffold inside Accelerated Wear Testing (AWT) system (A) closed, (B) open.

We tested the durability of the Carbothane valve scaffolds (n=2) in an Accelerated Wear Testing (AWT) system (M6 Heart Valve Durability Tester, Dynatek Labs, Galena, Mo.). To do so, non-meshed polymeric valve scaffolds were mounted in the appropriate test fixtures and placed into the M6 Heart Valve Durability Tester. The valves were immersed in normal saline solution and maintained at 37° C. for the test duration. Full opening and closure of the valves were achieved at 800 cycles per minute (CPM). FIGS. 6, (A) and (B) show the images captured from the full closure and opening of the valve scaffold inside the AWT system, respectively. The peak differential pressure during the valve closure was maintained at 120 mmHg. Testing was conducted for 50 million cycles, or nearly 45 days. This duration is equivalent to almost 15 months in a human heart. Both valves were observed under microscope to evaluate the leaflets, sutures and posts after 50 million cycles.

Figure 7:
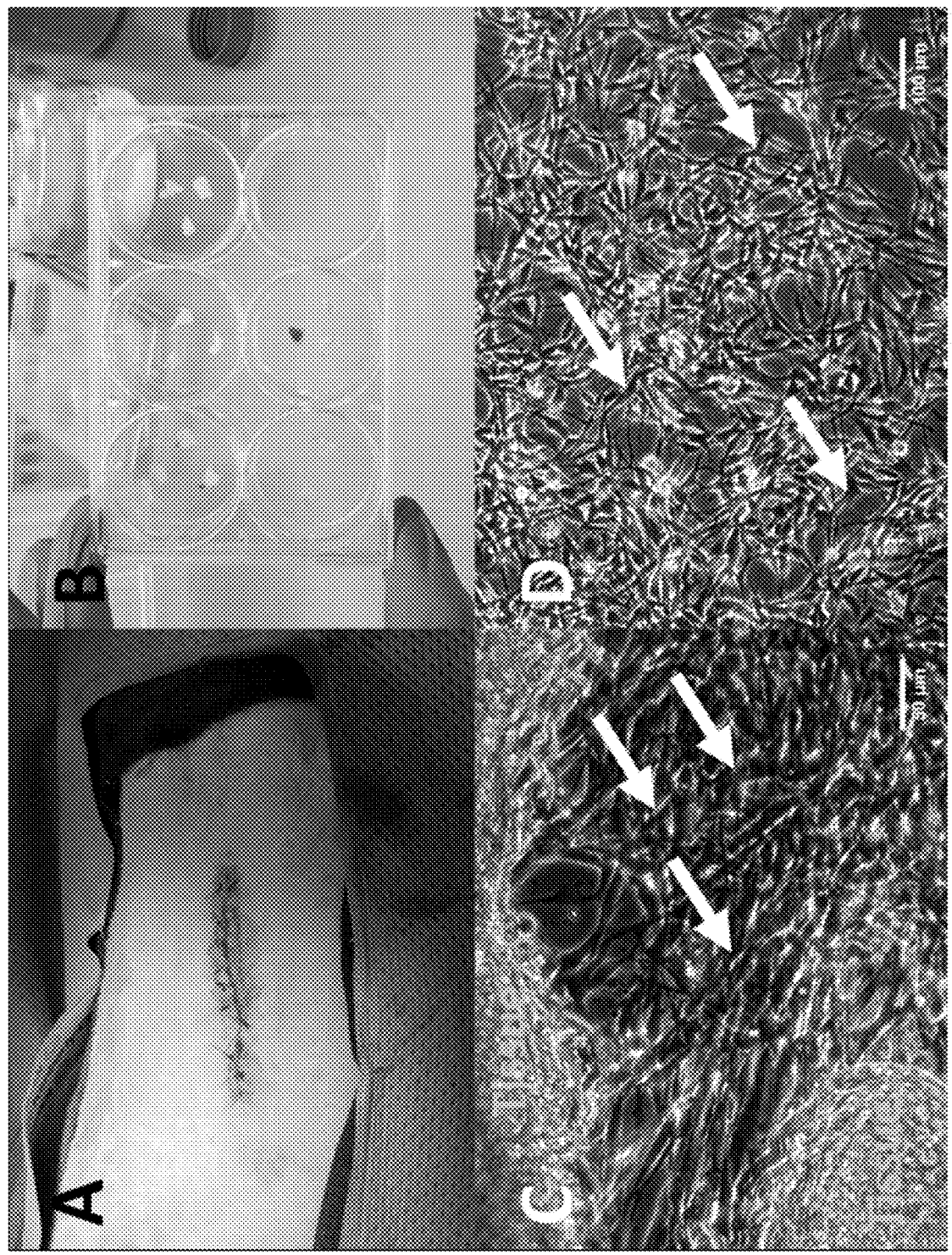
FIG. 7. Tissue harvesting and cell extraction/expansion. (A) the location of the jugular vein extraction from the animal's neck; (B) the minced jugular vein tissues cultured on a Petri dish are shown by black arrows; (C) the migrated cells from tissues after 5 days in an incubator; (D) the migrated and proliferated cells in a sterilized Petri dish after 5 days are shown by white arrows. The scale bars are 50 and 100 μm in (C) and (D), respectively.

Tissue Harvesting and Cell Extraction/Expansion:

A 2 to 3 cm section of the jugular vein was surgically removed from a juvenile castrated male sheep (FIG. 7, A) under anesthesia in a sterile condition at the UCI Medical Center, according to the IACUC protocol#2012-3071. After full recovery, the sheep was transferred to the animal care facility up to three weeks to have the cultured H-TEHV ready for implantation. The harvested tissue was immediately transferred to our cell culture lab at the UCI's Edwards Lifesciences Center for further processing. Upon arrival, the jugular vein was minced under a sterile cell culture hood, and carefully washed by sterilized PBS 1× to remove blood clots and clumps from the vein tissue. The tissue clusters then were cut to 5 mm×5 mm segments and transferred to a sterilized petri dish (FIG. 7, B). The dish was kept in the hood for 30 minutes to allow the tissue fragments attach to the top of the petri dish. After 30 minutes, the preheated, enriched cell culture media, along with endothelial cells/ smooth muscle cells/fibroblasts growth factors (4 ml medium for each well), were gently added to each petri dish well (FIG. 7, B). The petri dish was kept in a 37° C. incubator for a week with the medium being replaced in 50% volume with preheated fresh medium every day. After 5 days, the cells migrated out of the tissue fragments, as confirmed under the microscope (FIG. 7, C). Later, we let the cells proliferate in the incubator to achieve 5 million cells for the H-TEHV tissue culture (FIG. 7, D). Finally, the cells were trypsinized for sorting and characterization as follows.

Cell Sorting and Characterization:

The trypsinized cells were quantitatively sorted according to the method described by Weber et al. (Weber, S. C., et al., *Isolation and Culture of Fibroblasts, Vascular Smooth Muscle, and Endothelial Cells From the Fetal Rat Ductus Arteriosus*. Pediatr Res, 2011. 70(3): p. 236-241), which magnetically labels the extracted cells and sorts them based on Magnetic-Activated Cell Sorting (MACS). Applying both positive and negative selections, the method has been used for cell isolation. The cell sorting has two steps. In the first step, we isolated the vascular endothelial cells. The extracted cells were incubated with CD31 antibody (0.1 mg/ml CD31 Antibody-IgG2a, Bio-Rad Laboratories Inc., Hercules, Calif.), which specifically targets endothelial cells, at 20° C. for 30 minutes. The cells treated with CD31 antibody were incubated with coated magnetic microbeads (Anti-Mouse IgG, No. 130-048-402; Miltenyi Biotec, Bergisch Gladbach, Germany) at 4° C. for 15 minutes. Then, these conjugated endothelial cells were isolated and removed by a magnetic column (positive selection). The remaining cells, a mixture of SMCs and fibroblasts, were collected in separated cell culture Petri dishes. In all cell culture procedures, the endothelial cells were fed with Endothelial Cell Growth Medium (EGM-2 Bulletkit CC-3162, Lonza, USA), and the mixture of SMCs/fibroblasts were fed with mixture of 50% SmGM-2 Smooth Muscle Growth Medium (SmGm-2 Bullekit CC-3182) and 50% FGM Fibroblast Growth Media (FGM-2 Buiiekit CC-3132, Lonza Group, Basel, Switzerland).

H-TEHV Tissue Culture:

Using a mandrel apparatus made of biocompatible PEEK, the tri-leaflet H-TEHV was developed by casting collagen solution mixed with SMC/FB layer and covered by endothelial cells over the tri-leaflet Carbothane mesh scaffold (FIG. 5, (B) and C). The mandrels are used for shaping and securing cells and tissue layers as they grow in three dimensions to form a heart valve. As shown in Figure (B) and (C), the mandrel apparatus includes two different components that secure the combination of scaffold and the enclosing tissue layers. Cells mixed with collagen were injected over the scaffold and assembled with the upper component of the mandrel. The mandrel apparatus provides the ability to adjust the space between its two components so that different cell types and tissue layers can be accommodated in time steps. First, the Carbothane scaffold was sterilized with 70% ethanol and coated with 1 µg/ml concentration of Fibronectin solution. The mixture of SMCs/fibroblasts (5 million cells) was uniformly mixed with Collagen type I (RatCol Rat Tail Type I collagen 4 mg/ml, Advanced BioMatrix, Carlsbad, Calif.) and then injected over the scaffold using the mandrel apparatus as shown in FIG. 5, C. The scaffold within the apparatus was kept in an incubator at 37° C. for 1.5 hours with no cell culture media to complete coating the top and bottom of the H-TEHV's scaffold by the mixture of SMCs/fibroblast (the first layer in FIG. 5, A). Then, the H-TEHV was transferred into a sterile Petri dish with the mixture of 50% SmGM-2 and 50% FGM-2 media and kept in the incubator. After two-day incubation, the second layer consisting of endothelial cells was cultured over the first layer at the top and bottom of the valve's scaffold. To do so, the valve scaffold with the first layer was washed with Dulbecco's Phosphate Buffered Saline—DPBS 1× and placed back between the sterile PEEK mandrels, and then the endothelial cells (0.5 million cells) mixed with collagen type I (RatCol Rat Tail collagen type I 4 mg/ml, Advanced BioMatrix, Carlsbad, Calif.) were injected into the H-TEHV using the mandrel apparatus. Afterwards, the H-TEHV was incubated for 1.5 hours at 37° C. with no cell culture media to complete culturing the second layer (the second layer in FIG. 8, A). The H-TEHV was separated from the mandrel apparatus and transferred into a sterile petri dish with the mixture of media (50% endothelial cell growth medium, 25% smooth muscle growth medium and 25% fibroblast growth media). The top and bottom side views of the developed H-TEHV were shown in FIGS. 8, (B) and (C). The developed H-TEHV was daily fed with a fresh mixture of media (50% endothelial growth media, 25% smooth muscle growth media and 25% fibroblast growth media) up until the implantation day.

Durability of the H-TEHV's Scaffold:

At the end of 50 million cycles in AWT system, no defect were found over the Carbothane valve leaflets, at the commissures between the leaflets, at the valve posts, on the sutures, or at the sewing ring.

Figure 8:
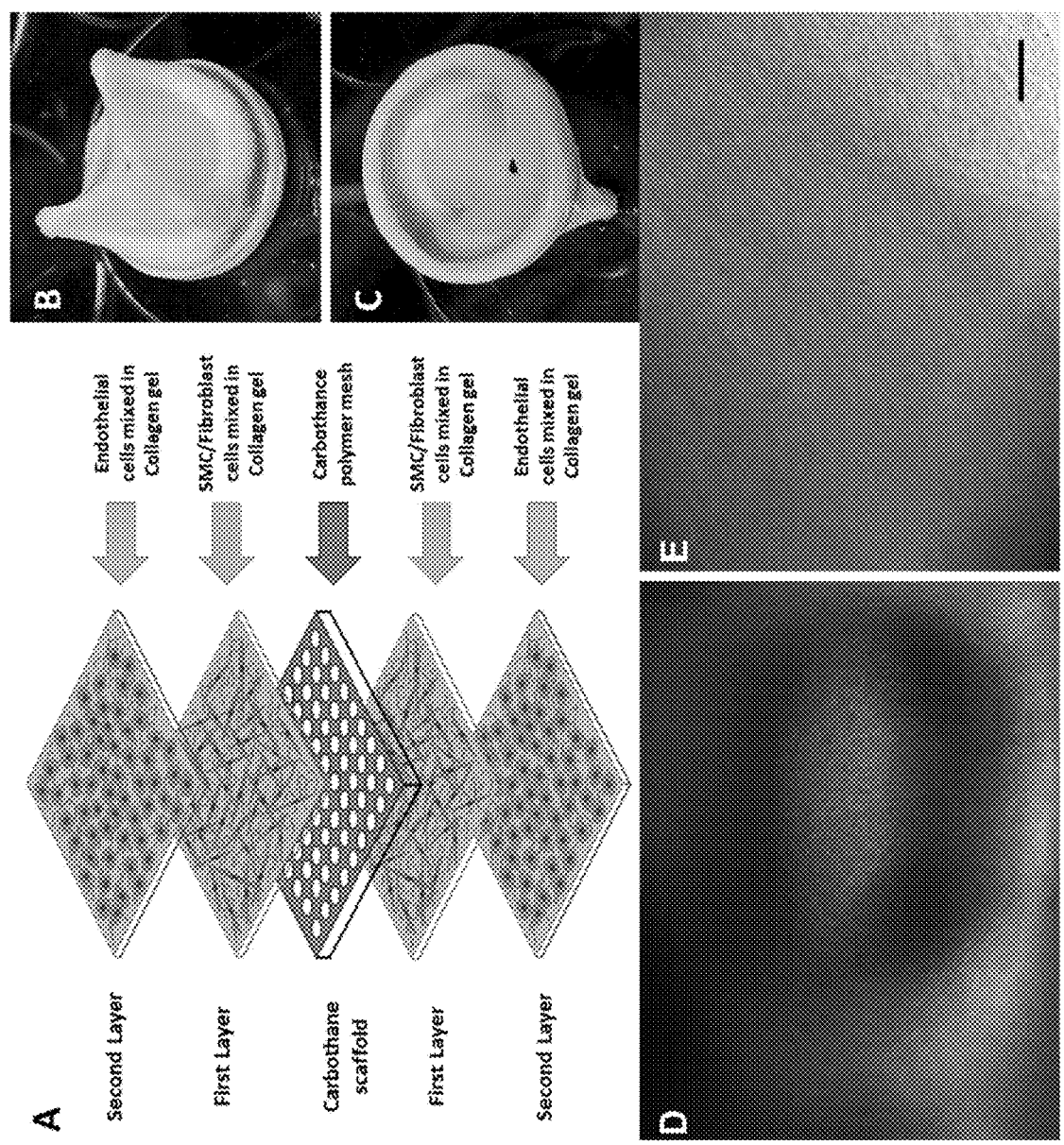
FIG. 8. (A) Coating of the top and bottom of a H-TEHV scaffold by a mixture of SMCs/fibroblasts (first layer) and then with a layer of endothelial cells (second layer). (B) top view; and (C) bottom view. (D) and (E) have been captured by a light microscope to show the elongated cells (the mixture of Smooth Muscle Cells and Fibroblasts) in the first layer of tissue grown over the valve scaffold. (D) shows the status of the elongated cells (very small dark stains in the image) around the mesh scaffold (the holes on the valve scaffold). The big black circle in the middle of the (D) is one of the holes of the valve scaffold. (E) shows elongated cells at the edge of the valve scaffold. The very small dark stains in the image are cells, which have been elongated in collagen.

H-TEHV for Surgical Implantation:

The H-TEHV development was completed in three weeks with all tissue layers successfully grown on the valve scaffold. FIG. 8, A schematically shows the tissue layers on both sides of the Carbothane scaffold. No defect was not found in the tissue. The elongated cells were observed in tissue layers. We found that the thickness of the cultured valve's leaflets did not exceed a natural leaflet's thickness (~0.6 mm) prior to implantation. The tissue of the developed H-TEHV was observed and monitored prior the day of the valve implantation.

Figure 9:
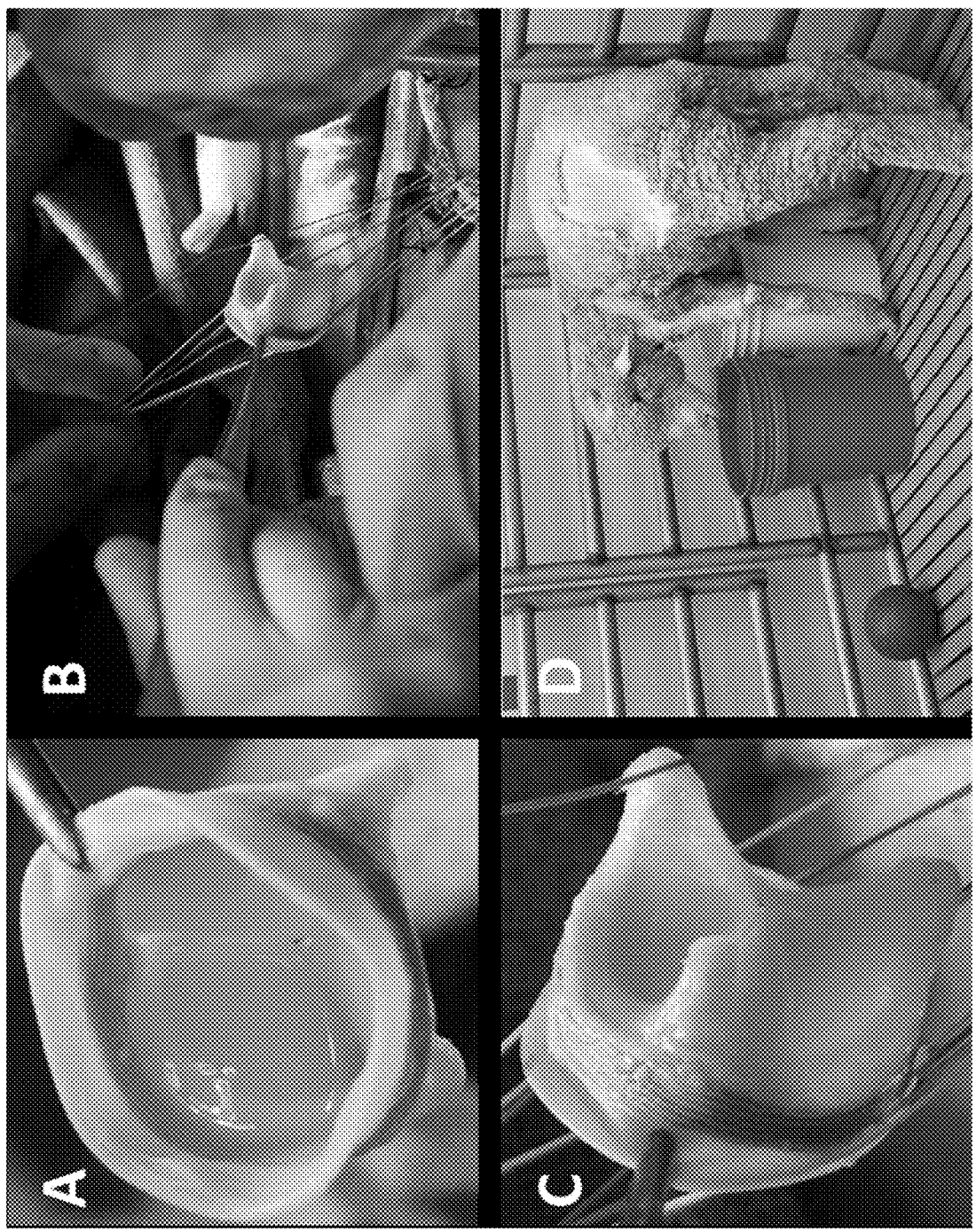
FIG. 9. Surgical implantation of H-TEHV in the sheep mitral position. (A) H-TEHV ready for implantation, (B) H-TEHV being guided into position, (C) enlarged view of being guided into position, (D) Sheep recovering after successful surgery.
Figure 10:
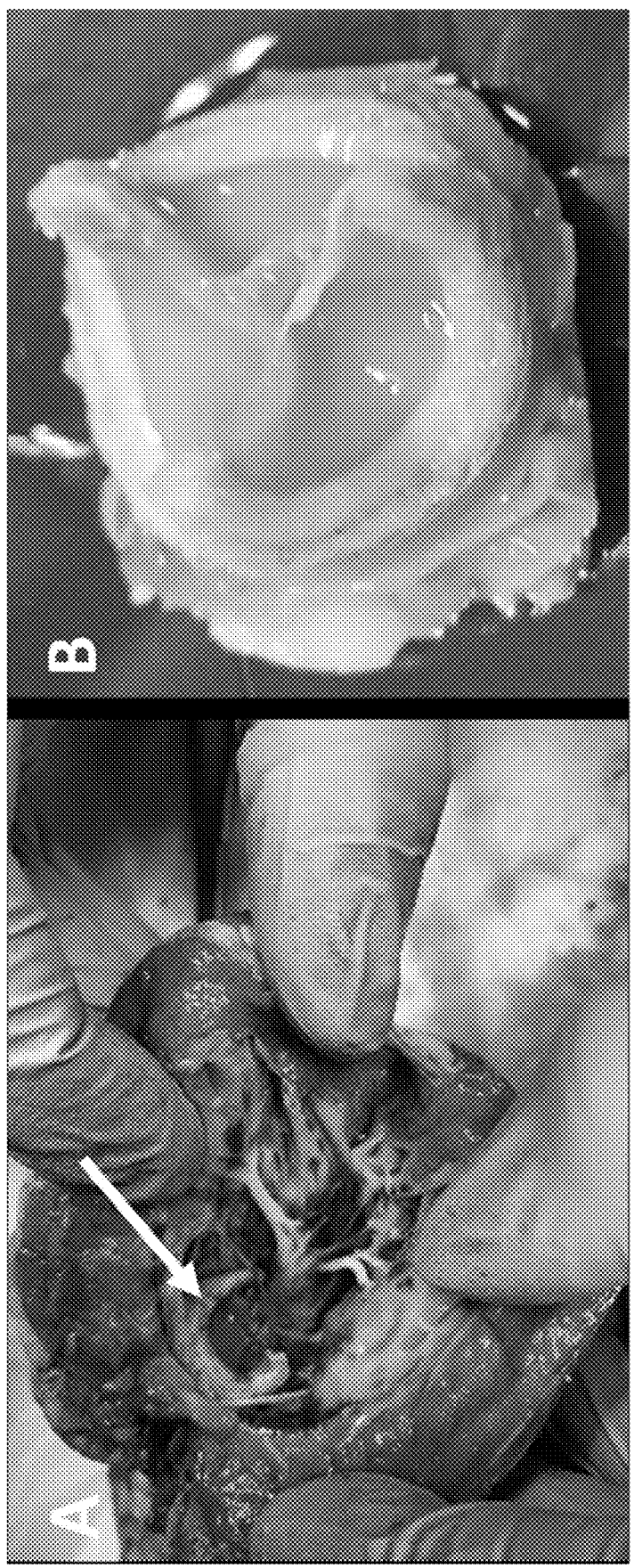
FIG. 10. Post-mortem study: (A) Lack of any tissue dehiscence, (B) H-TEHV remained intact.

Surgical Implantation of H-TEHV in the Sheep's Mitral Position:

Three weeks after extraction of the jugular vein, the H-TEHV was implanted in the same sheep's mitral position through a midsternal thoracotomy using a heart-lung bypass machine under the control of a perfusion team. The surgical procedure was performed according to IACUC protocol#2012-3071 on Sep. 12, 2017. The open-heart surgery was successfully led by Prof. Jeffrey Millikan and our surgical and perfusion teams at UCI Medical Center (FIG. 9). After completion of surgery, the animal was recovered from anesthesia and transferred on his feet to UCI vivarium without any sign of stroke or other surgery-related problems (FIG. 9, D). The animal expired eight hours after being transferred to the vivarium. The cause of death was determined due to pulmonary edema. Post-mortem studies showed that the H-TEHV remained intact without any tissue dehiscence (FIG. 10). The tissue at the leaflet's belly and edge is not detached from the valve scaffold and was not washed off by blood flow.

Figure 11:
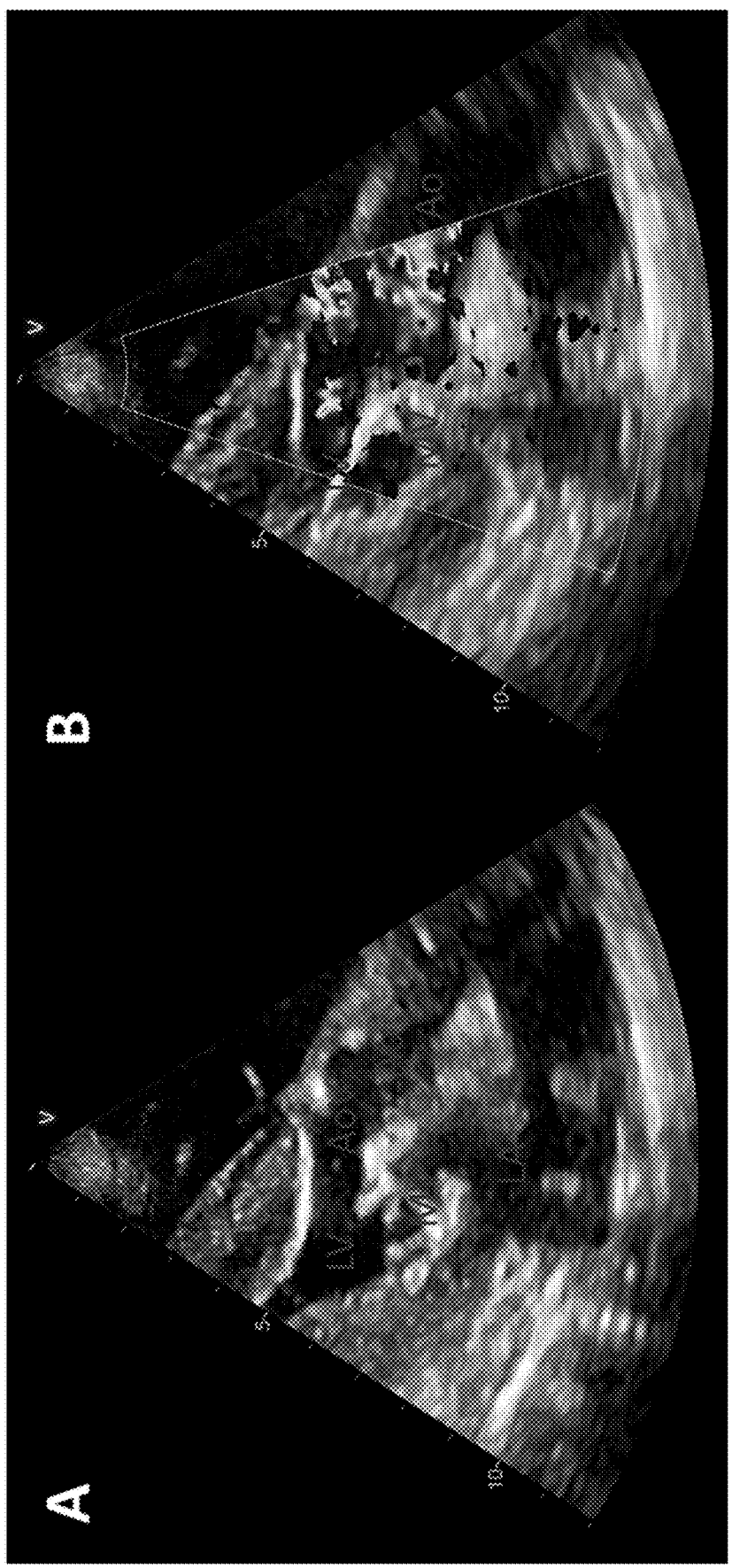
FIGS. 11. (A) and (B) Dopler analysis shows that the H-TEHV has no regurgitation during function.

Echocardiographic Assessment:

The implanted H-TEHV was comprehensively monitored by echocardiography. GE Vivid E9 echocardiography system (GE Healthcare, Milwaukee, Wis.) and a 4VD ultrasound transducer were used in the surgery room. After the implantation of H-TEHV, favorable mobility of the leaflets was confirmed according to B-mode. The color Doppler study showed that the competent H-TEHV have no regurgitation (FIG. 11). According to B-mode echocardiography, the valve leaflet mobility was favorable, and no restriction in leaflet mobility was observed. The color Doppler study showed that the competent H-TEHV with no apparent regurgitation (FIG. 11).

Discussion

Eliminating the need for lifelong anticoagulation medication without compromising durability will significantly improve the quality of life of younger patients in need of a heart valve replacement. The H-TEHV aims to overcome the traditional disadvantages of both bioprosthetic and mechanical heart valves by mimicking a native valve's biocompatibility and hemodynamics while maintaining adequate strength and durability similar to mechanical valves. H-TEHV is a particularly desirable solution for patients younger than 65 who may not receive BHVs due to the chance of reoperation, and prefer to avoid the risks of bleeding and stroke due to anticoagulant medications needed for mechanical valves that limit their active personal and professional lives. Because heart valve replacement surgery is an elective procedure, most patients can wait for about three weeks to have their autologous hybrid TEHV created.

This study is the first of its kind that test the feasibility of the H-TEHV in vivo. Although we lost the animal after eight hours, our post-mortem studies did not reveal the cause of death to be directly related to the function of the H-TEHV. Our major concern at the time of the study was whether the cultured tissue embolizes into the animal's organ. However, the fact that the animal was able to walk on his feet, curtails the possibility of a stroke. The post-mortem studies showed that the valve remained totally intact after eight hours of continuous function in the sheep with no tissue separation or dehiscence. Further, we did not find any trace of embolization anywhere in the animal.

In conclusion, we successfully developed and implanted a novel hybrid TEHV in sheep. We showed that the H-TEHV can withstand the high-pressure conditions to which exposed at the mitral position without any shrinkage or valve decomposition in short term. Keeping animals alive up to twenty weeks to test the H-TEHVs' performance and durability in chronic situations will require improving our post-surgical animal care to avoid mortality and/or morbidity situations that are not directly related to the H-TEHV performance.

We have demonstrated the development and implantation of an autologous hybrid tissue engineered heart valve (H-TEHV). The H-TEHV overcomes traditional disadvantages of mechanical and bioprosthetic heart valves by mimicking a native valve's biocompatibility and hemodynamics while maintaining adequate strength and durability. The H-TEHV is a desired solution for patients younger than 65 who may not receive bioprosthetic valves due to the chance of durability concerns, while preferring to avoid the risks of bleeding and stroke due to anticoagulant medications needed for mechanical valves, which limit their active personal and professional lives.

EXAMPLE 2

Development of a Bioinspired, Hybrid, Bileaflet Mitral TEHV and Optimization of its Hemodynamics In Vitro.

Bileaflet mitral H-TEHVs are developed in vitro by creating cell layers tightly enclosing the leaflets of a bioinspired valve scaffold made of thermoplastic polyurethane mesh. The scaffold's entire surface is covered with a layer of living fibroblasts and functional endothelium to prevent thromboembolic events. Mitral valves, developed in different sizes, and with different aspect ratios, can be implanted in our heart flow simulator to test whether they produce better hemodynamics compared to standard trileaflet valves.

The Hybrid TEHV:

We originally introduced the H-TEHV by enclosing a surface-modified superelastic Nitinol mesh scaffold in valve-like living tissue. We used thin acid-etched flat Nitinol leaflets (25-micron thickness), sewn into a trileaflet valve as the scaffold and sequentially cultured three layers of cell types (i.e., human smooth muscle cells (SMCs), human fibroblast/myofibroblast cells, and human umbilical vascular endothelial cells) mixed with collagen gel to fulfill the role of valvular interstitial cells (VICs), and valvular endothelial cells, respectively (Alavi S H, Kheradvar A. A hybrid tissue-engineered heart valve. *The Annals of thoracic surgery.* 2015; 99:2183-2187; Alavi S H, Kheradvar A. Metal mesh scaffold for tissue engineering of membranes. *Tissue Engineering Part C: Methods.* 2012; 18:293-301; and Alavi S H, Liu W F, Kheradvar A Inflammatory response assessment of a hybrid tissue-engineered heart valve leaflet. *Ann Biomed Eng.* 2013; 41:316-326). Equivalent cellular phenotypes were present in the ventricularis, fibrosa, and spongiosa layers of native heart valves (Della Rocca F, Sartore S, Guidolin D, Bertiplaglia B, Gerosa G, Casarotto D, Pauletto P. Cell composition of the human pulmonary valve: A comparative study with the aortic valve—the vesalio* project. *The Annals of thoracic surgery.* 2000; 70:1594-1600). The cells were seeded in sequence on the scaffold, comprised of a mesh enclosed by bovine type I collagen gel mixture. Our study has been published in the *Annals of Thoracic Surgery* (Alavi S H, Kheradvar A. A hybrid tissue-engineered heart valve. *The Annals of thoracic surgery.* 2015; 99:2183-2187), and received a news release from the *Society of Thoracic Surgeons.* We follow the same general concept for hybrid tissue culture with some changes related to distribution and composition of fibroblasts (FBs) and SMCs, and use a biocompatible elastomer with proven durability, as the valve scaffold.

Figure 12:
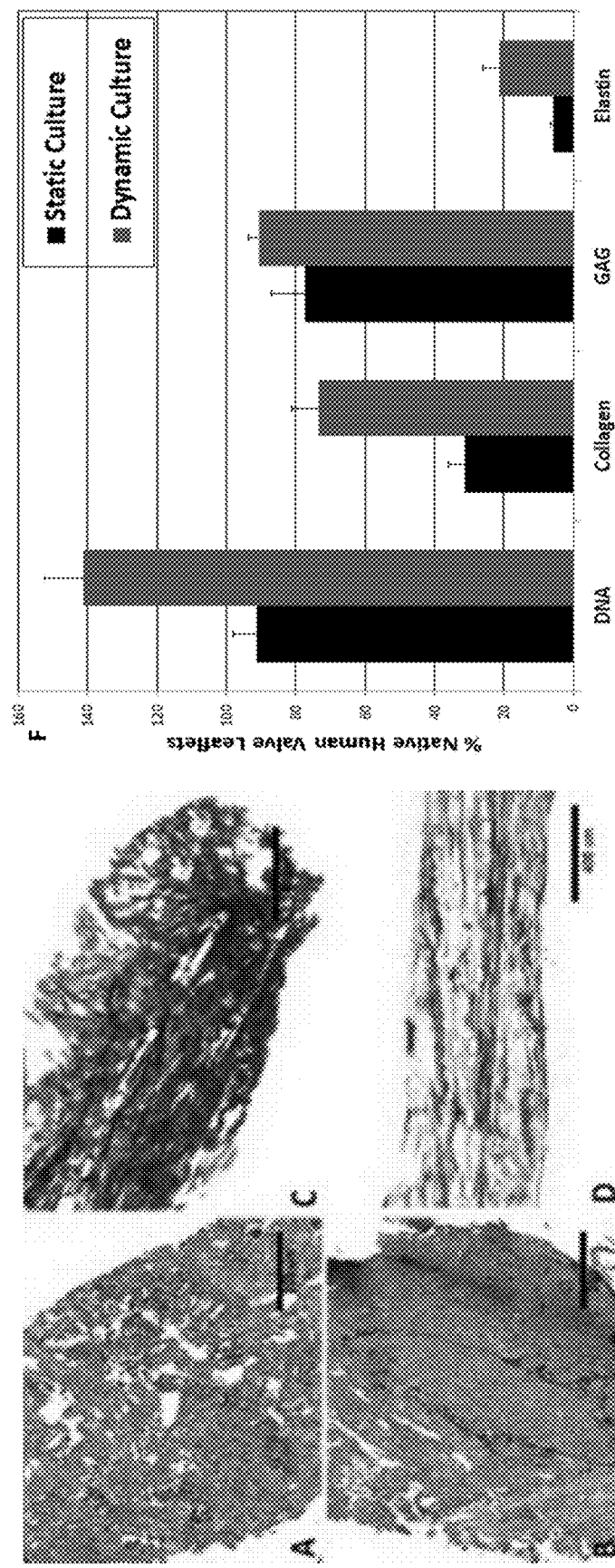
FIG. 12. Qualitative histology performed on hybrid tissue leaflets. H&E staining showed a spongy structure for a statically-conditioned group (A) vs. a dense composition for a dynamically-conditioned group (B). (C) SRS staining showed that the mesh is completely enclosed within the tissue. (D) Shows a fibrous structure with a uniform cellularity throughout the leaflets. (F) Quantitative biochemical assays comparing both groups showed an increase in DNA content and matrix proteins values for dynamic group. Alavi and Kheradvar, Annals of Thoracic Surgery (2015), 99(6): 2183-2187.

Leaflet Tissue Analysis:

To analyze the H-TEHV's extracellular elements, biochemical assays were performed, and the total DNA was considered as an indicator of cell numbers based on the Hoechst dye method (Cesarone C, Bolognesi C, Santi L. Improved microfluorometric DNA determination in biological material using 33258 hoechst. *Analytical biochemistry.* 1979; 100:188-197). Hydroxyproline as the total collagen content was quantitatively determined (Bergman I, Loxley R. Two improved and simplified methods for the spectrophotometric determination of hydroxyproline. *Analytical Chemistry.* 1963; 35:1961-1965). Total proteoglycan (GAG), was measured with a slight modification to the method developed by Farndale et al. (Farndale R W, Buttle D J, Barrett A J. Improved quantitation and discrimination of sulphated glycosaminoglycans by use of dimethylmethylene blue. *Biochimica et Biophysica Acta (BBA)—General Subjects.* 1986; 883:173-177), and a FASTIN assay (Biocolor), was used to quantify elastin content. H&E staining was performed on the edges of the hybrid tissues for general morphology. Histology was performed on the mid-parts (i.e., the areas that contain the mesh) using a state-of-the-art laser microtome (LLS Rowiak, Hannover, Germany; FIG. 12). The leaflets were then stained by SRS for general morphology and light green to demonstrate collagen components (FIG. 12). The DNA content was found comparable to that of the native valve tissue in static groups (p~0.15), with an increase to ~140% in dynamically-conditioned tissues. ECM production increased with dynamic culture, with a significant increase (p<0.05), for collagen. H&E staining showed a uniform organized structure with a spongy form for static groups (FIG. 12, A), and a denser shape for dynamic groups (FIG. 12, B). SRS at the tip of the leaflet with the mesh tightly enclosed within the tissue is shown in FIG. 12, C. The light green section at the mid-part of the leaflet (FIG. 12, D) shows a fibrous collagenous structure with smooth inflow and outflow sides (Alavi S H, Kheradvar A. A hybrid tissue-engineered heart valve. *The Annals of thoracic surgery.* 2015; 99:2183-2187). These data indicate that a dense tissue with similar microscopic characteristics of the valve leaflets was formed.

Figure 13:
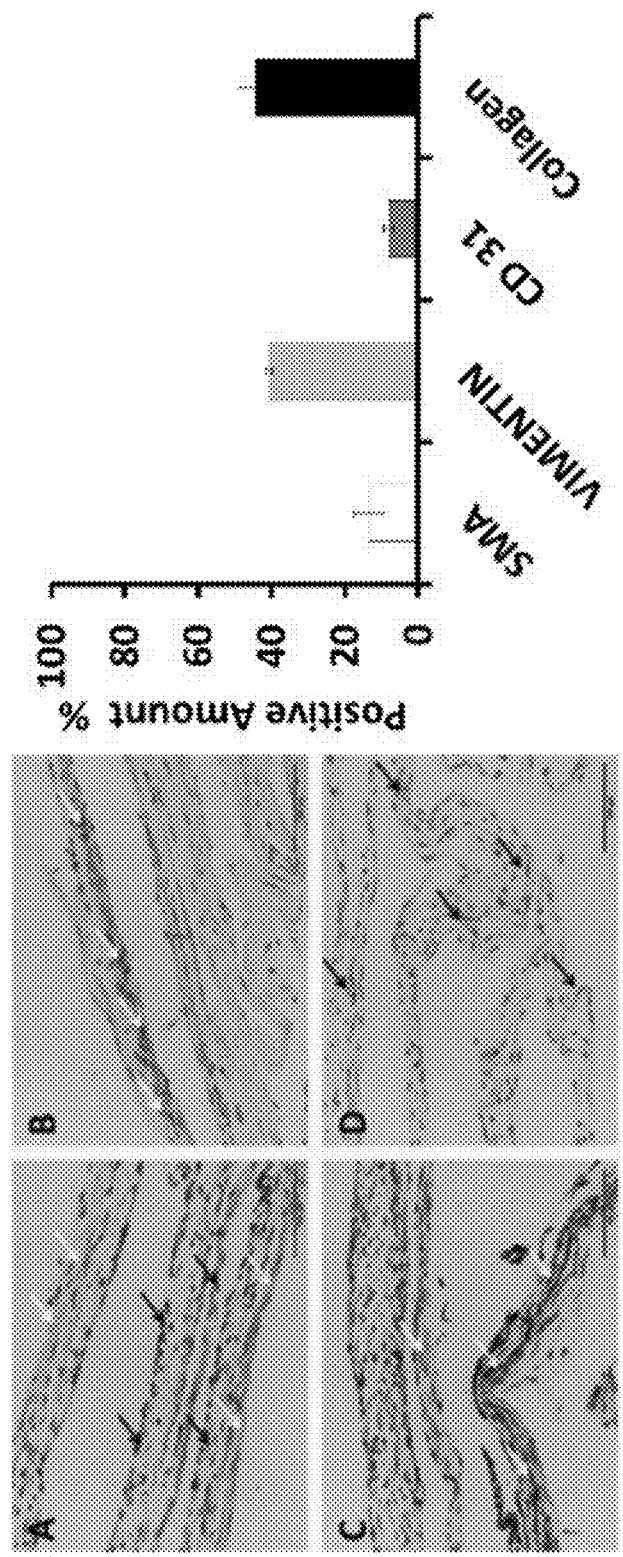
FIG. 13. (Left) IHC staining and quantitative analyses of the cross-sections of H-TEHV's leaflet after 3-week culture in vitro show that the formation of the hybrid tissue. (A) Trichrome staining shows the tissue's ECM. The reddish and bluish areas pointed with black and white arrows represent cells and collagen fibrils, respectively. (B) α-SMA staining shown as brownish areas indicates SMCs in the first layer. (C) Vimentin was expressed indicating the presence of fibroblasts. The brownish area is shown by white arrows. (D) CD31 staining shows endothelial cells (black arrows). (right) Percentage of each cell type and collagen were quantitively calculated and shown.

Tissue Generation and Cellular Characterization:

After three weeks, Immunohistochemistry (IHC), staining was performed on the cross-sections extracted from the segments of cultured hybrid tissue. IHC was performed to test whether these cell layers properly exist on the tissue. IHC identified three different cell lines of SMCs, FBs, and endothelial cells, with the percentage of each cell type quantitatively measured (FIG. 13).

Figure 14:
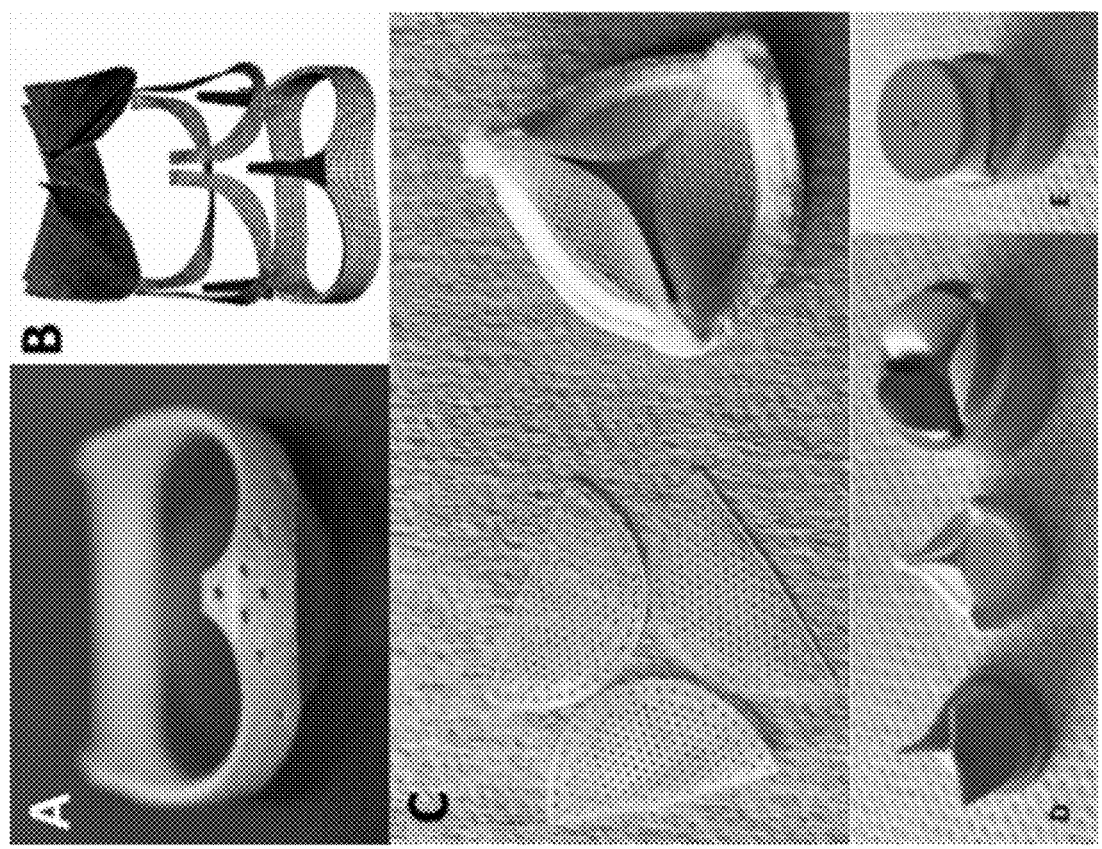
FIG. 14. Trileaflet valve scaffolds made based on the computational modeling. (A) valve frame made of 3D printed titanium; (B) Valve scaffold assembly; (C) Valve leaflets made of Carbothane mesh (left) sewn into a trileaflet valve (right). Valve frames are covered with surgical fabric for sewing them inside the heart. (D) Mandrels for growing H-TEHVs. (E) A valve scaffold inside the PEEK mandrel apparatus.

Hybrid Scaffold Development:

For the first time, we have used leaflets made of Carbothane (AC-4095A), a thermoplastic polyurethane (TPU). Previously, we designed and developed trileaflet scaffolds by combining three meshed leaflets and a valve frame made of a 3D printed titanium, as shown in FIG. 14. The H-TEHVs were prepared by casting collagen solution mixed with cells of each layer around the trileaflet Carbothane scaffold using an apparatus made of biocompatible PEEK (FIG. 14).

Figure 15:
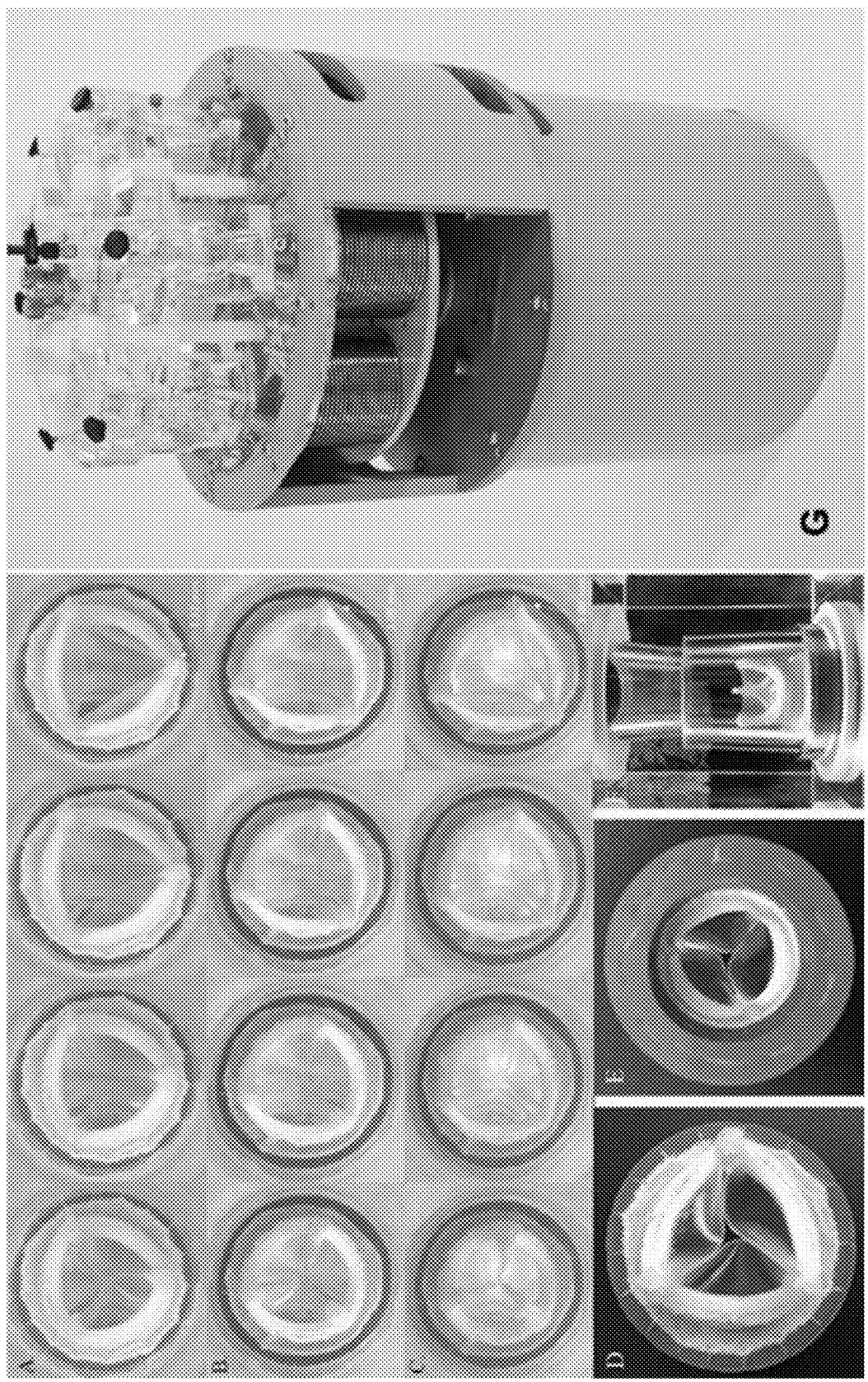
FIG. 15. Carbothane scaffolds in AWT system for durability. (A-C) Comparison of the valve scaffolds' function in an accelerated wear testing system at different closing pressures. (D) Scaffold top view; (E) Scaffold' bottom view; (F) Scaffold side view inside the AWT chamber; (G) M6 AWT system.

Durability Testing in an Accelerated Wear Test (AWT) System:

We previously tested the trileaflet Carbothane valve scaffold in our AWT system (M6 Heart Valve Durability Tester, Dynatek Labs, Galena, Mo.), according to ISO-5840. FIG. 15 shows the AWT system with trileaflet Carbothane valve scaffolds mounted to them. Those valve scaffolds have already passed 50M cycles without any macroscopic or microscopic defect. We also use a bileaflet scaffold exclusive for the mitral position, and test the scaffold's durability in an AWT system.

Figure 16:
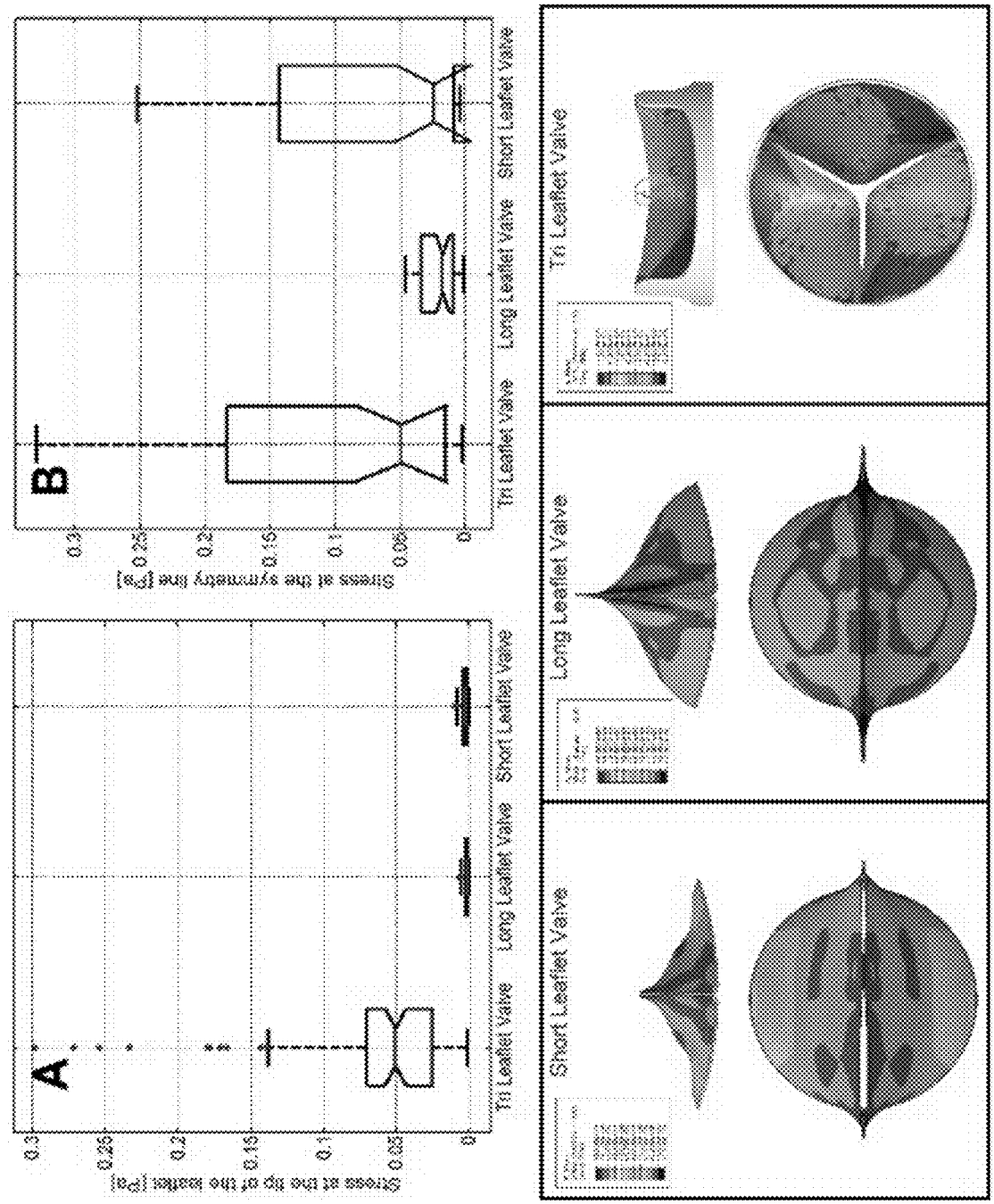
FIG. 16. (Top) Box plots of the stress distribution over the leaflets (A) at the leaflet tip (B) at the line leaflet symmetry, shows significantly lower stresses in bileaflet vs. trileaflet valves. (Bottom) Comparison of Von Mises stress distribution over the leaflets in bileaflet valves vs. trileaflet valve show that the leaflet stress is significantly damped by dynamic saddle annulus in bileaflet valves. From Kheradvar and Falahatpisheh, *J Heart Valve Dis* 2014.

Bio-Inspired Bileaflet Mitral Valve with a Dynamic Saddle-Shaped Annulus Minimizes the Stress Over the Leaflets:

The mitral valve is a unique valvular structure whose number of leaflets and dynamic saddle-shaped annulus distinguish it from other heart valves. While the mitral valve's unique characteristics have been extensively identified and studied during the past (Jimenez J H, Soerensen D D, He Z, He S, Yoganathan A P. Effects of a saddle shaped annulus on mitral valve function and chordal force distribution: An in vitro study. *Ann Biomed Eng.* 2003; 31:1171-1181; Ryan L P, Jackson B M, Enomoto Y, Parish L, Plappert T J, St. John-Sutton M G, Gorman R C, Gorman Iii J H. Description of regional mitral annular nonplanarity in healthy human subjects: A novel methodology. *J Thorac Cardiovasc Surg.* 2007; 134:644-648; Karlsson M O, Glasson J R, Bolger A F, Daughters G T, Komeda M, Foppiano L E, Miller D C, Ingels N B, Jr. Mitral valve opening in the ovine heart. *Am J Physiol Heart Circ Physiol.* 1998; 274:H552-563; Salgo I S, Gorman J H, III, Gorman R C, Jackson B M, Bowen F W, Plappert T, St John Sutton M G, Edmunds L H, Jr. Effect of annular shape on leaflet curvature in reducing mitral leaflet stress. *Circulation.* 2002; 106:711-717 and Carlhall C, Wigstrom L, Heiberg E, Karlsson M, Bolger A F, Nylander E. Contribution of mitral annular excursion and shape dynamics to total left ventricular volume change. *Am J Physiol Heart Circ Physiol.* 2004; 287:H1836-1841), none of these characteristics have been incorporated into development of mitral valve prosthetics. We have previously developed a bi-leaflet mitral bioprosthesis that mimics the motion of the mitral valve's saddle annulus (Kheradvar A. Implantable prosthetic valves and methods relating to same. 2014; and Kheradvar A, Falahatpisheh, A. The effects of dynamic saddle annulus and leaflet length on transmitral flow pattern and leaflet stress of a bi-leaflet bioprosthetic mitral valve. *J Heart Valve Dis.* 2012; 21:225-233). Our studies show that the stress distributions at the tip of the leaflets during systole are overall much smaller than the stress generated over the annulus in bileaflet prototypes when compared to standard trileaflet bioprosthetic valves that have a rigid annulus (FIG. 16). This reduction of stress is because mitral annulus deflection during valve opening and closure dampens the hemodynamic load exerted over the valve (Kheradvar A, Falahatpisheh, A. The effects of dynamic saddle annulus and leaflet length on transmitral flow pattern and leaflet stress of a bi-leaflet bioprosthetic mitral valve. *J Heart Valve Dis.* 2012; 21:225-233). Therefore, the annulus motion prevents the leaflet from exposure to excessive tensile stress, as evidenced by the Von Mises stress, whose magnitude is larger around the annulus, as shown in FIG. 16. Achieving lower stress magnitudes at the leaflet minimizes the risk of calcification, and helps to improve the valve's durability.

Bio-inspired, bileaflet H-TEHVs in the mitral position provide improved function and hemodynamics over the H-TEHVs with typical trileaflet design.

Development of Bileaflet Carbothane Scaffold with Dynamic Saddle-Shaped Annulus:

Carbothane AC-4095A (Lubrizol, Inc.; hardness shore A 95), is a biocompatible thermoplastic polyurethane with mechanical properties that makes it an ideal candidate for heart valve scaffold material due to its combination of flexibility and durability. Since Carbothane is shown to have a relatively low propensity to calcify, it is an appropriate material for cardiovascular implants such as in total artificial heart (Yang M, Zhang, Z., Hahn, C., King, M. W., Guidoin, R. Assessing the resistance to calcification of polyurethane membranes used in the manufacture of ventricles for a totally implantable artificial heart. *J Biomed Mater Res.* 1999; 48:648-659). Its tensile strength of 68.9 MPa and its elastic modulus of 74.5 MPa closely approximate the values found in native valves' (Hasan A, Ragaert K, Swieszkowski W, Selimović Š, Paul A, Camci-Unal G, Mofrad M R K, Khademhosseini A. Biomechanical properties of native and tissue engineered heart valve constructs. *Journal of biomechanics.* 2014; 47:1949-1963).

Figure 17:
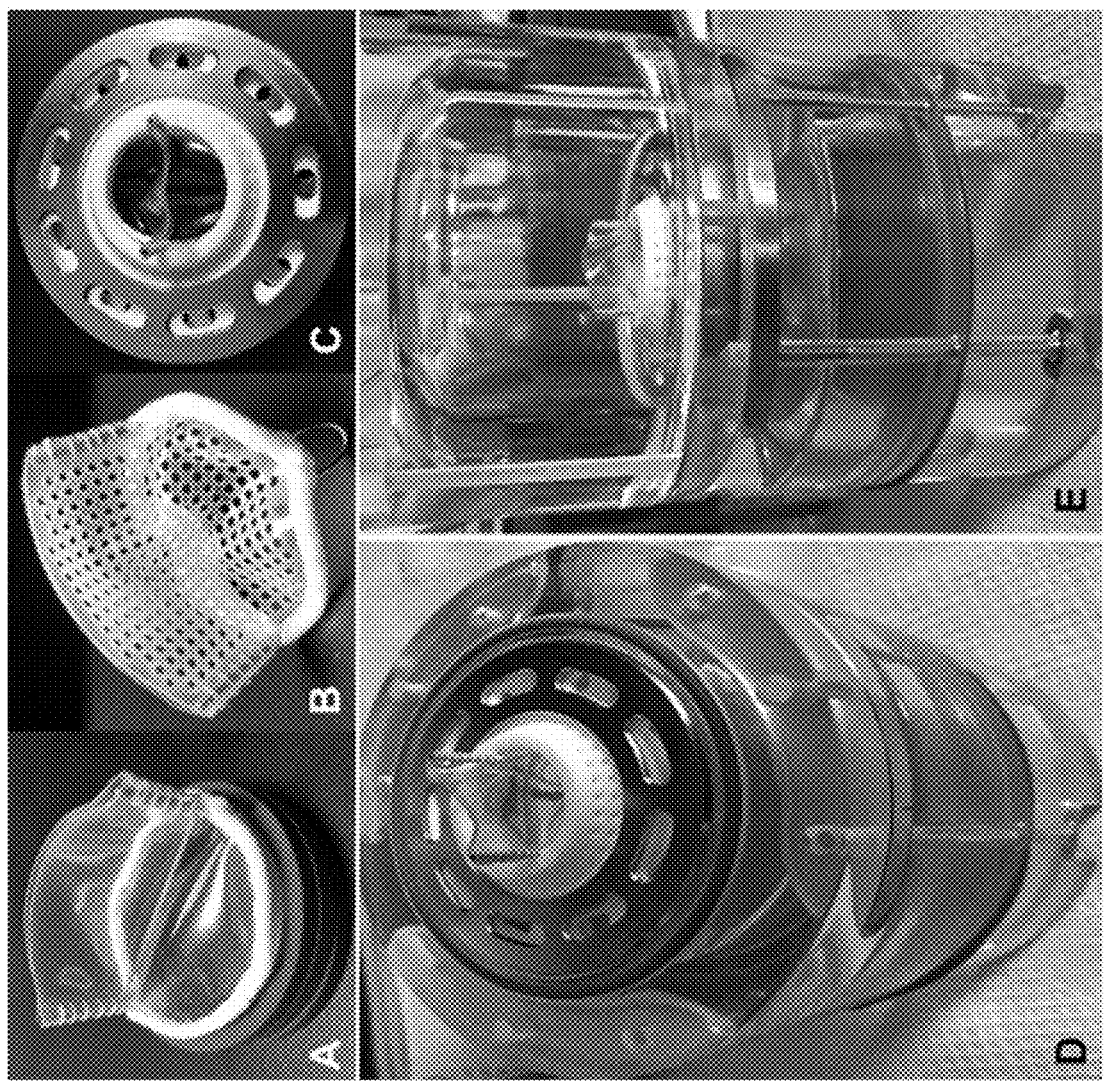
FIG. 17. Preliminary prototypes of the bileaflet Carbothane mitral valves with dynamic saddle-shaped annulus. (A) A version with flat (unmeshed) leaflet for durability and hemodynamic test purposes; (B) a meshed version to test suitability for tissue culture, both developed at Kheradvar Lab. (D) and (E) show Carbothane valves mounted on the Aptus Physio Bioreactor at Simionescu lab for additional testing.

To produce the Carbothane mesh leaflets, a thin layer of the material is laser-cut and checked under the microscope to confirm that the leaflet edges are smooth and not burned due to excessive heat. The bileaflet frame is made of superelastic Nitinol wires with 8% strain recovery shaped into a saddle-shaped annulus with two prongs for attaching and holding the leaflets (Kheradvar A, Falahatpisheh, A. The effects of dynamic saddle annulus and leaflet length on transmitral flow pattern and leaflet stress of a bi-leaflet bioprosthetic mitral valve. *J Heart Valve Dis.* 2012; 21:225-233). The leaflets and the saddle-shaped annulus are also sutured to each other by means of two Nitinol supporting prongs that are extended from the annulus alongside the leaflets (FIG. 17). The supporting prongs act like native mitral valve's chordae tendineae, preventing the leaflets from being prolapsed toward the atrium. All the frames are covered with and connected to the leaflets by biocompatible polyester surgical fabrics. Accordingly, the bileaflet Carbothane scaffold with dynamic annulus was developed and its leaflet lengths have been optimized by finite element modeling, to minimize stress distribution over the leaflets. Example embodiments are shown in FIG. 17.

Figure 18:
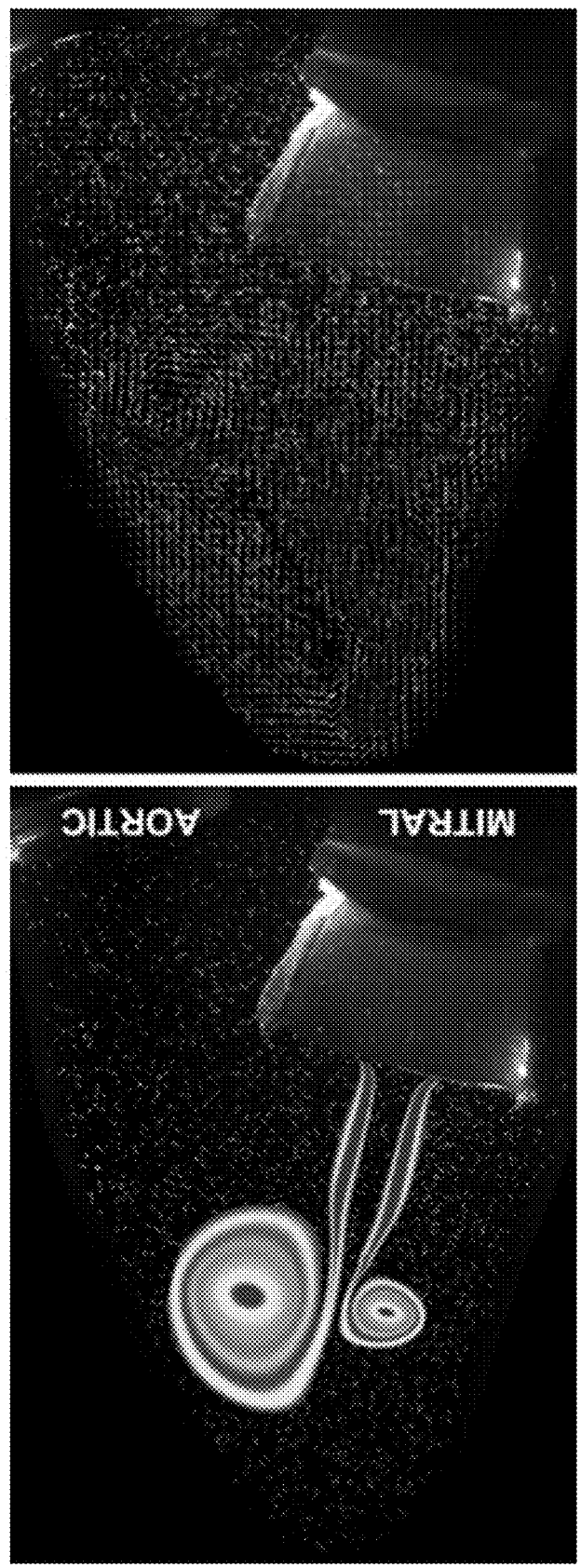
FIG. 18. Vortex formation downstream of a bileaflet mitral valve in a heart flow simulator, imaged by particle image velocimetry (PIV), shows asymmetric vortex like what is observed in native mitral valve. From Kheradvar and Falahatpisheh, *J Heart Valve Dis* 2014.

Optimization of the Bio-Inspired Bileaflet Mitral Valve Design to Generate Optimal Hemodynamics and Natural Transmitral Vortex Flow:

Many previous studies have confirmed the presence of vortical flow structures that develop along with the strong propulsive transmitral jet (Kheradvar A, Gharib M. On mitral valve dynamics and its connection to early diastolic flow. *Ann Biomed Eng.* 2009; 37:1-13; Kheradvar A, Houle H, Pedrizzetti G, Tonti G, Belcik T, Ashraf M, Lindner J R, Gharib M, Sahn D J. Echocardiographic particle image velocimetry: A novel technique for quantification of left ventricular blood vorticity pattern. *J Am Soc Echocardiogr.* 2010; 23:86-94; Kheradvar A, Milano M, Gharib M. Correlation between vortex ring formation and mitral annulus dynamics during ventricular rapid filling. *ASAIO J.* 2007; 53:8-16; Kilner P J, Yang G-Z, Wilkes A J, Mohiaddin R H, Firmin D N, Yacoub M H. Asymmetric redirection of flow through the heart. *Nature.* 2000; 404:759-761; and Pedrizzetti G, Domenichini F, Tonti G. On the left ventricular vortex reversal after mitral valve replacement. *Ann Biomed Eng.* 2010; 38:769-773). In normal hearts, the leading vortex transfers extra momentum from the left atrium (LA), to left ventricle (LV), contributing to efficient blood transport toward the aorta (Dabiri J O, Gharib M. The role of optimal vortex formation in biological fluid transport. *Proc Biol Sci.* 2005; 272:1557-1560). More recent studies show that the transmitral vortex ring is non-axisymmetric in normal LVs (Elbaz M S M, Calkoen E E, Westenberg J J M, Lelieveldt B P F, Roest A A W, van der Geest R J. Vortex flow during early and late left ventricular filling in normal subjects: Quantitative characterization using retrospectively-gated 4d flow cardiovascular magnetic resonance and three-dimensional vortex core analysis. *Journal of Cardiovascular Magnetic Resonance.* 2014; 16:78), and that this asymmetry helps the left heart optimize the blood momentum transfer (Kheradvar A, Assadi R, Falahatpisheh A, Sengupta P P. Assessment of transmitral vortex formation in patients with diastolic dysfunction. *J Am Soc Echocardiogr.* 2012; 25:220-227; Falahatpisheh A, Kheradvar A. A measure of axisymmetry for vortex rings. *European Journal of Mechanics—B/Fluids.* 2015; 49, Part A: 264-271; and Falahatpisheh A, Pahlevan N, Kheradvar A. Effect of the mitral valve's anterior leaflet on axisymmetry of transmitral vortex ring. *Annals of Biomedical Engineering.* 2015; 43:2349-2360). Proximity of the leaflets' tip to the ventricular wall significantly affects the process of vortex formation (Shariff K, Leonard A. Vortex rings. *Annu. Rev. Fluid Mech.* 1992; 24:U235-U279), and the flow pattern observed downstream of our bio-inspired, bileaflet mitral valve with longer leaflets closely mimics the vortex flow pattern observed downstream of the native mitral valve (FIG. 18). Using Echo-PIV in our heart flow simulator (Kheradvar A, Houle, H., Pedrizzetti, G., Tonti, G., Belcik, T., Ashraf, M., Lindner, J. R., Gharib, M., Sahn, D. Echocardiographic particle image velocimetry: A novel technique for quantification of left ventricular blood vorticity pattern. *J Am Soc Echocardiogr.* 2010; 23:3102-3111), we ensure that the valve generates asymmetric transmitral vortex like the native mitral valve. Further, valve hemodynamics will be optimized to generate the desired geometric orifice area (GOA) at low pressure gradient, according to FDA's ISO-5840.

Durability testing in an Accelerated Wear Test (AWT) System:

The Carbothane mitral valve scaffold in our AWT system (M6 Heart Valve Durability Tester, Dynatek Labs, Galena, Mo.) is tested according to ISO-5840, as we performed previously for the trileaflet scaffold (FIG. 15). The AWT experiments test the scaffolds' durability. The durability studies over a six-months achieve 200 million cycles (equivalent to 5 years in the body) according to ISO-5840. ISO 5840-1:2015 is applicable to heart valve substitutes intended for human implantation ((ISO) IOfS. Iso 5840-1: 2015: Cardiovascular implants—cardiac valve prostheses 2015). The AWT system can accommodate up to six valves at any time. We prefer to run these valves between 800-1000 cpm to keep the valves stable during the test. Higher speeds may interfere with the leaflets' fundamental frequency. Running at 800 cpm, it takes about 173 days to complete the required 200M cycles. At every 50M cycles, or in the case of any valve dysfunction, we stop the system and check the valves under a microscope to look for any potential defects, or signs of wear. These tests ensure that the Carbothane scaffolds possess an optimal mitral valve design and surpass the FDA required durability measures to minimize any safety issues for in-human implantation.

Tissue Extraction from the Sheep's Jugular Vein:

We use vascular cells from autologous veins for seeding of the hybrid valves. This is an acceptable cell source (Zhang W J, Liu W, Cui L, Cao Y. Tissue engineering of blood vessel. *Journal of Cellular and Molecular Medicine.* 2007; 11:945-957), as even patients with valve disease do not have abnormal venous vascular cells. For example, mitral stenosis is due mainly to rheumatic heart disease, and mitral insufficiency is rarely due to the inherent tissue. Therefore, using normal cells from peripheral venous walls generates excellent tissues. In the case of calcific aortic valve disease, it is believed that the calcification process is initiated with the development of atherosclerosis along the valve, which leads to valvular osteoblast differentiation. However, peripheral veins do not develop atherosclerosis. A 1-inch portion of jugular vein is surgically removed from the sheep (FIG. 7A), minced under a sterile cell culture hood, and carefully washed by sterilized PBS 1× to remove blood clots and clumps from the vein tissue. The tissue's external and internal margins are removed to keep only the tunica media that contains a mixture of SMCs and FBs. The tissue clusters then are cut to 5 mm×5 mm segments and transferred to a sterilized Petri dish (FIG. 7B). The dish is kept in the hood for 30 minutes to let the tissue pieces attach to the top side of the Petri dish. After 30 minutes, the preheated, enriched cell culture media, along with SMC/FB growth factors, are gently added to each Petri dish well (FIG. 7B). The Petri dish is kept in a 37° C. incubator for a week, with medium replaced at 50% volume with preheated fresh medium every day. After 5 days, the cells migrate out of the tissue pieces, as confirmed under microscope (FIG. 7C). We let the cells proliferate to achieve enough cells for the H-TEHV culture (FIG. 7D). The cells are trypsinized for sorting and characterization as follows. For human testing, we use the saphenous vein.

Figure 19:
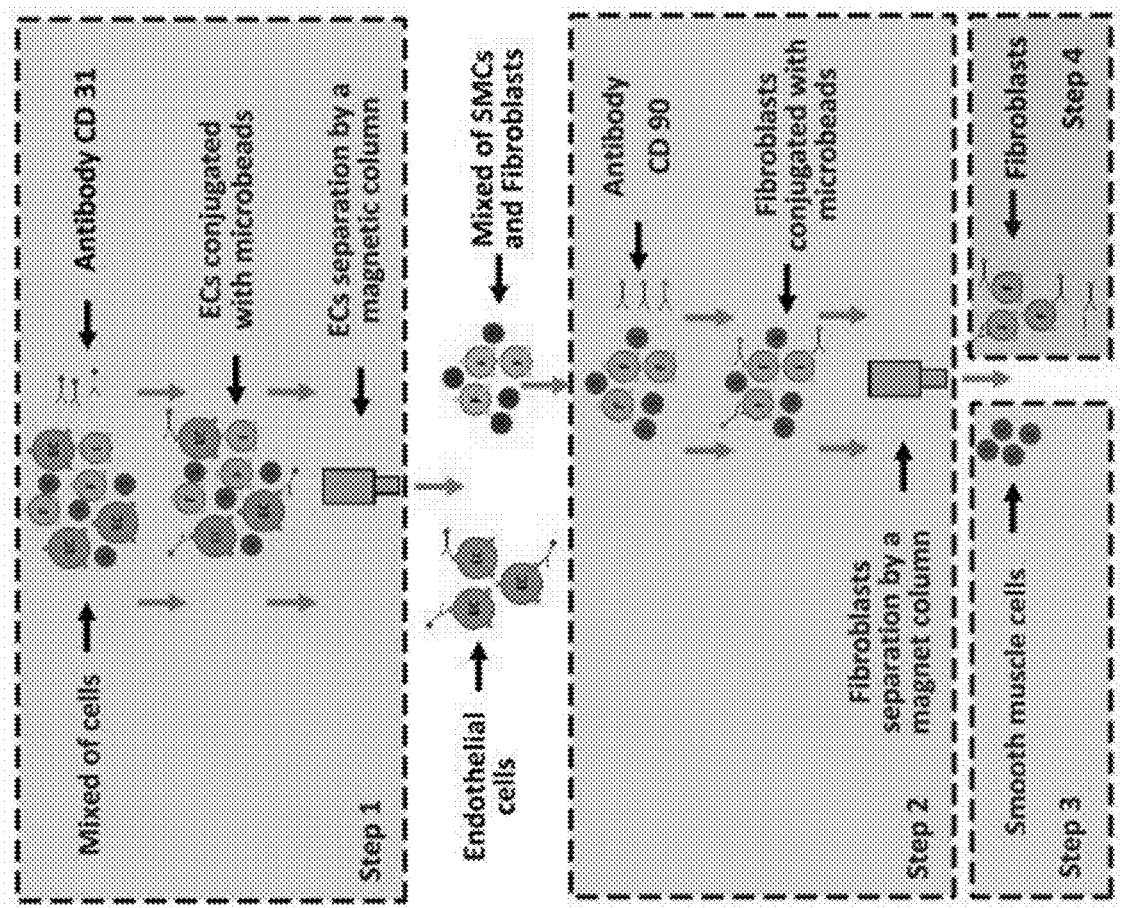
FIG. 19. cell separating process in four steps. Step 1) Endothelial cells separated from the whole extracted cells, Step 2) fibroblasts separation process, Step 3) Smooth muscle cell collection, Step 4) Fibroblast collection.

Cell Sorting and Characterization:

The native valve leaflets consist of three layers: fibrosa, spongiosa, and ventricularis, in which the majority of Valvular Interstitial Cells (VICs) consist of the population of pleomorphic fibroblastic VICs with some SMCs (Della Rocca F, Sartore S, Guidolin D, Bertiplaglia B, Gerosa G, Casarotto D, Pauletto P. Cell composition of the human pulmonary valve: A comparative study with the aortic valve—the vesalio* project. *The Annals of thoracic surgery.* 2000; 70:1594-1600; Aikawa E, Whittaker P, Farber M, Mendelson K, Padera R F, Aikawa M, Schoen F J. Human semilunar cardiac valve remodeling by activated cells from fetus to adult. *Circulation.* 2006; 113:1344; Bairati A, DeBiasi S. Presence of a smooth muscle system in aortic valve leaflets. *Anatomy and Embryology.* 1981; 161:329-340; Cimini M, Rogers K A, Boughner D R. Smoothelin-positive cells in human and porcine semilunar valves. *Histochemistry and cell biology.* 2003; 120:307-317 and Latif N, Sarathchandra P, Chester A H, Yacoub M H. Expression of smooth muscle cell markers and co-activators in calcified aortic valves. *European Heart Journal.* 2015; 36:1335-1345). The trypsinized cells are quantitatively sorted based on the method published by Weber et al. (Weber S C, Gratopp A, Akanbi S, Rheinlaender C, Sallmon H, Barikbin P, Koehne P S. Isolation and culture of fibroblasts, vascular smooth muscle, and endothelial cells from the fetal rat ductus arteriosus. *Pediatr Res.* 2011; 70:236-241), which magnetically labels the extracted cells and sorts them based on Magnetic-Activated Cell Sorting (MACS). We have used this method for cell isolation, applying both positive and negative selections. The cell sorting has four steps. The first step isolates the vascular endothelial cells (FIG. 19), then incubates the extracted cells at 20° C. for 30 min with an anti-vWF factor antibody (ab6994, Abcam), which specifically targets endothelial cells. The treated cells with the specific antibody are incubated with coated magnetic beads (goat anti-rabbit IgG, No. 486-02; Miltenyi Biotec). Then, these conjugated endothelial cells are isolated and removed by a magnetic column (positive selection). The remaining cells, a mixture of SMCs and FBs, are separated as follows. In the second step, the remaining cells are incubated with the specific fibroblast antibody (biotinylated mouse anti-rat CD90, No. 554893; BD Biosciences), at 20° C. for 30 min. The treated cells are incubated with coated magnetic beads (goat anti-mouse IgG, No. 130-048-101; Miltenyi Biotec). Then the FBs coupled with magnetic beads are isolated by a magnetic column (positive selection), and in the third step, the SMCs are similarly labeled, isolated, cultured, and adequately expanded into cell culture flasks with VSMC media. In the fourth step (FIG. 19), FBs are cultured into cell culture flasks with fibroblast growth factor. Following cell sorting by MACS, the isolated SMCs, ECs, and FBs are labeled by anti-Actin, anti-CD 90, and anti-vWF, respectively, and their purity is confirmed by Immunofluorescence staining and flow cytometry. FIG. 19 summarizes the cell isolation procedural steps. The SMC and FB are kept at 5-10% and 90-95%, respectively, to minimize the potential for calcification (Latif N, Sarathchandra P, Chester A H, Yacoub M H. Expression of smooth muscle cell markers and co-activators in calcified aortic valves. *European Heart Journal.* 2015; 36:1335-1345).

Figure 20:
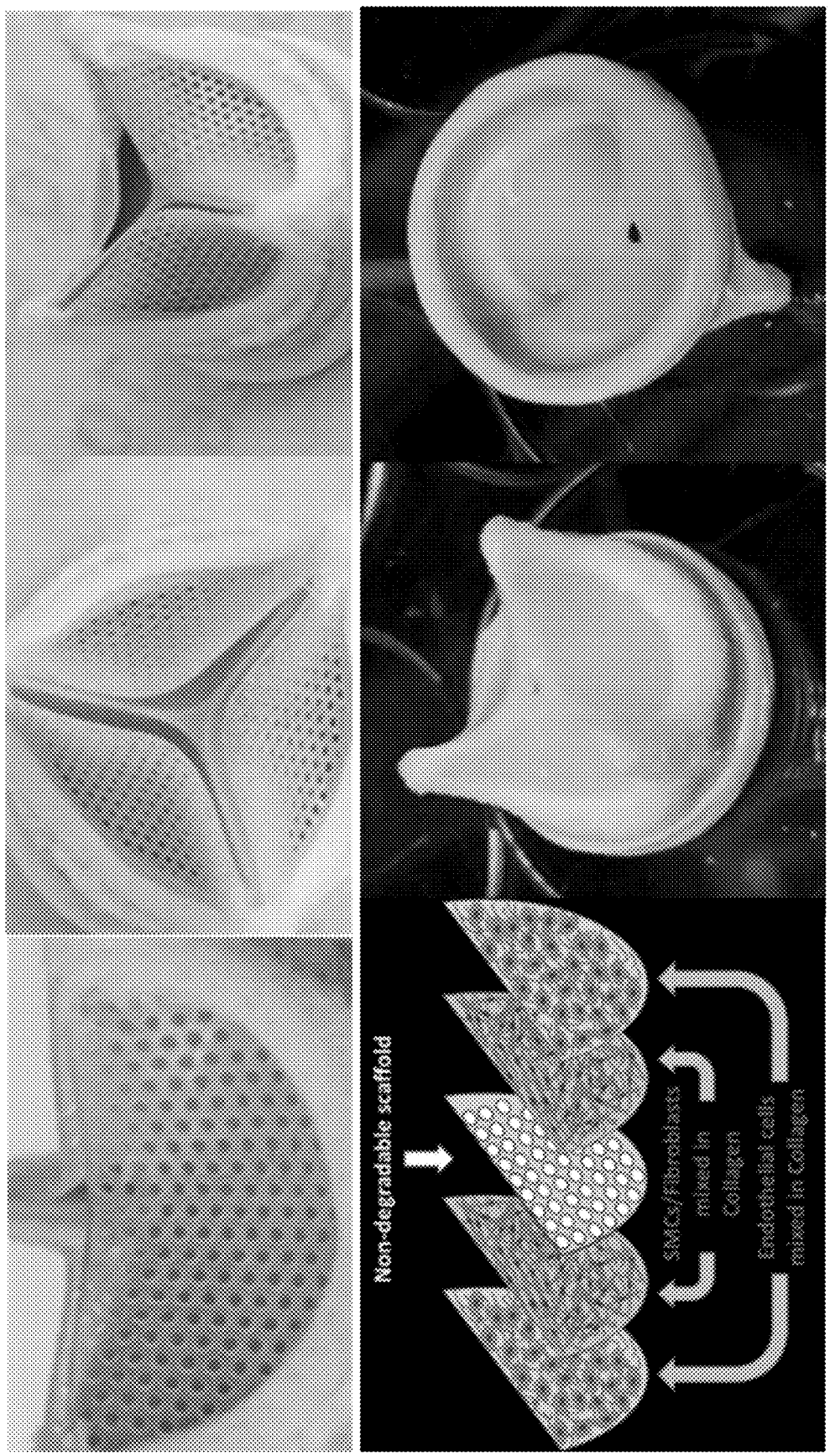
FIG. 20. (Top) Cabothane trileaflet valve scaffold fitted in the tissue culture mandrel. (Bottom left) Schematic of the two cell layers on each side of the valve; the first layer will be composed of 95% FBs and 5% SMC; the second layer will be made of endothelial cells. Top and bottom view of the final H-TEHV with Carbothane scaffold prior to implantation in sheep. A new tissue culture mandrel will be made to accommodate bileaflet mitral valve.

Hybrid TEHV Culture:

The proper mixture (e.g., 5/95 or 10/90) of SMCs and FBs, isolated and sorted as previously discussed, is used to culture the hybrid leaflets. Cells with a total density of about $2\times10^6$ cells per valve are seeded. The cells are cultured along with collagen type I over the sterilized valve scaffold by coating collagen solution and the extracted cells in the cell culture hood. The collagen concentration is set between 7 and 11 mg/mL (based on our first animal experiment). Afterwards, they are transferred to an incubator with $CO_2$ gas at a 37° C. temperature. Vascular endothelial cells at a total density of about $2\times10^6$ cells per valve that were harvested from the sheep and expanded are used to cover the previous layer. Like tri-leaflet H-TEHVs, as shown in FIG. 20, bileaflet H-TEHVs are prepared by casting the collagen solution that is mixed with SMCs and FBs over the bileaflet Carbothane mesh scaffold, which is finally covered by endothelial cells. We use a mandrel apparatus made of biocompatible PEEK (similar to FIG. 14) to accommodate bi-leaflet scaffolds. The apparatus is used for shaping and securing cells and tissue layers as they grow in 3-D into a heart valve. The mandrel includes two different components that secure the mixture of scaffold and cells from different sides, and let cells mixed with collagen be injected over the scaffold. The apparatus provides the ability to adjust the space between its two components so that multiple types of cells and tissue layers can be accommodated in time-steps ending with the endothelial layer. Our recently issued patent (U.S. Pat. No. 10,016,461) describes the apparatus's novel features. It currently takes 2 weeks to extract and expand the cells from tissue, and 1 week to seed the cells on the valve scaffold (3 weeks in total).

Figure 21:
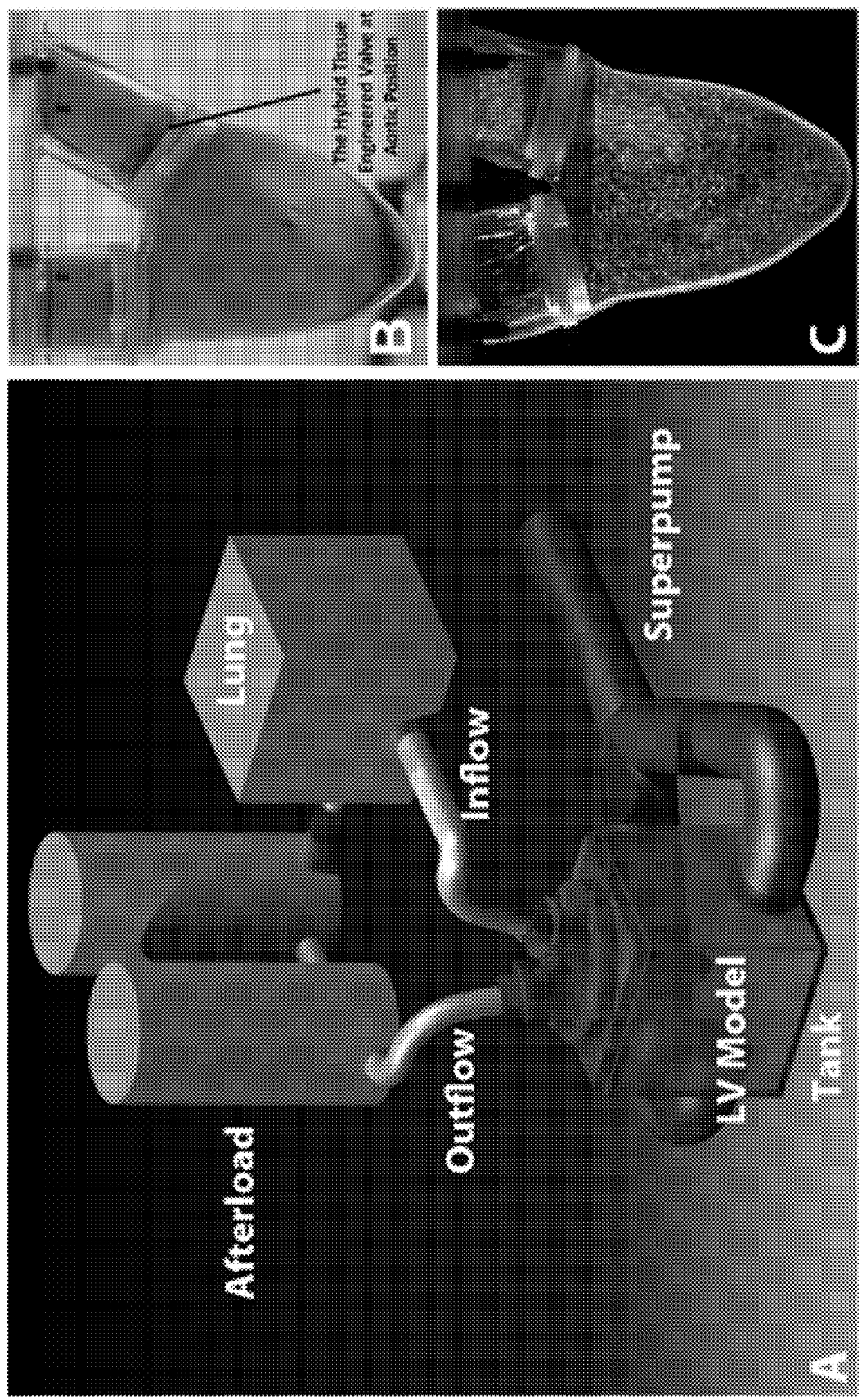
FIG. 21. (A) The schematics of heart flow simulator at Kheradvar lab. (B) A trileaflet H-TEHV implanted at the aortic position of the heart flow simulator; (C) Hear flow simulator with contrast agent showing transmitral flow.

Testing and Comparison of the Function and Hemodynamics of Bileaflet Vs. Trileaflet H-TEHV In Vitro:

The hemodynamics and function of the bileaflet H-TEHV are compared with trileaflet H-TEHV at mitral position in our heart flow simulator (Falahapisheh A, Kheradvar A. High-speed particle image velocimetry to assess cardiac fluid dynamics in vitro: From performance to validation. *European Journal of Mechanics—B/Fluids.* 2012; 35:2-8). The heart flow simulator system (FIG. 21), is a validated system that has been used to test the hemodynamics and performance of several heart valves in the past (Kheradvar A, Falahatpisheh, A. The effects of dynamic saddle annulus and leaflet length on transmitral flow pattern and leaflet stress of a bi-leaflet bioprosthetic mitral valve. *J Heart Valve Dis.* 2012; 21:225-233; Kheradvar A, Houle, H., Pedrizzetti, G., Tonti, G., Belcik, T., Ashraf, M., Lindner, J. R., Gharib, M., Sahn, D. Echocardiographic particle image velocimetry: A novel technique for quantification of left ventricular blood vorticity pattern. *J Am Soc Echocardiogr.* 2010; 23:3102-3111; Falahapisheh A, Kheradvar A. High-speed particle image velocimetry to assess cardiac fluid dynamics in vitro: From performance to validation. *European Journal of Mechanics—B/Fluids.* 2012; 35:2-8; Falahatpisheh A, Morisawa D, Toosky T T, Kheradvar A. A calcified polymeric valve for valve-in-valve applications. *Journal of Biomechanics.* 2016; in press; Falahatpisheh A, Pedrizzetti G, Kheradvar A. Three-dimensional reconstruction of cardiac flows based on multi-planar velocity fields. *Exp Fluids.* 2014; 55:1848; Kheradvar A, Kasalko, J., Johnson, D., Gharib, M. An in-vitro study of changing profile heights in mitral bioprostheses and their influence on flow. *ASAIO J.* 2006; 52:34-38; Kheradvar A. Development and testing a dynamic bi-leaflet mitral prosthesis. *Circulation.* 2009; 120: S929-S929 and Kheradvar A, Gharib, M. On mitral valve dynamics and its connection to early diastolic flow. *Annals of Biomedical Engineering.* 2009; 37:1-13). Both bileaflet and trileaflet H-TEHVs are placed and tested at the mitral position inside the chamber. The heart-pulsed duplicator provides physiologic flow and allows tight control of the flow rate through the chamber's inlet and outlet using ultrasonic flow probes. We measure the pressure gradient required to open the valves, GOA, transmitral velocities, and other parameters according to ISO-5840. Further, we test and compare transmitral vortex (Kheradvar A, Gharib, M. On mitral valve dynamics and its connection to early diastolic flow. *Annals of Biomedical Engineering.* 2009; 37:1-13), residence time (Kheradvar A, Kasalko, J., Johnson, D., Gharib, M. An in-vitro study of changing profile heights in mitral bioprostheses and their influence on flow. *ASAIO J.*

2006; 52:34-38), and flow stresses (Falahatpisheh A, Kheradvar A. High-speed particle image velocimetry to assess cardiac fluid dynamics in vitro: From performance to validation. *European Journal of Mechanics—B/Fluids.* 2012; 35:2-8) by our echocardiographic particle image velocimetry (Echo-PIV) method (Kheradvar A, Houle, H., Pedrizzetti, G., Tonti, G., Belcik, T., Ashraf, M., Lindner, J. R., Gharib, M., Sahn, D. Echocardiographic particle image velocimetry: A novel technique for quantification of left ventricular blood vorticity pattern. *J Am Soc Echocardiogr.* 2010; 23:3102-3111). A bio-inspired, bileaflet H-TEHV in mitral position provides improved function and hemodynamics over the standard trileaflet H-TEHV.

Alternative Approaches:

Using different cell types (e.g., venous vascular FBs and SMCs) other than the original VICs may be a limitation, as these peripheral cell types may show different characteristics than the original VICs. Nevertheless studies performed by others lead us to expect a behavior similar to VIC (Della Rocca F, Sartore S, Guidolin D, Bertiplaglia B, Gerosa G, Casarotto D, Pauletto P. Cell composition of the human pulmonary valve: A comparative study with the aortic valve—the vesalio* project. *The Annals of thoracic surgery.* 2000; 70:1594-1600; Cimini M, Rogers K A, Boughner D R. Smoothelin-positive cells in human and porcine semilunar valves. *Histochemistry and cell biology.* 2003; 120:307-317; Rabkin-Aikawa E, Farber M, Aikawa M, Schoen F J. Dynamic and reversible changes of interstitial cell phenotype during remodeling of cardiac valves. *Journal of Heart Valve Disease.* 2004; 13:841-847; Taylor P M, Batten P, Brand N J, Thomas P S, Yacoub M H. The cardiac valve interstitial cell. *The international journal of biochemistry & cell biology.* 2003; 35:113-118; Sartore S, Franch R, Roelofs M, Chiavegato A. Molecular and cellular phenotypes and their regulation in smooth muscle. *Reviews of physiology biochemistry and pharmacology, volume* 134. Springer; 1999:235-320; and Taylor P, Allen S, Yacoub M. Phenotypic and functional characterization of interstitial cells from human heart valves, pericardium and skin. *The Journal of heart valve disease.* 2000; 9:150). If we discover that ECs from arterial-like cells are more suitable for valve applications, we will use adipose tissue, which contains abundance of microvascular ECs that can be readily obtained. The derived EC types are tested for basic critical functions (non-thrombogenic, non-inflammatory), using the method developed by Dr. Craig Simmons (consultant) in which they characterized valve EC phenotypes from both sides of the valve by microarray (Simmons C A, Grant G R, Manduchi E, Davies P F. Spatial heterogeneity of endothelial phenotypes correlates with side-specific vulnerability to calcification in normal porcine aortic valves. *Circulation Research.* 2005; 96:792-799). A quantitative comparison of cells before/after cell culture expansion is performed to check cell isolation method yields to cells that are functionally equivalent to those within the valve. If the cells that are suboptimal, an alternative approach is to use sheep-derived stem cells (Vahedi P, Soleimanirad J, Roshangar L, Shafaei H, Jarolmasjed S, Nozad Charoudeh H. Advantages of sheep infrapatellar fat pad adipose tissue derived stem cells in tissue engineering. *Advanced Pharmaceutical Bulletin.* 2016; 6:105-110; Zhu X, Liu Z, Deng W, Zhang Z, Liu Y, Wei L, Zhang Y, Zhou L, Wang Y. Derivation and characterization of sheep bone marrow-derived mesenchymal stem cells induced with telomerase reverse transcriptase. *Saudi Journal of Biological Sciences.* 2017; 24:519-525; and Music E, Futrega K, Doran M R. Sheep as a model for evaluating mesenchymal stem/stromal cell (msc)-based chondral defect repair. *Osteoarthritis and Cartilage.* 2018; 26:730-740); as more recent studies have shown that stem cells can be shifted toward VIC differentiation (Weber B, Scherman J, Emmert M Y, Gruenenfelder J, Verbeek R, Bracher M, Black M, Kortsmit J, Franz T, Schoenauer R, Baumgartner L, Brokopp C, Agarkova I, Wolint P, Zund G, Falk V, Zilla P, Hoerstrup S P. Injectable living marrow stromal cell-based autologous tissue engineered heart valves: First experiences with a one-step intervention in primates. *European Heart Journal.* 2011; 32:2830-2840; Colazzo F, Sarathchandra P, Smolenski R T, Chester A H, Tseng Y-T, Czernuszka J T, Yacoub M H, Taylor P M. Extracellular matrix production by adipose-derived stem cells: Implications for heart valve tissue engineering. *Biomaterials.* 2011; 32:119-127; and Duan B, Hockaday L A, Das S, Xu C, Butcher J T. Comparison of mesenchymal stem cell source differentiation toward human pediatric aortic valve interstitial cells within 3d engineered matrices. *Tissue Engineering. Part C, Methods.* 2015; 21:795-807). Such a strategy is likely important for utilizing stem cell sources in heart valve tissue engineering applications as these differentiated cells are able to produce ECM components that are difficult to obtain with adult cells (e.g., elastin) (Duan B, Hockaday L A, Das S, Xu C, Butcher J T. Comparison of mesenchymal stem cell source differentiation toward human pediatric aortic valve interstitial cells within 3d engineered matrices. *Tissue Engineering. Part C, Methods.* 2015; 21:795-807). We have recently shown that perivascular cells from the human umbilical cord make ECM's collagen, elastin, GAGs in quantities much more than marrow-derived MSCs. As needed, we will use this strategy in sheep. Regardless, the quantity of ECM proteins should be adequate, as shown in FIGS. 12 and 13. Using the above-mentioned strategies in addition to 3D culture techniques and applying dynamic conditioning in vitro, ECM generation and homeostasis should be significantly improved. Most studies, including ours, show that elastin is poorly generated due to the use of adult cells (Alavi S H, Kheradvar A. A hybrid tissue-engineered heart valve. *The Annals of thoracic surgery.* 2015; 99:2183-2187; Lee K-W, Wang Y. Elastomeric pgs scaffolds in arterial tissue engineering. *Journal of Visualized Experiments: JoVE.* 2011:2691; and Flanagan T C, Cornelissen, C., Koch, S., Tschoeke, B., Sachweh, J. S., Schmitz-Rode, T., Jockenhoevel, S. The in vitro development of autologous fibrin-based tissue-engineered heart valves through optimised dynamic conditioning. *Biomaterials.* 2007; 28:3388-3397). Recent studies suggest that under proper dynamic conditioning, elastin production can be improved (Bye F J, Wang L, Bullock A J, Blackwood K A, Ryan A J, MacNeil S. Postproduction processing of electrospun fibres for tissue engineering. *Journal of Visualized Experiments: JoVE.* 2012:4172). Thus, we expect that the dynamic conditioning, as described in Example 3, will improve elastin content. If these efforts do not improve elastin production, we will use stem cells, as indicated earlier. Some studies suggest that SMCs are only a minority population in heart valves and may be responsible for calcification (Latif N, Sarathchandra P, Chester A H, Yacoub M H. Expression of smooth muscle cell markers and co-activators in calcified aortic valves. *European Heart Journal.* 2015; 36:1335-1345). If we find any trace of calcification, we will eliminate SMCs.

We have achieved: (1) Development of bileaflet Carbothane scaffolds that prove durable by exceeding 200M cycles in AWT system; and (2) Development of bileaflet H-TEHVs that generate optimal hemodynamics according to ISO-5840, surpassing the trileaflet H-TEHVs' with standard design in vitro.

EXAMPLE 3

Development of a Reproducible Adaptation and Conditioning Protocol to Optimize Hybrid TEHV's Cellular Performance Under Physiologic Pressure We mount the bileaflet H-TEHVs in physiologic heart valve bioreactors and subject them to progressive increases in pressures and flow to evaluate cell viability and the valve's ability to maintain ECM homeostasis. Such mechanistic studies on scaffold-cell interactions demonstrate in vitro tissue formation and optimized valve development with minimal delamination. This provides a basis for ready-to-implant valves with optimal composition.

Figure 22:
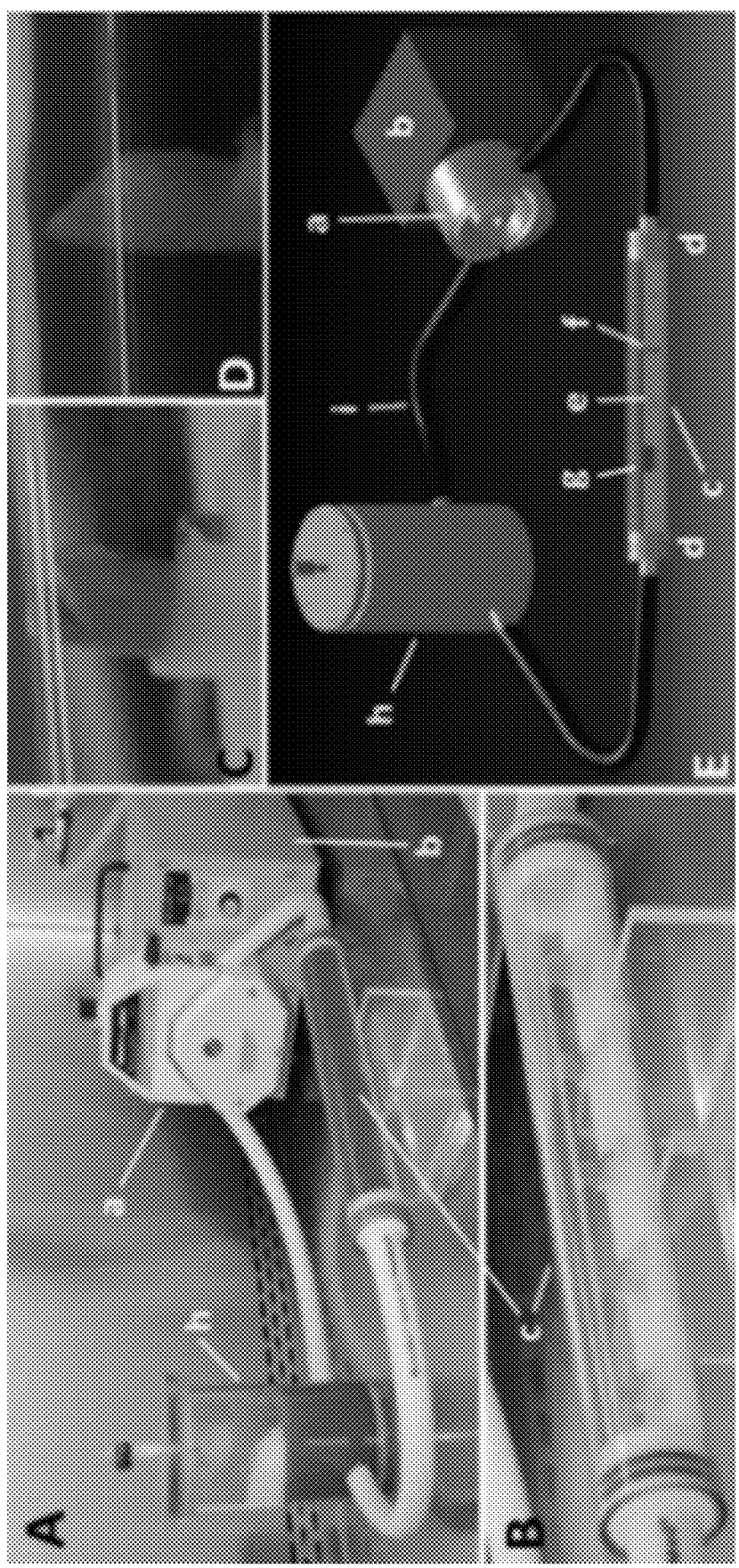
FIG. 22. (A) The experimental setup for assessing tissue-scaffold attachment under flow conditions including peristaltic pump system, tube-shaped container, compliance chamber, and tubing system. (B) Five hybrid leaflet samples assembled in the tube using a novel tissue gripping system; (C) Hybrid tissue samples in a configuration perpendicular to the flow, replicating a closed-valve situation where maximal stress is applied to the leaflets; (D) The same hybrid tissue sample under the flow with a rate of 5.2 L/min while the setup was running. Under the load, the tissue remained attached to the mesh; (E) Schematic of the bioreactor shows the components of the bioreactor; more info is available in Alavi and Kheradvar, 2015.

Bioreactor Design for Dynamic Conditioning of the Hybrid Leaflets and Testing of Tissue-Scaffold Attachment:

We previously developed a bioreactor to dynamically culture the leaflets and to test the tissue-scaffold attachment under pulsatile flow. The hybrid tissue-engineered leaflets were placed in the bioreactor and exposed to physiological flow rates (FIG. 22). The entire system was placed inside an incubator with basal media as circulating media. Dynamic conditioning is performed under a flow rate of 5 L/min. This bioreactor was used to test the hybrid leaflets' tissue-metal attachment when subjected to flow. This closed-valve situation replicated maximal stress applied to the leaflets by placing the tissue sample in a configuration perpendicular to the flow. The circulating media in the system was the basal media for culturing cells. When hybrid tissue leaflets underwent pulsatile flow rates from 1 to 5.2 L/min for 24 hours, no tissue deterioration, delamination, or separation was observed (FIG. 22, D) (Alavi S H, Kheradvar A. A hybrid tissue-engineered heart valve. *The Annals of thoracic surgery.* 2015; 99:2183-2187).

Figure 23:
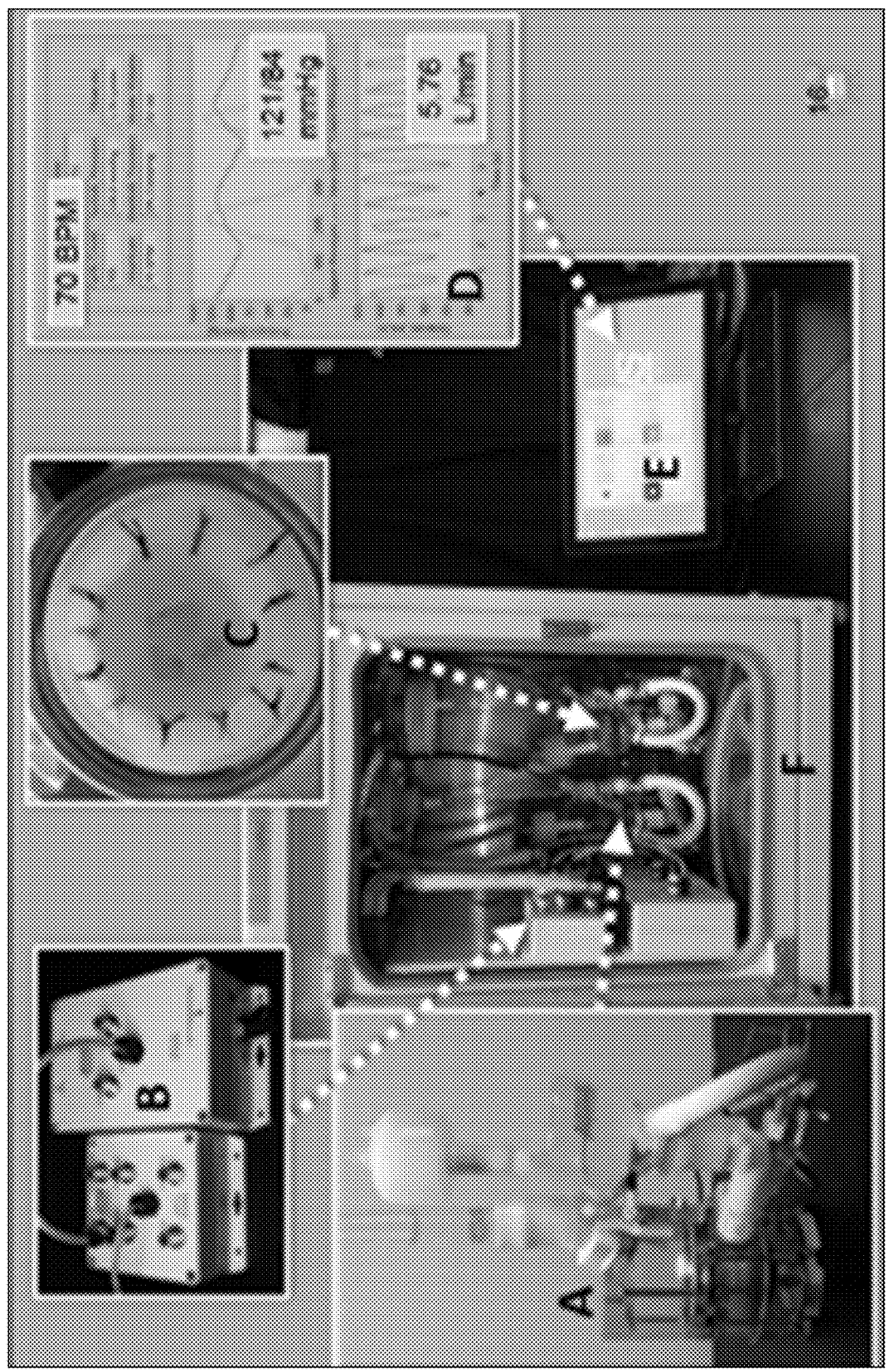
FIG. 23. Aptus heart valve bioreactor system. (A) acrylic chamber; (B) control and I/O module; (C) valve; (D) Aptus Physio control software; (E) typical flow profile and outputs for pressures, heart rate, and stroke volume. (F) two systems fit within a standard cell culture incubator.

The Mitral Valve Bioreactor:

This bioreactor incorporates patented technology (commercialized by Aptus, LLC), that has been developed and used extensively for a variety of projects (Tedder M E, Simionescu A, Chen J, Liao J, Simionescu D T. Assembly and testing of stem cell-seeded layered collagen constructs for heart valve tissue engineering. *Tissue Eng Part A.* 2011; 17:25-36; Sierad L N, Simionescu A, Albers C, Chen J, Maivelett J, Tedder M E, Liao J, Simionescu D T. Design and testing of a pulsatile conditioning system for dynamic endothelialization of polyphenol-stabilized tissue engineered heart valves. *Cardiovasc Eng Technol.* 2010; 1:138-153; and Tedder M E, Liao J, Weed B, Stabler C, Zhang H, Simionescu A, Simionescu D T. Stabilized collagen scaffolds for heart valve tissue engineering. *Tissue Eng Part A.* 2009; 15:1257-1268), including tissue-engineered mitral valves (FIG. 23) (Deborde C, Simionescu D T, Wright C, Liao J, Sierad L N, Simionescu A. Stabilized collagen and elastin-based scaffolds for mitral valve tissue engineering. *Tissue Eng Part A.* 2016; 22:1241-1251). Valves are mounted in the MechAnnulus valve holding system and placed between the sterile ventricular and atrial chambers within a segmented acrylic structure, powered by a computer-controlled external air pump system. All chambers have multiple ports for pressure and flow transducers, and for rapid media exchange. One-way valves ensure unidirectional flow of media. The bioreactor contains about 800 mL of culture medium and produces physiologic pulsatile flows at systemic pressures (120/10 mmHg), and variable stroke rates (up to 100 mL stroke volume). The system has a small footprint (30 cm height×13 cm diameter), allowing up to 4 systems to be run in one standard-size cell culture incubator. The clear, flat top of the atrial chamber facilitates unobstructed recording of leaflet motions using a camera which allows for hemodynamic measurements such as GOA (Kennamer A, Sierad L N, Pascal M, Rierson N, Albers C, Harpa M, Cotoi O, Olah P, Preda T, Simionescu A, Simionescu D. Bioreactor conditioning of valve scaffolds seeded internally with adult stem cells. *Tiss Eng Reg Med.* 2015; 1: in press). The system continuously monitors hydrodynamic pressures and flow, and allows full control of frequency (bpm), open/closed time (duty cycle), stroke volume (flow rate), and systolic/diastolic pressures. Using the Aptus system, progressive dynamic conditioning of stem cell-seeded heart valves induced stem cell differentiation into quiescent VICs has been demonstrated (Tedder M E, Simionescu A, Chen J, Liao J, Simionescu D T. Assembly and testing of stem cell-seeded layered collagen constructs for heart valve tissue engineering. *Tissue Eng Part A.* 2011; 17:25-36).

Proper conditioning of the H-TEHV's living tissue results in leaflets' optimal composition, similar to native mitral valve, maintain ECM homeostasis, and provide a non-thrombogenic surface.

A consideration in heart valve tissue engineering is ensuring cell viability and maintaining appropriate cellular phenotypes after implantation. We have shown that immediate exposure of cell-seeded scaffolds to the pressure and flow that heart valves experience may result in major cell demise (Kennamer A, Sierad L N, Pascal M, Rierson N, Albers C, Harpa M, Cotoi O, Olah P, Preda T, Simionescu A, Simionescu D. Bioreactor conditioning of valve scaffolds seeded internally with adult stem cells. *Tiss Eng Reg Med.* 2015; 1: in press). To reduce trial-and-error implantations in sheep, and to learn how to adapt the cells to the harsh mitral valve flow conditions in vivo, in vitro experiments are performed in our Aptus bioreactor. Cells can detect minuscule deviations in shear, flow, pressure, and mechanical stress. Deviations from normal conditions may induce cell activation and phenotypical changes, which do not constitute desirable outcomes. For example, endothelial cells activation in a H-TEHV may reduce its anti-thrombogenic properties. As well, H-TEHV's SMCs may lead to calcification, hyperplasia, or exaggerated ECM synthesis (Acampora K B, Nagatomi J, Langan E M, 3rd, LaBerge M. Increased synthetic phenotype behavior of smooth muscle cells in response to in vitro balloon angioplasty injury model. *Ann Vasc Surg.* 2010; 24:116-126). Thus, physiologic conditions are to be maintained within acceptable limits in vitro.

Conditioning of H-TEHV for Mitral Position:

Bileaflet Carbothane scaffolds (FIG. 17), and frozen ovine cells are provided. Cells are thawed, cultured, and seeded onto the valve scaffolds per the protocols described above. The H-TEHV is mounted within the sterile Aptus heart valve bioreactors (filled with DMEM/10% FBS/2% Ab-Am and 0.8% Dextran), placed in cell culture incubators at 37° C. and 5% $CO_2$, and subjected to progressive dynamic adaptation and conditioning with weekly media changes, with the aim of reaching mitral valve conditions of 120/10 mmHg at 70 bpm. The baseline adaptation steps are comprised of incremental increases in systolic pressures and heart rates every 12 hours until reaching 120/10 mmHg. Dextran is added gradually with every media change to reach the final 2.5% concentration, which approximates blood viscosity. This is followed by 7 days of conditioning at mitral conditions, followed by post-conditioning cell/tissue analysis. The Aptus system is capable of being programmed to run these scenarios automatically. We optimize the adaptation regime by using five variants, testing different slopes and intervals while increasing pressures from zero to 120/10 mmHg: at days 3.5, 7, 10, 14, and 24, respectively. At each time point, valves are removed, monitored over time for viability using Presto Blue assay and Live/Dead staining, and further analyzed, as described below. Controls consist of a) freshly seeded H-TEHV (t=0), b) H-TEHV maintained in static conditions, c) freshly collected ovine mitral valves, and d) freshly collected ovine mitral valves maintained alive in the heart valve bioreactor for the same time interval as above. This last group is useful for defining (largely unknown), ECM homeostasis parameters.

Post-Conditioning Cellular/Tissue Analysis:

Valves retrieved from the bioreactors are incubated first with Presto Blue viability reagent diluted in culture media for 30 minutes and then their fluorescence is measured at Ex560/Em590 on a plate reader. Small samples from the valve are also be incubated with Live/Dead reagent and cell viability assessed by en-face microscopy. Tissue samples are subjected to mRNA extraction and expression of specific markers using gene and protein analysis by microarrays (Qiagen's Ingenuity with pathway analysis) with PCR validation, western blotting, ELISA, and IHC. These data are compared with the post-explant data from the sheep (Aim 3) to study the difference between the in vivo and in vitro situations:

For endothelial cells (ECs) (Del Maschio A, Martin-Padura I, Bernasconi S, Dejana E. Triggering of beta 1-integrin chain induces platelet adhesion to cultured endothelium. *Arterioscler Thromb Vasc Biol.* 1997; 17:2663-2671), we look at constitutive markers such as CD31 (PECAM-1), vWF, acetylated LDL uptake (DiI-Ac-LDL), eNOS activity, GS lectin binding, α-smooth muscle actin (SMA) negativity, and inducible markers of activation: ICAM-1, VCAM-1, E-selectin, P-selectin, VEGFR-1, and VEGFR-2. This is very important, as EC dysfunction can initiate valve pathology. To analyze valve fibroblasts/myofibroblasts, we stain sections for fibroblast-specific protein (FSP1), fibroblast surface antigen (FSA), HSP47, vimentin, and FGF (Chester A H, El-Hamamsy I, Butcher J T, Latif N, Bertazzo S, Yacoub M H. The living aortic valve: From molecules to function. *Glob Cardiol Sci Pract.* 2014; 2014:52-77). Leaflet samples are also be tested for contractile responses to endothelin-1 and KCl (Chester A H, El-Hamamsy I, Butcher J T, Latif N, Bertazzo S, Yacoub M H. The living aortic valve: From molecules to function. *Glob Cardiol Sci Pract.* 2014; 2014:52-77). We also look for any "unwanted" cell phenotypes, specifically staining for osteoblast-like cells (osteocalcin, Runx2). For ECM remodeling, we measure synthesis and degradation of collagen, elastin, and proteoglycans. ECM synthesis is tested using the Biocolor kits for collagen, elastin, and proteoglycans. We also study the activity of Prolyl-hydroxylase, LOX, and trans-glutaminase enzymes, and synthesis of fibronectin, laminin, and type IV collagen by IHC. For ECM degradation, we measure MMPs and TIMPs in the cells and the ECM, and will calculate ratios of MMPs to TIMPs (89). To evaluate GAG homeostasis, we measure hyaluronic acid-synthase, hyaluronidase, and chondroitinase activity as described before (90; and 91). We also do Picrosirius and Movats' pentachrome ECM stains. TUNEL is done for apoptosis and Ki67 by IHC for cell proliferation.

Selection criteria for the optimal conditioning regime include: 1) statistically significant high cell viability as measured by Presto Blue and Live/Dead assay; 2) maintenance of constitutive endothelial cells and fibroblasts' markers with minimal upregulation of cell activation markers; and 3) expression of balanced ECM homeostasis with minimal upregulation of fibrosis or degeneration, similar to that found in native tissues (Strauss B H, Chisholm R J, Keeley F W, Gotlieb A I, Logan R A, Armstrong P W. Extracellular matrix remodeling after balloon angioplasty injury in a rabbit model of restenosis. *Circ Res.* 1994; 75:650-658).

Alternative Approaches:

Based on viability studies we are able to adapt the regimes to steeper or shallower slopes and validate them for the H-TEHV. The SMCs that have been reported at the base of the cusp in the ventricular layer may be just remnants of the transition zone between the vascular structure in the sinus and collagenous structure in the cusp per se (Latif N, Sarathchandra P, Chester A H, Yacoub M H. Expression of smooth muscle cell markers and co-activators in calcified aortic valves. *European Heart Journal.* 2015; 36:1335-1345). Our studies test different ratios of FBs and SMCs (i.e., 90/10, 95/5 and 100/0), and when the presence of SMC results in any issue, we use only FB+EC and eliminate SMCs in our tissue cultures.

We have developed bileaflet H-TEHVs with living tissue leaflets that show optimal ECM composition similar to native mitral valve, maintain ECM homeostasis, and provide a non-thrombogenic surface.

EXAMPLE 4

Study of Hybrid Bileaflet TEHV's Function, Hemodynamics, and Biocompatibility In Vivo by Implanting the Valves in the Mitral Position of an Ovine Model The optimally-designed and bioreactor-conditioned H-TEHVs are implanted in the mitral position of up to 20 sheep. Each sheep receives a valve made from its own cells. The valves' function and hemodynamics are assessed using echocardiography. The plasma levels of cytokines are assayed for 24 weeks prior to euthanizing the animals. We analyze the H-TEHV's microstructure and ECM deposition post-implant to optimize tissue formation that mimics native valves.

H-TEHV Implants in Sheep:

We have implanted the H-TEHV twice in sheep according to IACUC protocol#2012-3071. In the first procedure, we implanted a valve with a Nitinol scaffold, and more recently, we implanted one with a Carbothane scaffold where the valves were implanted in the sheep's mitral position. Post-procedure echocardiography showed competent valves without leakage, and the animals were recovered from anesthesia and transferred on their feet to vivarium without signs of stroke or other surgery-related problems.

Figure 24:
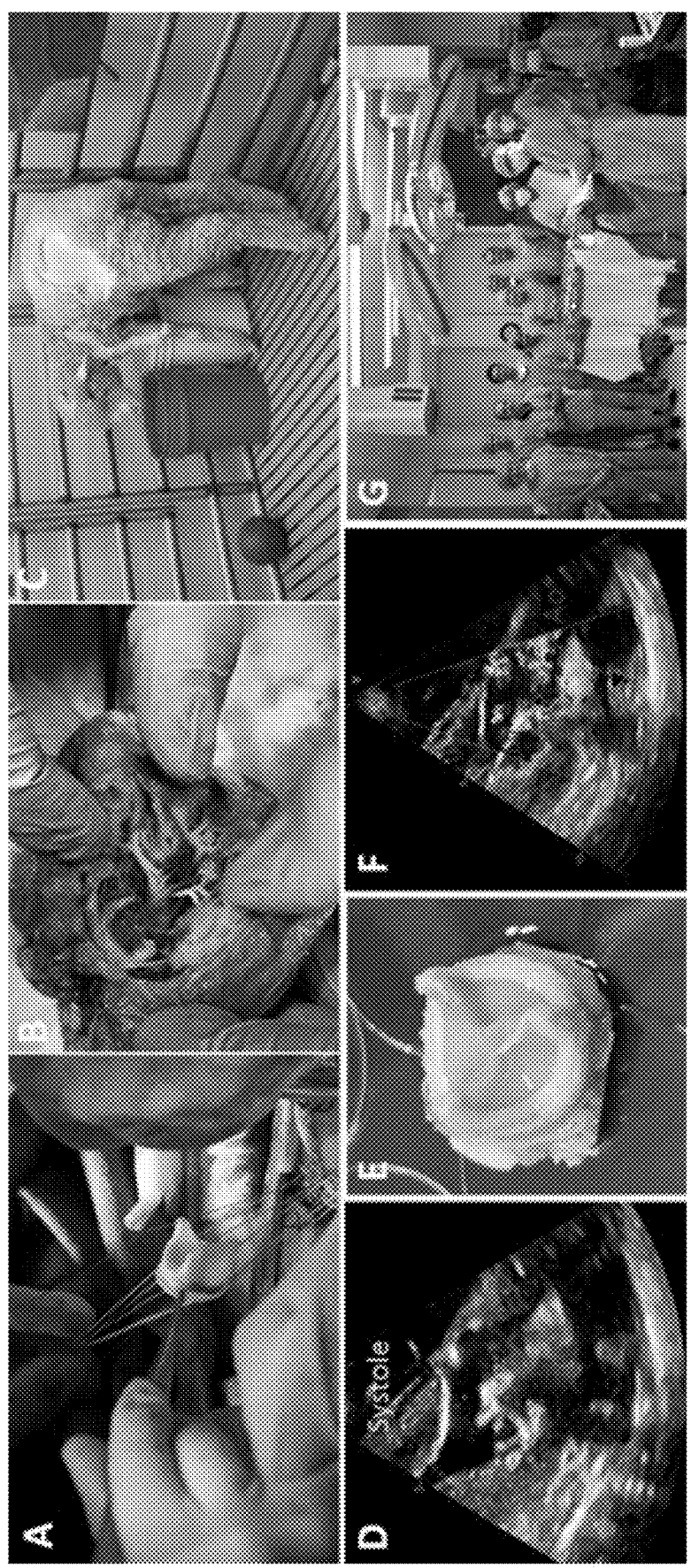
FIG. 24. Summary of the surgical implant of a hybrid TEHV with Carbothane scaffold (A) hybrid TEHV implantation in sheep mitral position; (B) postmortem study shows intact hybrid TEHV at the mitral valve; (C) the animal walks on his feet after surgery with no sign of stroke; (D) Echocardiography shows perfect leaflet coaptation during systole; (E) Dissected hybrid TEHV shows no sign of delamination or dehiscence after 7 hours beating in the sheep heart; (F) Color Doppler imaging shows the valve was competent with no sign of regurgitation; (G) Surgical and perfusion team at UCIMC after the successful procedure.

The animal study requires two steps: (1) extracting tissue from the sheep's jugular vein, and (2) implanting the H-TEHV grown from the sheep's own tissue in the animal's heart. The tissue extract was performed first to develop the valves. Once the H-TEHVs were developed, they were implanted in the sheep's mitral position through a midsternal thoracotomy using a heart-lung bypass machine under the control of a perfusion team, and the other one was kept as the control. The open-heart surgeries were successfully performed by our surgical and perfusion teams at UCIMC (FIG. 24). After the valve implantation, the implanted valves were comprehensively monitored by echocardiography. According to B-mode echocardiography, both valves' leaflet mobility was favorable, with perfect coaptation once closed, and no restriction in leaflet mobility was observed (FIG. 24, D). Additionally, no regurgitation or valve dysfunction was observed, based on the color Doppler data (FIG. 24, F). All the surgical procedures were performed successfully, and the sheep recovered and walked to the vivarium on his feet without any sign of stroke or other surgery-related problems. The study's results were presented as a talk at the HVS 2018 (Zareian R, Morisawa, D., Geertsema, R. S., Steward, E., Majid, M., Kapadia, A., Wynne C., Milliken, J. C., Kheradvar, A. First implantation of a hybrid tissue-engineered heart valve in a sheep's mitral position. *The Heart Valve Society* 2018 Annual Scientific Meeting. 2018).

The animal studies were planned to test the valve performance and function. Following the surgical procedures, we monitored the animals in the vivarium. The animal with the Nitinol scaffold expired 4 hours after the surgery due to excessive peripheral hemorrhage from the rupture of the intercostal artery during placement of the chest tube, possibly due to anticoagulation therapy. For the next study using the Carbothane scaffold, we corrected Heparin to 200 IU/Kg according to the guideline (Connell J M, Khalapyan T, Al-Mondhiry H A, Wilson R P, Rosenberg G, Weiss W J. Anticoagulation of juvenile sheep and goats with heparin, warfarin, and clopidogrel. *ASAIO journal.* 2007; 53:229-237), and the sheep did not experience any excessive bleeding. The animal with the Carbothane scaffold expired from pulmonary edema, a common open-heart surgery-related adverse reaction in sheep, eight hours after the surgery, totally unrelated to the H-TEHV prosthesis. The autopsy showed the intact H-TEHV without any tissue dehiscence (FIG. 24, E). We are currently improving our post-surgical care protocols and have been working with Edwards Lifesciences surgical veterinary team who routinely implants heart valves in sheep.

Implanting bileaflet H-TEHVs with dynamic annulus constituted of autologous cells in sheep leads to hemodynamics and function comparable to native mitral valve and durability, at least comparable to the FDA-approved bioprosthetic valves whose data is available in the literature.

Implanting the Bileaflet H-TEHVs in Sheep and Testing their Function, Hemodynamics, and Durability In Vivo:

Assessing the hybrid valve in vivo is important to determining whether these valves can maintain their natural function and self-regenerating capacity as hypothesized. To test this question, the valves prepared, and the bioreactor conditioned as described in Examples 2 and 3, are implanted in a sheep's mitral position, as previously performed. The valves' function is assessed using echocardiography. After 24 weeks, the animal is euthanized to evaluate the valves' self-regenerating capacity through histology of the implant and surrounding tissue.

We use up to 20 mature sheep (10 male and 10 female) weighing between 40 and 50 kg that have been raised for laboratory work by commercial vendors. All animals will receive humane care according to standard guidelines. Prior to any procedure, baseline echocardiographic data are acquired in the operating room by an expert echocardiographer. Our preclinical analyses is based on in vivo valve performance and leaflet thickness. To evaluate valve function, we measure ejection fraction, valvular stenosis, regurgitation, and leaflet thickness using echocardiography. The valve's leaflet thickness is monitored weekly to rule out potential stenosis/insufficiency or subclinical thrombosis. We follow the FDA's recommended guidelines for medical device implants (ISO-5840), to determine the number of animals required.

Postsurgical Follow-Up:

The animals are followed up at baseline and then serially on a weekly basis up to 24 weeks. Each follow-up session acquires echocardiographic data by an expert echocardiographer and blood samples for immunologic tests. To test the acute and chronic inflammatory response to implanted hybrid valves, we examine systemic levels of cytokines, including TNF-$\alpha$, IL-6, IL-1a/b, IL-10, and TGF-$\beta$, which include both pro-inflammatory and pro-healing cytokines, during the 24-week postsurgical follow-up, and compare those with the baseline levels prior to surgery. Echocardiography is used to assess valve patency, and regurgitation by examining peak velocity/regurgitant flow, flow field and vortex imaging by Echo-PIV, mean pressure gradient, and Effective Orifice Area (EOA). Completion of the preclinical study is followed by explantation and analysis of the valve mechanical properties and histology, as described below.

Post-Implant Cellular/Tissue Analysis:

An ideal tissue-engineered valve is one that once implanted closely mimics the native mitral valve. Therefore, one preferably demonstrates that the mitral H-TEHV's composition is similar to that of a native valve or becomes similar to a native mitral valve in vivo. The complex combination of biochemical and mechanical signals inside the body makes it an excellent environment for testing these models. Cell proliferation (DNA), is quantified, and cellular phenotypes are characterized by IHC and correlated spatially with ECM composition, as in FIGS. 12 and 13. We test how the ECM and distribution of cell phenotypes in the H-TEHVs evolve in the body compared to pre-implantation in the control valves. An abundance of myofibroblasts is expected, as an adaptation to the higher loading conditions in the LV (at least initially, perhaps followed by quiescence), enabling desirable ECM production and remodeling. In addition, a minor presence of SMCs and their contraction should help to damp the loading on the leaflets during systole when the mitral valve is exposed to highest pressure (Cimini M, Rogers K A, Boughner D R. Smoothelin-positive cells in human and porcine semilunar valves. *Histochemistry and cell biology.* 2003; 120:307-317; and Taylor P, Allen S, Yacoub M. Phenotypic and functional characterization of interstitial cells from human heart valves, pericardium and skin. *The Journal of heart valve disease.* 2000; 9:150). The explanted H-TEHVs' cellular and tissue characteristics are compared with known characteristics of native mitral valves in sheep (Martin C, Sun W. Biomechanical characterization of aortic valve tissue in humans and common animal models. *Journal of Biomedical Materials Research Part A.* 2012; 100A:1591-1599; Jiao T, Clifton R J, Converse G L, Hopkins R A. Measurements of the effects of decellularization on viscoelastic properties of tissues in ovine, baboon, and human heart valves. *Tissue Engineering Part A.* 2011; 18:423-431; and White J F, Werkmeister, J. A., Hilbert, S. L., Ramshaw, J. A. Heart valve collagens: Cross-species comparison using immunohistological methods. *J Heart Valve Dis.* 2010; 19:766-771). We stain the cells in the interstitium for markers of FB (vimentin), myofibroblasts (SMA, absence of SMC contractile proteins), and vascular SMCs (SMA, smooth muscle-myosin heavy chain, calponin, smoothelin), to determine relative proportions and distribution. Presence of an intact endothelium is confirmed by staining for CD31 and vWF. We also stain for cell phenotypes associated with early pathological outcomes, including inflammation (endothelium: VCAM, ICAM; inflammatory cells: CD45; macrophages: MAC-387), and osteo-chondrogenesis/calcification (Runx2, Msx2, Sox9) (White J F, Werkmeister, J. A., Hilbert, S. L., Ramshaw, J. A. Heart valve collagens: Cross-species comparison using immunohistological methods. *J Heart Valve Dis.* 2010; 19:766-771). In brief, valvular cell phenotype is identified, potential for pathological outcomes is assessed, and potential differences between the cells that are used in these engineered valves (i.e., FBs, SMCs, ECs) and the native cells that normally populate the valve (VICs, VECs), is tested to determine whether these differences are substantial (Simmons C A, Grant G R, Manduchi E, Davies P F. Spatial heterogeneity of endothelial phenotypes correlates with side-specific vulnerability to calcification in normal porcine aortic valves. *Circulation Research.* 2005; 96:792-799; and Sider K L, Zhu C, Kwong A V, Mirzaei Z, de Lange C F M, Simmons C A. Evaluation of a porcine model of early aortic valve sclerosis. *Cardiovascular Pathology.* 23:289-297). ECM formation and protein content (collagen, elastin, and GAG), are biochemically quantified and compared with control (unimplanted), H-TEHVs. Since a naturally comparable cell pattern with high cellularity is used in the H-TEHVs' leaflets, a robust ECM generation comparable to native valves' is expected. Histology is performed pre- and post-implantation on H-TEHVs for general morphology and ECM components, and by IHC for specific ECM protein components that are differentially expressed regionally in native leaflets (e.g., types I-Ill collagen), and specific proteoglycans/GAGs (biglycan, versican, decorin, hyaluronan). Calcification as a potential pathological outcome is assessed by von Kossa staining. Tissue area fractions and regional expression in different layers are determined histomorphometrically (Sider K L, Zhu C, Kwong A V, Mirzaei Z, de Langé C F M, Simmons C A. Evaluation of a porcine model of early aortic valve sclerosis. *Cardiovascular Pathology.* 23:289-297). ECM protein content is quantified and compared with in vitro results, as discussed in Example 3.

Figure 25:
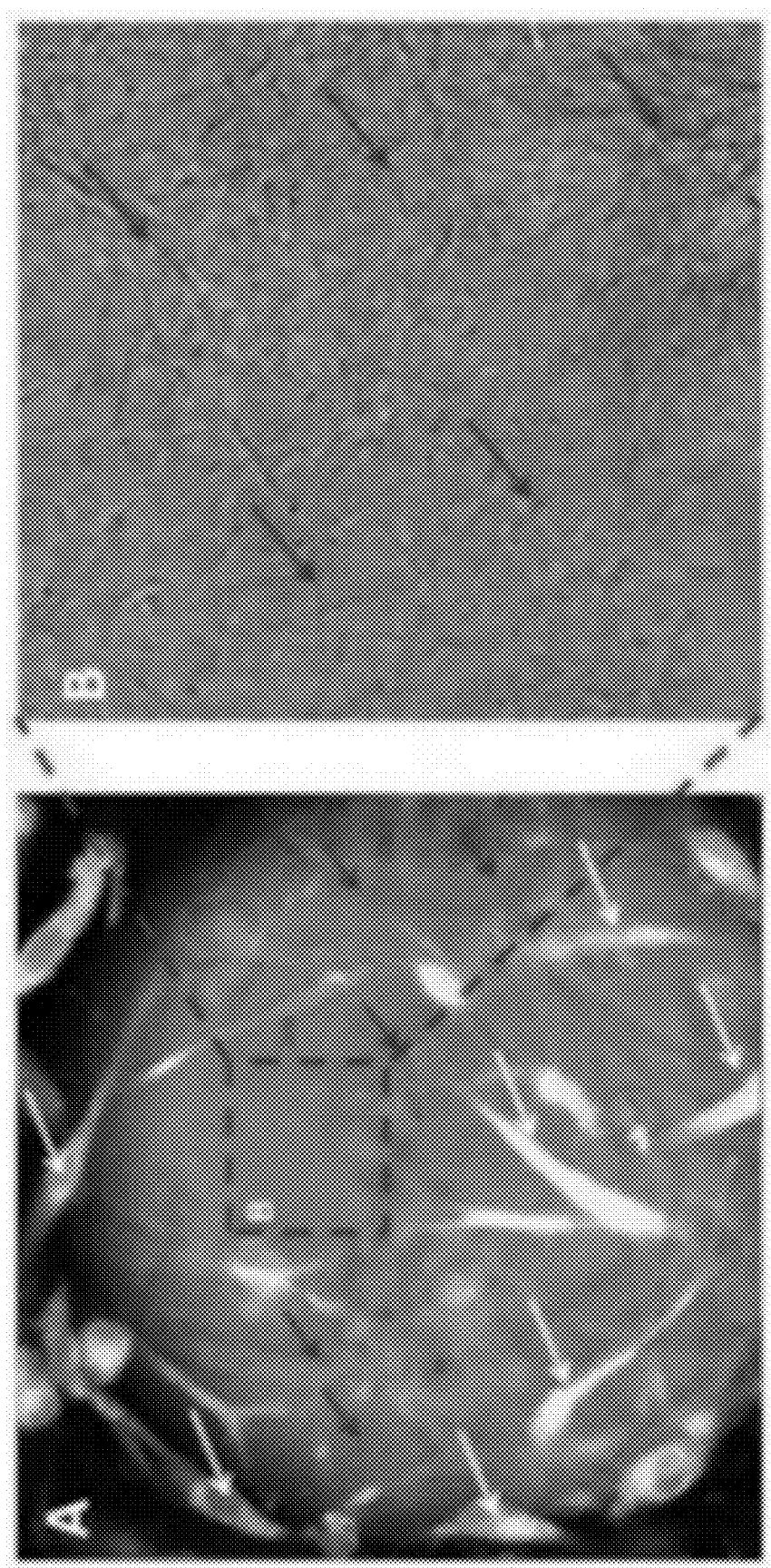
FIG. 25. Microstructural tissue arrangement of hybrid leaflet (A) Merged DIC and fluorescent images (Confocal microscopy) from fibroblasts/smooth muscle cell layer (top side of the mesh). Fibroblasts and collagen fibrils are indicated by white and red arrows, respectively. The image (A) is taken from one mesh pore by using 40x objective. (B) magnified image from the center of the mesh pore to show collagen fibrils.

Studying Post-Implant Microstructural Arrangement:

This step tests whether the cultured H-TEHVs mimic natural mitral valve composition. The formed tissue's macro- and microstructure are analyzed in a series of characterization assays to see how the tissue has been formed. This information facilitates analysis of the tissue morphology, cellular and ECM components, and distribution patterns within the leaflet tissues. Collagen fibers reinforce the tissue and provide structural integrity such that the very thin leaflet can stand enormous loads related to cyclic pressure changes (Alavi S H, Ruiz V, Krasieva T, Botvinick E, Kheradvar A. Characterizing the collagen fiber orientation in pericardial leaflets under mechanical loading conditions. *Ann Biomed Eng.* 2013; 41:547-561). The leaflet tissue's mechanical response depends on collagen fiber concentration, characteristics, and orientation. To characterize the H-TEHV's leaflets' 3-D collagen fiber arrangement, they are studied under confocal microscopy (FIG. 25). This method helps understand tissue formation and tests the hypothesis that cultured H-TEHVs mimic native mitral valve composition.

Real-Time Biaxial Testing Under Microscope:

To perform this study, a tissue specimen is mounted to a special setup made for the microscope stage using thin threads, allowing its edges to expand freely in the lateral direction (Alavi S H, Ruiz V, Krasieva T, Botvinick E, Kheradvar A. Characterizing the collagen fiber orientation in pericardial leaflets under mechanical loading conditions. *Ann Biomed Eng.* 2013; 41:547-561). The setup has been extensively described in our previous work (Alavi S H, Ruiz V, Krasieva T, Botvinick E, Kheradvar A. Characterizing the collagen fiber orientation in pericardial leaflets under mechanical loading conditions. *Ann Biomed Eng.* 2013; 41:547-561). Testing is performed with the specimen completely immersed in phosphate-buffered normal saline (pH 7.4) at 37° C. The biaxial mechanical characterization is performed under microscopy to closely monitor loading's effects on the H-TEHV's tissue structure and to compare the effects pre- and post-implant. Second Harmonic Generation (SHG) microscopy is a method widely used for imaging collagenous biological tissues such as valve leaflets, and does not require molecular probes (Schenke-Layland K. Non-invasive multiphoton imaging of extracellular matrix structures. *J Biophotonics.* 2008; 1:451-462; and Schenke-Layland K, Madershahian N, Riemann I, Starcher B, Halbhuber K J, Konig K, Stock U A. Impact of cryopreservation on extracellular matrix structures of heart valve leaflets. *Ann Thorac Surg.* 2006; 81:918-926). Collagen type I, which is common to heart valves, has a crystalline triple-helix structure effective at SHG conversion (Chen J, Lee A, Zhao J, Wang H, Lui H, McLean D I, Zeng H. Spectroscopic characterization and microscopic imaging of extracted and in situ cutaneous collagen and elastic tissue components under two-photon excitation. *Skin Res Technol.* 2009; 15:418-426; Cox G, Kable E, Jones A, Fraser I, Manconi F, Gorrell M D. 3-dimensional imaging of collagen using second harmonic generation. *J Struct Biol.* 2003; 141:53-62; and Georgiou E, Theodossiou T, Hovhannisyan V, Politopoulos K, Rapti G S, Yova D. Second and third optical harmonic generation in type i collagen, by nanosecond laser irradiation, over a broad spectral region. *Optics Communications.* 2000; 176:253-260). The H-TEHV's collagen fiber orientation pre- and post-implant is compared with the sheep native mitral valve leaflets, in relaxed and under loading conditions to test if H-TEHV's formed ECM follows a similar biomechanical trend to the native mitral valve's.

Alternative Approaches:

Leaflet impact during systole plays a major role in mitral valves' durability. Our in vitro and recent in vivo studies showed that optimal valve design is preferable to avoid harsh impacts on leaflets during valve closure (Alavi S H, Soriano Baliarda M, Bonessio N, Valdevit L, Kheradvar A. A tri-leaflet nitinol mesh scaffold for engineering heart valves. *Annals of Biomedical Engineering.* 2017; 45:413-426). Carbothane is biocompatible, with a very low calcification tendency and mechanical properties suitable for use as a heart valve scaffold. Post-surgical care for the sheep is preferable for follow-up studies and to keep the animal alive for 24 weeks.

We have demonstrated sheep surviving for 24 weeks with bileaflet H-TEHVs showing hemodynamics and function comparable to native mitral valve and durability at least comparable to the BHVs, and no calcification.

EXAMPLE 5

Protocol for Development of Hybrid Tissue Engineered Valve with Polyurethane Core Materials:

1—Clean latex gloves
2-70% Ethanol and kimwipes
3—Sterile razor blades
4—Aspirating pipets (1, 5 or 10 ml)
5—1 ml, 5 mL, 10 mL sterilized pipette tips
6—Nalgene Bottle Top Filters Sterile
7—Sterilized distilled water
8—Dulbecco's Phosphate Buffered Saline—DPBS 1× (Sigma-Aldrich 59321C-1000ML)
9—Fibronectin (from rat plasma—Sigma-Aldrich F0635-0.5MG)
10—Collagen type I (RatCol Rat Tail, Advanced BioMatrix 5153-100MG)
11—Media 1—Smooth Muscle Cell culture media (SmGm-2 Bullekit CC-3182)

12—Media 2—Human Umbilical Vascular Endothelial Cell culture media (EGM-2 Bulletkit CC-3162)
13—T-75 or T-175 cell culture flasks
14—Trypsin-EDTA (0.05%), phenol red—1× (Thermo-Fisher Scientific—25300054)
15—Tissue/cell culture plate—(Size 6 wells, sterile bottom flat)
16—MINIMACS Starting Kit (Miltenyi Biotec Company 130-090-312): including
    1—MACS MultiStand (130-042-303)
    2—MS Columns (130-042-201)
    3—MiniMACS Separator (130-042-102)
17—CD31 Antibody-IgG2a 0.1 mg/ml (Bio-Rad Company MCA1097GA)
18—Running buffer (Miltenyi Biotec Company 130-091-221)
19—PECK mold (the mold designed by KLab research group)
20—carbothane 95A polymer sheet (Lubrizol, Inc) with 250 micros thickness
21—Laser cutting machine (Versa VLS2.30 Laser System)
22—A titanium frame
23-15 and 50 mL centrifuge tubes
24—Autoclaved forceps
25—Automatic pipetters
26—Cell counter
27—Autoclave pouches
28—Autoclave
29—Cell culture hood
30—AWT durability machine
31—Cell culture Incubator at 37° C.

Safety:
1—Wear disposable latex gloves at all times.
2—Spray your latex gloves with 70% Ethanol and let them to dry when you work in the cell culture hood
3—Wear safety glasses and a lab coat, if you move cells from liquid nitrogen.

Figure 26:
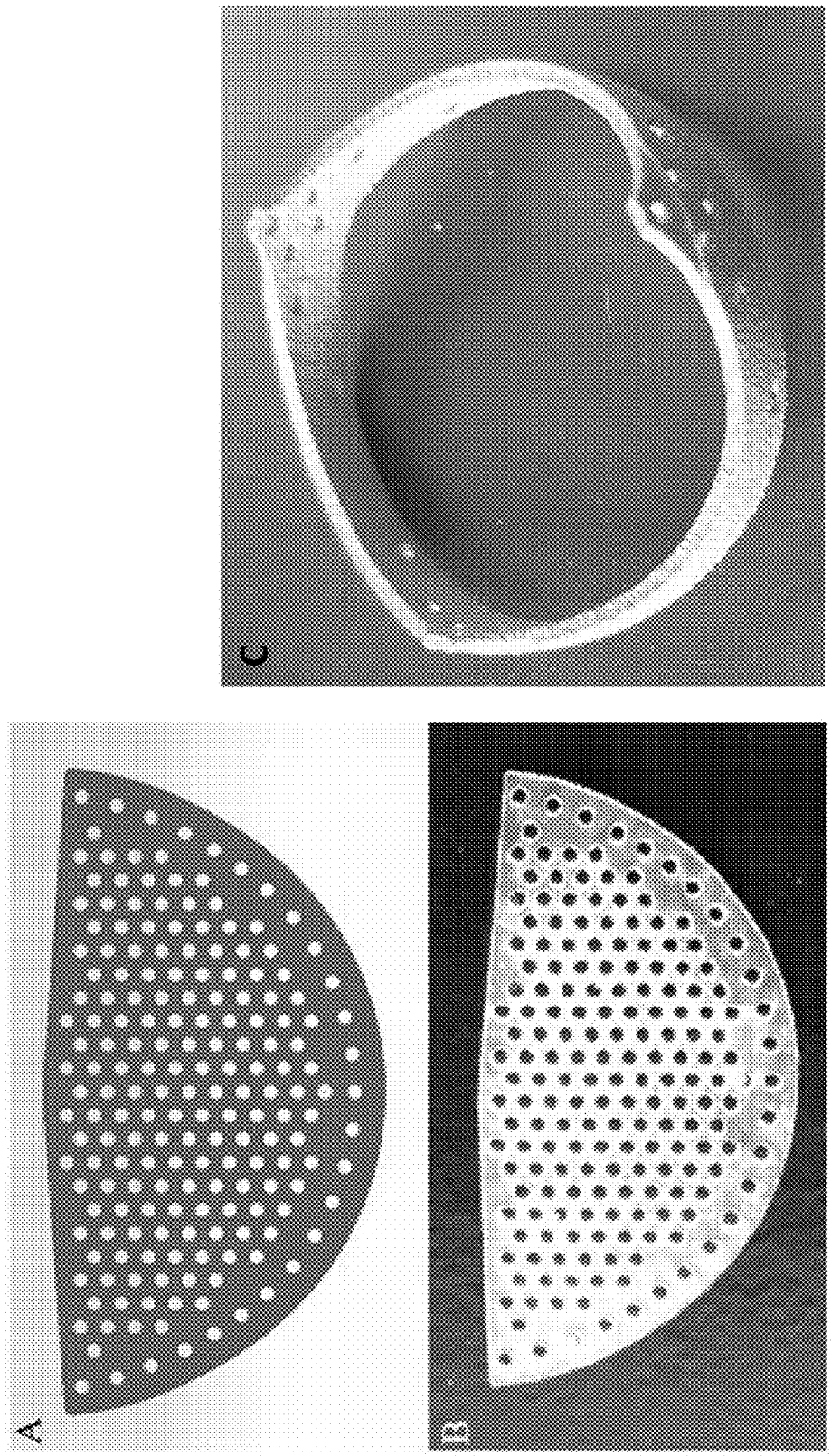
FIG. 26. A) The solid work drawing for the leaflets, B) the carbothane polymer leaflet after cutting by the laser cutting machine, C) the titanium frame.
Figure 27:
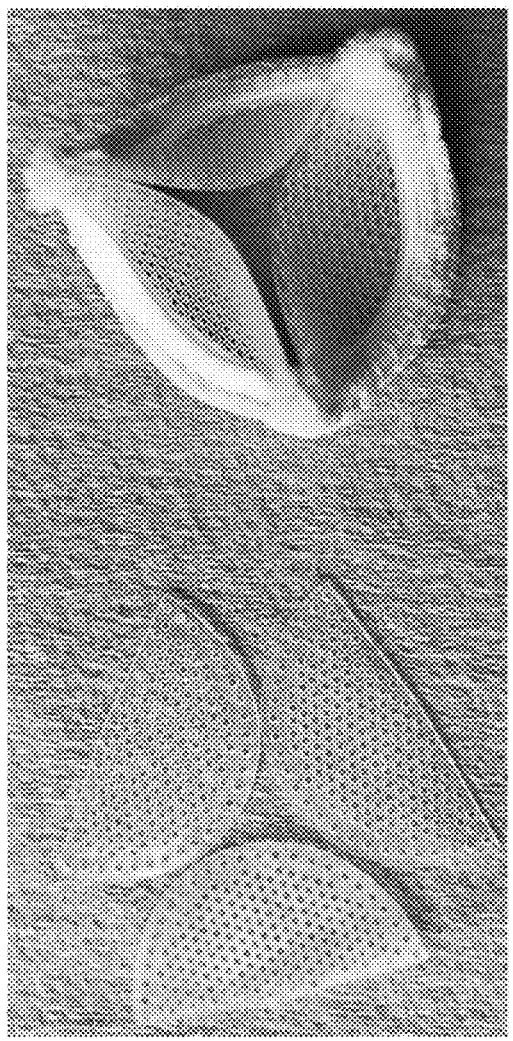
FIG. 27: A) the main body of the final hybrid valve from tope view with three carbothane polymer leaflets, B) The hybrid valve in 3D view.
Figure 27:
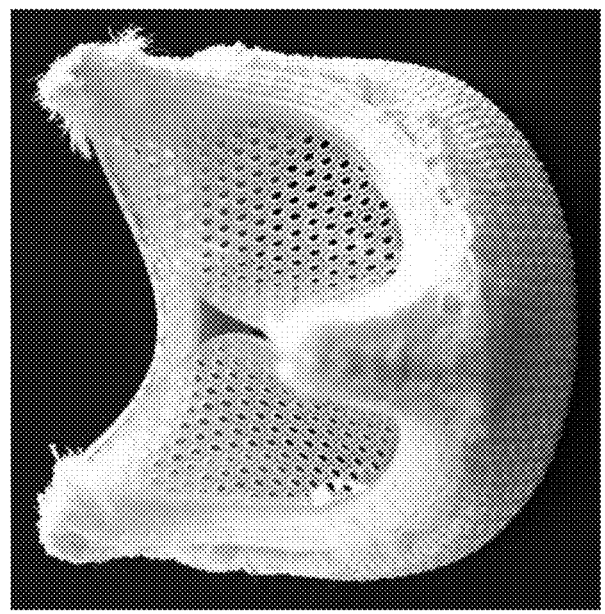

Procedure for Manufacturing the Main Body:
1—The carbothane polymer sheet with 250 µm thickness is transferred to a laser cutting machine (Versa VLS2.30 Laser System) to manufacture a small leaflet shape based on our design in FIG. 26, A. (settings for laser cutting machine are: power 5%, Speed 5% and point per inch (PPI) 500)
2—The carbothane polymer leaflets has a mesh with 1 mm holes (FIG. 26, B).
3—The mesh carbothane polymer leaflets are sewed to the titanium frame (FIG. 26, C) to generate the main body of the hybrid valve. (FIG. 27)
4—The valve was tested by an AWT machine for 50 million cycles with closing pressure 120 mm Hg at 800 rpm to evaluate the valve durability.

Procedure for Extracting Cells from the Jugular Vein:
1—Autoclave two forceps by using an autoclave pouch.
2—Clean the cell culture hood with some 70% Ethanol and Kimwipe. The blower on the cell culture should be on.
3—Spray some pipet tips, sterile razor blades, and a 6-well tissue culture plate with ethanol and place all of them on cell culture hood.
4—Spray the autoclaved pouch including the forceps (autoclaved forceps). Then place them in the cell culture hood.
5—A jugular vein is removed from animal body and transferred to the cell culture hood.
6—Wash the vein 3 times with sterile PBS 1× to removed blood clots and other debris.
7—Cut the vein to small pieces (3 mm×3 mm) by sterile razor blades.
8—The pieces should be washed by PBP 1× one time and then are transferred to a sterile 6-well petri dish.
9-6 pieces are flatten into each well (bottom side) by the sterile tweezers.
10—The petri dish is kept into the cell culture hood for 1 hour to let the tissue pieces completely attach to the surface of the petri dish.
11—A 4 ml mixed medium (2 ml SmGm-2 and 2 ml EGM-2 cell medium) is added to each well to cover the tissue pieces.
12—The pieces should be attached to surface of each well and not floated in the cell medium.
13—The petri dish is kept in a 37° C. incubator for 7 days to let cells migrate from tissue to surface of the petri dish.
14-50% of cell medium should be changed every 2 days with fresh mixed cell medium throughout 7 days.
15—At the end of day 7, the cell are migrated and grown into each well. (Note: see the tissue and cells by using a microscope with 10× objective)
16—In day 8, the cells are removed from the petri dish by trypsin 1× and are transferred to T-175 cell culture flasks.
17—Feed the cells every 2 days by changing 50% of mixed cell medium.
18—Proliferate the number of cells to 10 Million cells in one more week.
19—FIG. 7 shows the cell extracting from the jugular vein.

Procedure for Separating Cells:
1—A MACS system (Miltenyi Biotec Company) has been used to separate endothelial cells.
2—A 5 Million cells is counted and mixed with 800 µl mixed medium (400 µl SmGm-2 and 400 µl EGM-2).
3—The cell solution is mixed with 200 µl CD31 antibody (0.1 mg/ml CD31 Antibody-IgG2a, Bio-Rad Company) and store in a dark place in 4° C. place for 30 minutes.
4—FIG. 19 (step 1) shows a schematic to show the endothelial cells separation.
5-2 ml running buffer at 4° C. is added to the cell solution and is centrifuged at 1000 rpm in 4° C. for 5 minutes.
6—The solution is removed from the tube and is replaced with 80 µl buffer along with 20 µl microbeads.
7—The cell solution mixed with microbeads and store in 4° C. for 15 minutes. (Note: the microbeads are conjugated to endothelial cells in 15 minutes).
8—Spray the MultiStand with 70% ethanol and put it into the cell culture hood to be dried.
9—Assemble a MINMAC separator (a magnet) along with a MS column on the MultiStand.
10—Wash the column 3 times (3×500 µl) with buffer.
11—Transfer the cell solution to the MS column and let the solution pass through the MS column.
12—When the cell solution pass through the column, add 1.5 ml (3×500 µl) buffer to the column.
13—The labeled cell (endothelial cells) are within the column.
14—The unlabeled cells are passed through the column.
15—Detach the column from the magnet and place it in a 15 ml tube.
16-2 ml buffer add to the column and flush out the cells from the column to the 15 ml tube.
17—Collect and culture the labeled cells (endothelial cells) in a T-75 cell culture flask with 10 ml EGM-2 cell medium.
18—The unlabeled cells are collected and cultured in T 175 cell culture flasks with 20 ml SmGm-2.

The unlabeled cells are a mixture of smooth muscle cells and fibroblasts.

Extending Cell Separating Protocol:

The remaining cells are a mixed of smooth muscle cells and fibroblast/myofibroblast and we separate them by applying the following steps;

1—The remaining cells are incubated with the specific fibroblast antibody (biotinylated mouse antirat CD90, No. 554893; BD Biosciences) at 20° C. for 30 min. The treated cells are incubated with coated magnetic beads (goat anti-mouse IgG, No. 130-048-101; Miltenyi Biotec). Then, the fibroblasts coupled with magnetic beads are isolated by a magnetic column. The isolated cells (fibroblasts) are cultured by FBM cell medium (FIG. 19, Step 2).

2—The remaining untagged cells will be considered SMCs and will be cultured into cell culture flasks with SmGm-2 medium (FIG. 19, Step 3)

3—FIG. 19 shows the cell separation process in four steps.

Figure 28:
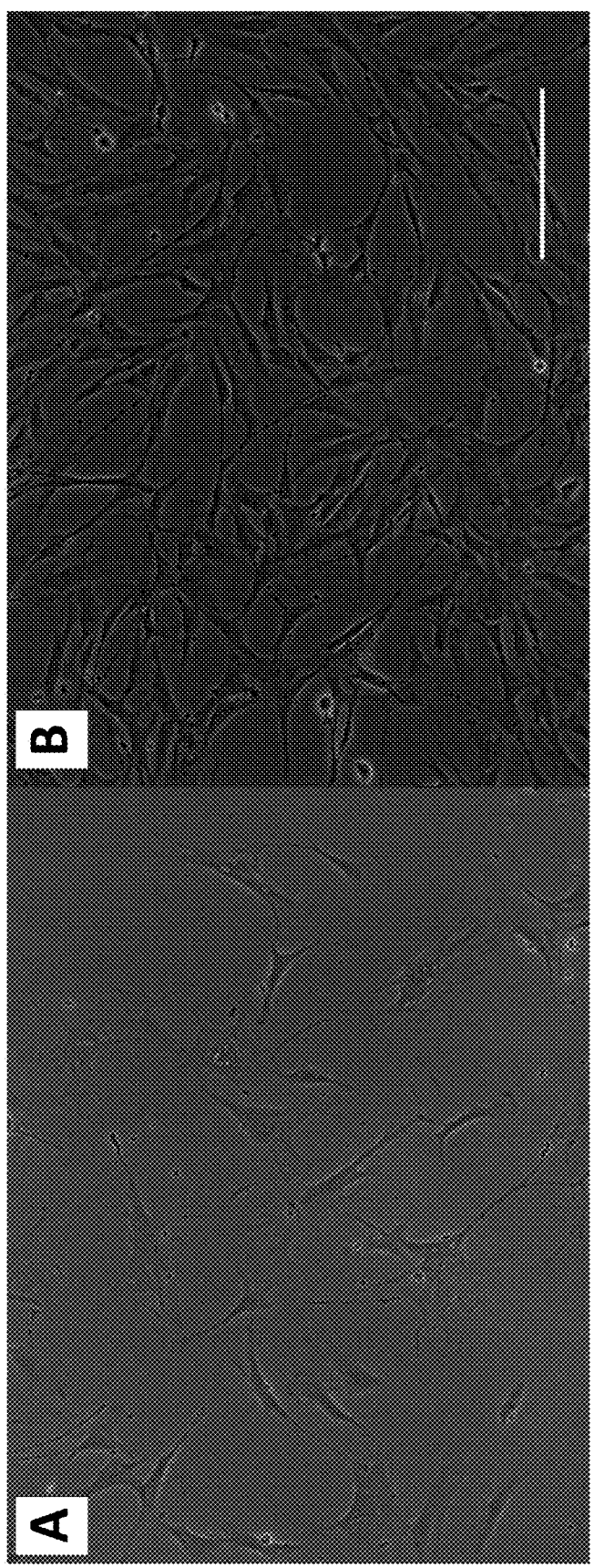
FIG. 28: A) Endothelial and B) Smooth muscle cells extracted, separated and used for the hybrid valve. Scale bar is 200 µm.

4—FIG. 28 shows images taken from endothelial and smooth muscle cells after cell separation process and used for the hybrid tissue engineered valve Procedure for preparing Fibronectin Solution:

1—Clean the cell culture hood with some 70% Ethanol and Kimwipe. The blower on the cell culture should be on.

2—Spray some sterilized pipette tips, two syringes with two needles and a bottle of sterilized DI water (500 ml). Put them into the cell culture hood.

3—Spray a Nalgene Sterile Bottle—Top—Filter (have a 500 ml capacity at least)

4—Spray the bottle of Fibronectin 0.5 mg (from rat plasma—Sigma-Aldrich F0635-0.5MG) and put it in the cell culture hood.

5—Let everything to dry from ethanol in the hood for 5 minutes.

6—Open the Nalgene Sterile Bottle—Top—Filter in the hood. Assemble and connect it to vacuum tube in the hood.

7—Add 500 ml DI water to the vacuum filter and open the vacuum valve to let DI water to pass the filter.

8—Open the top filter and replace it with the sterilized cap.

9—Transfer 2 ml filtered DI water into a 15 ml centrifuge tube.

10—Fill a sterilized syringe with 2 ml sterilized DI water.

11—Inject DI water into the bottle of Fibronectin and mix water with Fibronectin powder very well.

Try to not make bubbles when you are injecting water.

12—After dissolving Fibronectin in DI water, transfer the fibronectin solution (2 ml) into the sterilized DI water (500 ml) by a sterilized syringe.

13—Mix the fibronectin solution in the 500 ml DI bottle.

14—Split 500 ml Fibronectin solution into 10 50 ml-centrifuge tubes.

15—Label the centrifuge tubes with some information 1—Fibronectin solution 1 μg/ml, 2—Date 3—Initial name 16—Store the fibronectin tubes in a freezer (−20° C. temperature).

Procedure for Preparing a Sterile Hybrid Valve:

1—Autoclave two forceps by using an autoclave pouch.

2—Clean the cell culture hood with some 70% Ethanol and Kimwipe. The blower on the cell culture should be on.

3—Spray some pipet tips, a 6-well tissue culture plate with ethanol and place all of them on cell culture hood.

4—Spray the autoclaved pouch including the forceps (autoclaved forceps). Then place them in the cell culture hood.

5—Wash the mold with 70% Ethanol 3 times. Then leave it in the cell culture hood to be dried.

6—Pour a 20 ml 70% ethanol in a 50 ml tube.

7—Submerge the hybrid valve (main body) in 20 ml ethanol for 15 minutes

8—Place the hybrid valve into a sterile 6-well plate.

9—Leave the valve to be dried for 1 hour.

10—Remove the valve from the plate and place them into a 50 ml tube.

11—Wash the valve with sterile PBS 1× three times.

12—Transfer the valve into a new 50 ml tube.

13—Add a 20 ml Fibronectin solution with 1 μg/ml concentration to the tube.

14—Keep the valve in Fibronectin solution for 15 minutes

15—Transfer the valve to the 6-well plate and let it dry for 1 hour.

Figure 29:
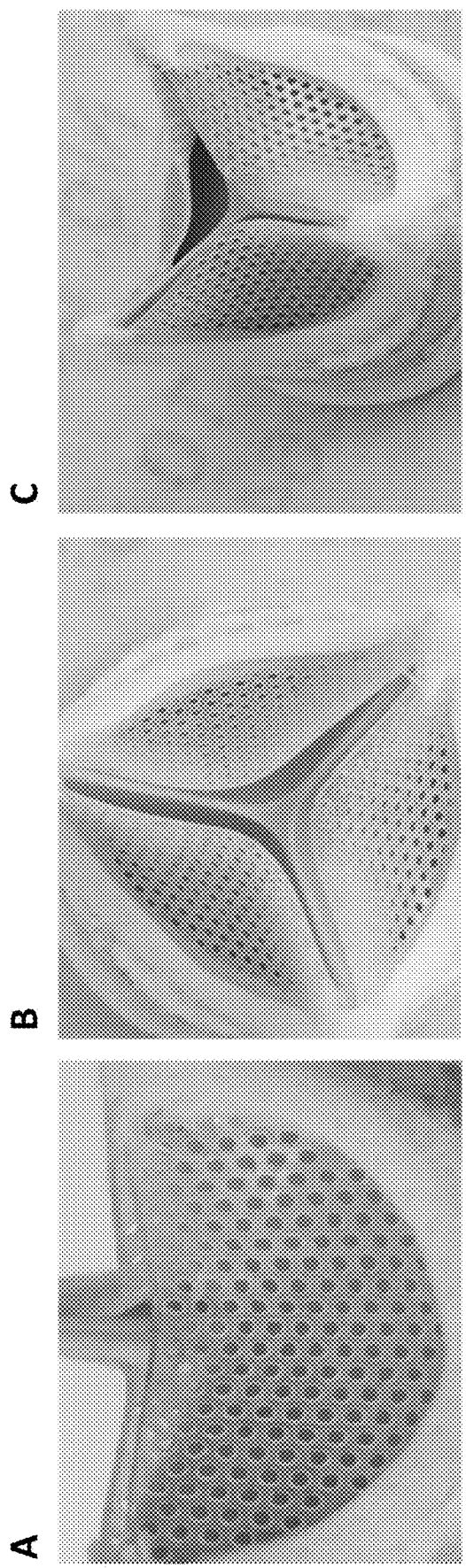
FIG. 29: the sterile hybrid valve adjusted into the sterile mold. (A) elevational view, (B) top plan view, and (C) perspective view.

16—FIG. 29 shows the hybrid valve adjusted into the sterile mold.

Procedure for Coating the Hybrid Valve with Smooth Muscle Cells (SMC's):

1—Clean the cell culture hood with some 70% Ethanol and Kimwipe. The blower on the cell culture should be on.

2—Spray some sterilized pipette tips, 1×DPBS, Neutralization Solution, Collagen type I bottle, Trypsin 1×, the autoclaved pouch including forceps, a 6 well Petri dish and sterile mold. Put all of them into the cell culture hood.

3—Open the autoclaved pouches including forceps.

4—Let the hybrid valve to be dried for 1 hour in the hood. (after submerging in 20 ml Fibronectin solution)

5—Let the mold to be dried after washing with 70% ethanol.

6—Transfer and adjust the valve into the mold.

7—Strat to make the collagen solution mixed with the unlabeled cells.

Note: The unlabeled cells are mixture of Smooth Muscle cells and Fibroblasts.

8—A 5 million unlabeled cells are counted and diluted in 100 μl SmGm-2 cell medium.

9-3150 μl collagen type I (4 mg/ml concentration) is mixed with 350 μl neutralization solution at 4° C.

10—The 100 μl cell solution is added to the collagen solution to make a uniform collagen/cell solution.

11—The final solution is poured to the mold holding the hybrid valve.

12—The mold is kept in an incubator at 37° C. for 90 minutes.

13—The hybrid valve is removed from the mold and is transferred to a sterile 6 well petri dish.

14-10 ml SM medium is added to the well, which holds the hybrid valve. The petri dish is kept in the incubator at 37° C.

Procedure for coating the Hybrid Valve with Endothelial Cells:

1—Clean the cell culture hood with some 70% Ethanol and Kimwipe.

2—Spray some sterilized pipette tips, 1×DPBS, the autoclaved pouch including forceps, a 6 well Petri dish and sterilized razor blades. Put all of them into the cell culture hood.

3—After 2 days incubating, the hybrid valve is loaded by endothelial cells.

4—The hybrid valve is moved to a new petri dish and washed 3 times by PBS 1×.

5—The mold is washed by 70% ethanol and dried in the cell culture hood.

6—A 0.5 Million endothelial cells is counted and mixed with 50 μl EGM-2 cell medium.

7—A 1800 μl collagen type I is mixed with a 200 μl neutralization solution at 4° C.

8—The cell solution is mixed with collagen solution to make a uniform solution.

9—The final solution is poured to the mold, which hold the hybrid valve.

10—The mold is kept in the incubator for 90 minutes.

11—The hybrid valve is moved to a new 6 well petri dish and is fed by 10 ml mixed medium (50% SmGm-2 cell medium and 50% EGM-2 cell medium).

FIG. 29: the sterile hybrid valve adjusted into the sterile mold.

12—The hybrid valve is fed by fresh medium (50% SmGm-2 cell medium and 50% EGM-2 cell medium) every day till the day of valve implantation.

Figure 30:
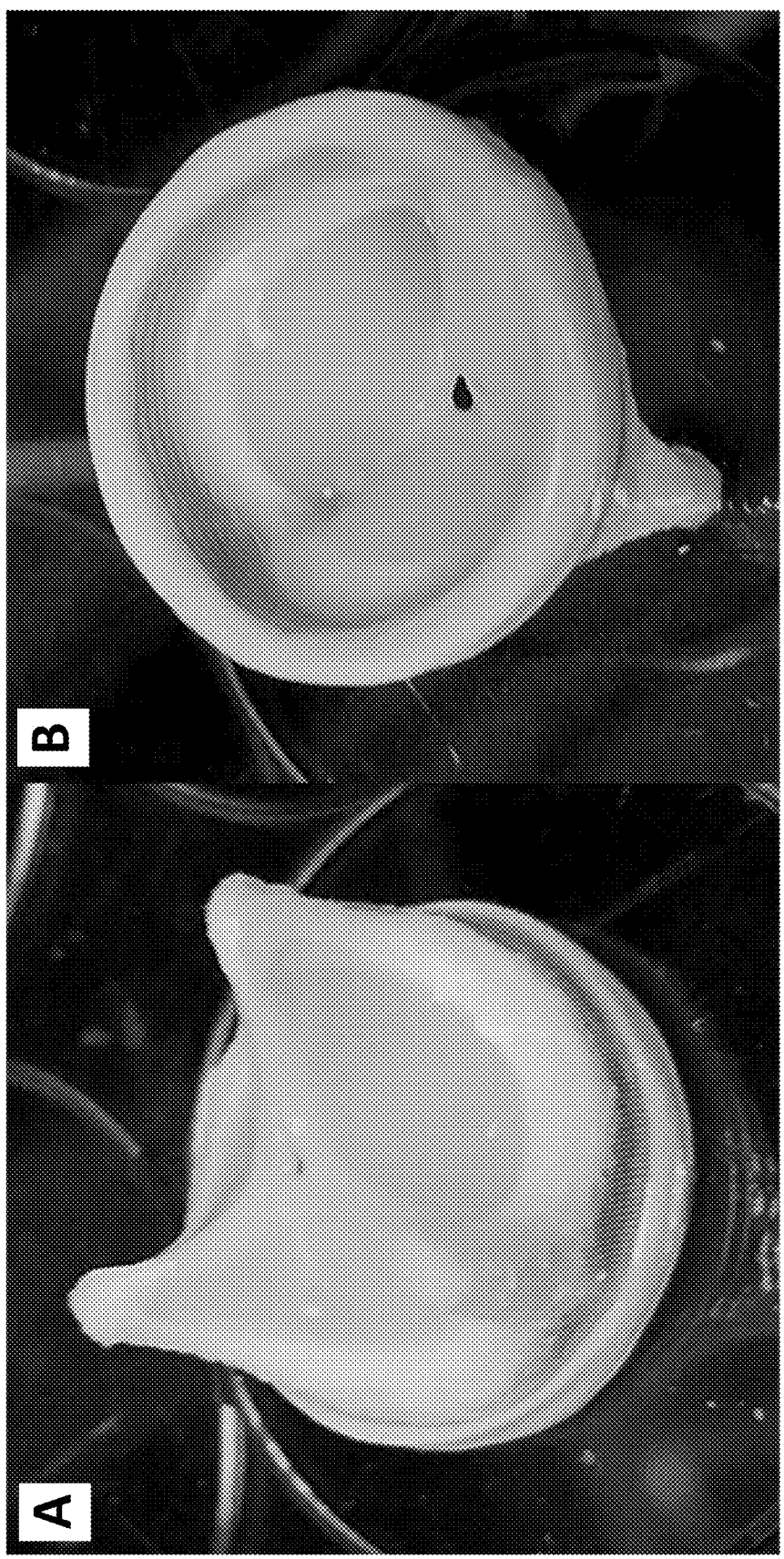
FIG. 30: A) top and B) bottom view of the final hybrid tissue valve engineered valve.

13—FIG. 30 shows the final hybrid tissue engineered valve.

Procedure for Implanting the Hybrid Valve into the Live Heart Sheep:

1—The final hybrid valve store in fresh medium (50% SmGm-2 cell medium and 50% EGM-2 cell medium) at 37° C. enriched with CO2 gas.

2—The valve is transported to the surgery room by a portable incubator and store in a sterile incubator till the valve implantation.

3—The open heart surgery is performed in Medical Center at UC Irvine.

4—The open heart surgery is followed based on Medical Center procedures (general anesthesia)

5—The hybrid valve is implanted in mitral or aortic positions.

6—The valve is kept wet by PBS 1× during the valve implantation.

Figure 31:
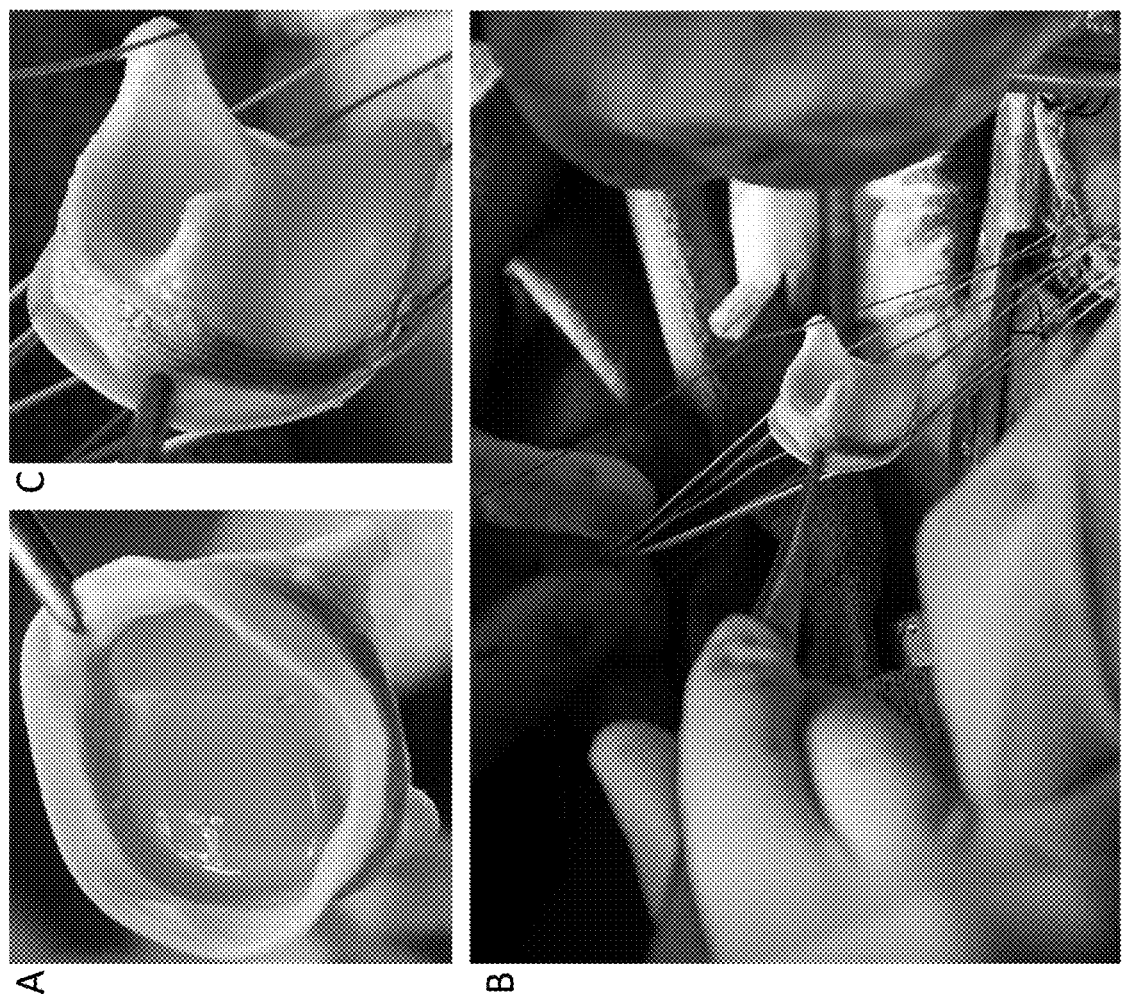
FIG. 31: the hybrid valve under implanting into a mitral position. (A) prior to implantation, (B) being guided into position, and (C) enlarged view of being guided into position.

7—FIG. 31 shows the implantation of the hybrid valve in a mitral position.

8—The cardiopulmonary perfusion data is recorded throughout the open heart surgery. Cardiopulmonary perfusion is recorded from initial anesthesia to consciousness.

9—The echocardiography (echo test or ultrasound imaging) is performed to monitor the performance of hybrid valve in patient heart.

10—The patient is moved to the recovery area and treated to recover from anesthesia.

11—The patient is treated and kept in the recovery area for post-surgery cares.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

All figures, tables, and appendices, as well as patents, applications, and publications, referred to above, are hereby incorporated by reference.

Some embodiments have been described in connection with the accompanying drawing. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A hybrid tissue engineered heart valve leaflet comprising a polyurethane core, wherein the polyurethane core is enclosed within two layers of cells, wherein a first layer comprises smooth muscle cells and/or fibroblast cells and a second layer comprises endothelial cells.

2. The hybrid tissue engineered heart valve leaflet according to claim 1, wherein the polyurethane core is a polycarbonate-based thermoplastic polyurethane.

3. The hybrid tissue engineered heart valve leaflet according to claim 2, wherein the polycarbonate-based thermoplastic polyurethane is carbothane.

4. The hybrid tissue engineered heart valve leaflet according to claim 1, wherein the two layers of cells further comprise collagen.

5. The hybrid tissue engineered heart valve leaflet according to claim 1, wherein the cells are extracted from a patient's vasculature.

6. The hybrid tissue engineered heart valve leaflet according to claim 5, wherein the cells are extracted from a peripheral vein of the patient.

7. The hybrid tissue engineered heart valve leaflet according to claim 6, wherein the peripheral vein is a saphenous or a jugular vein.

8. The hybrid tissue engineered heart valve leaflet according to claim 4, wherein the collagen is collagen type I.

9. The hybrid tissue engineered heart valve leaflet according to claim 1, wherein the first layer comprises 80-95% fibroblast cells and 5-20% smooth muscle cells.

10. A hybrid tissue engineered heart valve, comprising a frame; and at least two leaflets attached thereto in a configuration of a heart valve, wherein the leaflets are hybrid tissue engineered heart valve leaflets according to claim 1.

11. The hybrid tissue engineered heart valve according to claim 10, wherein the leaflets are made of a polycarbonate-based thermoplastic polyurethane.

12. The hybrid tissue engineered heart valve according to claim 11, wherein the polycarbonate-based thermoplastic polyurethane is carbothane.

13. The hybrid tissue engineered heart valve according to claim 10, wherein the valve is a tri-leaflet valve.

14. The hybrid tissue engineered heart valve according to claim 10, wherein the valve is a mitral valve with a dynamic saddle-shaped annulus.

15. The hybrid tissue engineered heart valve according to claim 10, wherein said frame comprises titanium.

16. A method of making the hybrid tissue engineered heart valve according to claim 10 for deployment in a patient, the method comprising:
cutting a polyurethane mesh into the shape of heart valve leaflets to obtain a polyurethane mesh leaflet,
attaching at least two polyurethane mesh leaflets to a heart valve frame,
harvesting autologous cells from the patient; and
growing the cells on the surface of the polyurethane mesh leaflets under culture conditions sufficient to enclose the polyurethane mesh leaflets.

17. The method according to claim 16, wherein the cells are harvested from a peripheral vessel, selected from a saphenous or a jugular vein.

18. The method according to claim 16, wherein the cells are smooth muscle cells, fibroblast cells and/or endothelial cells.

19. The method according to claim 18, comprising at least two steps of growing cells, a first step of growing smooth muscle cells and/or fibroblast cells on the leaflets to obtain first cell-enclosed leaflets, and a second step of growing endothelial cells on the surface of the first-cell enclosed leaflets to obtain endothelial cell-enclosed polyurethane mesh leaflets.

* * * * *